US011634736B2

(12) United States Patent
Fritsch et al.

(10) Patent No.: US 11,634,736 B2
(45) Date of Patent: Apr. 25, 2023

(54) METHODS AND MATERIALS FOR THE BIOSYNTHESIS OF COMPOUNDS INVOLVED IN THE TRICARBOXYLIC ACID CYCLE AND DERIVATIVES AND COMPOUNDS RELATED THERETO

(71) Applicant: INV NYLON CHEMICALS AMERICAS, LLC, Wilmington, DE (US)

(72) Inventors: Emilie Sophie Fritsch, Redcar (GB); Alexander Brett Foster, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 75 days.

(21) Appl. No.: 16/264,781

(22) Filed: Feb. 1, 2019

(65) Prior Publication Data

US 2019/0233852 A1 Aug. 1, 2019

Related U.S. Application Data

(60) Provisional application No. 62/694,602, filed on Jul. 6, 2018, provisional application No. 62/624,874, filed on Feb. 1, 2018.

(51) Int. Cl.
*C12P 7/46* (2006.01)
*C12N 9/10* (2006.01)
*C12N 9/88* (2006.01)
*C12N 15/74* (2006.01)

(52) U.S. Cl.
CPC .............. *C12P 7/46* (2013.01); *C12N 9/1025* (2013.01); *C12N 9/88* (2013.01); *C12N 15/74* (2013.01); *C12Y 203/03001* (2013.01); *C12Y 401/01006* (2013.01); *C12Y 402/01003* (2013.01)

(58) Field of Classification Search
None
See application file for complete search history.

(56) References Cited

U.S. PATENT DOCUMENTS

| | | | |
|---|---|---|---|
| 2008/0014618 A1 | 1/2008 | Bathe et al. | 435/115 |
| 2010/0285546 A1 | 11/2010 | Liao et al. | 435/145 |
| 2011/0125118 A1 | 5/2011 | Lynch | 604/367 |
| 2011/0244575 A1 | 10/2011 | Lipscomb et al. | 435/471 |
| 2017/0152533 A1 | 6/2017 | Kurek et al. | C12P 7/649 |
| 2017/0290341 A1 | 10/2017 | Cordova-Kreylos et al. | A01N 63/02 |
| 2018/0100160 A1 | 4/2018 | Bawdon et al. | |

OTHER PUBLICATIONS

Bailey, J.E., 1991 Science 252(5013): 1668-1675. (Year: 1991).*
Keasling, J.D., 2010 Science 330(6009): 1355-1358. (Year: 2010).*
Yadav, V.G., et al. 2012 Metabolic Engineering 14: 233-241. (Year: 2012).*
Harder, B-J., et al. 2016 Metabolic Engineering 38: 29-37. (Year: 2016).*
Crepin, L., et al. 2016 Metabolic Engineering 37: 92-101. (Year: 2016).*
Pohlmann, A., et al. 2006 Nat Biotechnol 24: 1257-1262 (6 pages); online publication published Sep. 10, 2006. (Year: 2006).*
Becker et al. "Metabolic engineering of the tricarboxylic acid cycle for improved lysine production by Corynebacterium glutamicum" Appl Environ Microbiol. 2009 75:7866-7869.
Blazeck et al. "Metabolic engineering of *Saccharomyces cerevisiae* for itaconic acid production" Appl Microbiol Biotechnol. 2014. 98:8155-8164.
Blazeck et al. "Metabolic engineering of Yarrowia lipolytica for itaconic acid production" Metab Eng. 2015 32:66-73.
Brightman, V. and Martin, W.R. "Pathway for the Dissimilation of Itaconic and Mesaconic Acids" Journal of Bacteriology 1961 82:376-382.
Byrd et al. "Bacterial control of Agromyces ramosus in soil" Can J Microbiol 1985 31:1157-1163.
Chen et al. "Identification of an itaconic acid degrading pathway in itaconic acid producing Aspergillus terreus" Appl Microbiol Biotechnol 2016 100:7541-7548.
Cooper, R.A. and Kornberg, H.L. "The utilization of itaconate by *Pseudomonas* sp" Biochemical Journal 1964 91:82-91.
Harder et al. "Model-based metabolic engineering enables high yield itaconic acid production by *Escherichia coli*" Metab Eng. 2016 38:29-37.
Harder et al. "Temperature-dependent dynamic control of the TCA cycle increases volumetric productivity of itaconic acid production by *Escherichia coli*" Biotechnol Bioeng. 2018 115:156-164.
Kanamasa et al. Cloning and functional characterization of the cis-aconitic acid decarboxylase (CAD) gene from Aspergillus terreus 2008 80:223-229.
Kinoshita, K. "About the Production of Itaconic Acid and Mannit Through a new Mould, Aspergillus itaconicus" Acta Phytochimica 1931 V(3): 271-287 (with English language machine translation).
Kim et al. "Production of itaconate by whole-cell bioconversion of citrate mediated by expression of multiple cis-aconitate decarboxylase (cadA) genes in *Escherichia coli*" Sci Rep. 2017 7:1-9.
Lee et al. "Metabolic engineering of *Escherichia coli* for enhanced production of succinic acid, based on genome comparison and in silico gene knockout simulation" Appl Environ Microbiol. 2005 71:7880-7887.
Li et al. "A clone-based transcriptomics approach for the identification of genes relevant for itaconic acid production in Aspergillus" Fungal Genet Biol. 2011 48:602-611.
Makkar, N.S. and Casida, L.E. "*Cupriavidus necator* gen. nov., sp. nov.; a Nonobligate Bacterial Predator of Bacteria in Soil" Int. J. of Systematic Bacteriology 1987 37:323-326.
Martin et al. "Noninductive metabolism of itaconic acid by *Pseudomonas* and *Salmonella* species" Journal of Bacteriology 1961 82:905-908.
Náray-Szabó, G and Mika, L. "Conservative evolution and industrial metabolism in Green Chemistry" Green Chem. 2018 20:2171-2191.

(Continued)

*Primary Examiner* — Marsha Tsay

(57) ABSTRACT

Methods and materials for the production of compounds involved in the TCA cycle, and/or derivatives thereof and/or compounds related thereto are provided. Also provided are products produced in accordance with these methods and materials.

5 Claims, 8 Drawing Sheets

Specification includes a Sequence Listing.

(56) References Cited

OTHER PUBLICATIONS

Okamoto et al. "Production of itaconic acid using metabolically engineered *Escherichia coli*" J Gen Appl Microbiol. 2014 60:191-197.
Otten et al. "Metabolic engineering of Corynebacterium glutamicum for the production of itaconate" Metab Eng. 2015 30:156-165.
Russell, J.B. "The Energy Spilling Reactions of Bacteria and Other Organisms" Journal of Molecular Microbiology and Biotechnology 2007 13:1-11.
Sasikaran et al. "Bacterial itaconate degradation promotes pathogenicity" Nature Chemical Biology 2014 10: 371-377.
Schlegel, H.G. and Vollbrecht, D. "Formation of the Dehydrogenases for Lactate, Ethanol and Butanediol in the Strictly Aerobic Bacterium Alcaligenes eutrophus" Journal of General Microbiology 1980 117:475-481.
Sillman, C. E. and Casida, L. E. "Isolation of nonobligate bacterial predators of bacteria from soil" Can J Microbiol 1986 32:760-762.
Steinbüchel, A. and Schlegel, H.G. "Excretion of pyruvate by mutants of *Alcaligenes eutrophus*, which are impaired in the accumulation of poly(β-hydroxybutyric acid) (PHB), under conditions permitting synthesis of PHB" Appl Microbiol Biotechnol 1989 31:168-175.
Vollbrecht et al. "Excretion of metabolites by hydrogen bacteria. 1. Autotrophic and heterotrophic fermentations" Eur J Appl Microbiol Biotechnol 1978 6:145-155.
Vollbrecht et al. "Excretion of metabolites by hydrogen bacteria. 4. Respiration rate-dependent formation of primary metabolites and of poly-3-hydroxybutanoate" European J. Appl. Microbiol. Biotechnol. 1979 7:267-276.
Vollbrecht, D. and Schlegel, H.G. "Excretion of metabolites by hydrogen bacteria. 2. Influences of aeration, pH, temperature, and age of cells" European J. Appl. Microbiol. Biotechnol. 1978 6:157-166.
Vollbrecht, D. and Schlegel, H.G. "Excretion of metabolites by hydrogen bacteria. 3. D(-)-3- Hydroxybutanoate" European J. Appl. Microbiol. Biotechnol. 1979 7:259-266.
Vuoristo et al. "Metabolic engineering of itaconate production in *Escherichia coli*" Appl Microbiol Biotechnol. 2015 99:221-228.
Xu et al. "Fumaric acid production in *Saccharomyces cerevisiae* by simultaneous use of oxidative and reductive routes" Bioresour Technol. 2013 148:91-96.
Yamamoto et al. "Challenges in the production of itaconic acid by metabolically engineered *Escherichia coli*" Bioengineered. 2015 6:303-306.
Yim et al. "Metabolic engineering of *Escherichia coli* for direct production of 1,4-butanediol" Nat Chem Biol. 2011 7:445-452.
Zeph, L.E. and Casida, L.E. "Gram-negative versus gram-positive (actinomycete) nonobligate bacterial predators of bacteria in soil" Applied and Environmental Microbiology 1986 52:819-823.
International Search Report and Written Opinion in PCT/US2019/016219 dated May 6, 2019.
International Preliminary Report on Patentability in PCT/US2019/016219 dated Aug. 4, 2020.
Bafana, R. et al., "New approaches for itaconic acid production: bottlenecks and possible remedies," Critical Reviews in Biotechnology, vol. 38, No. 1, pp. 68-82 (Apr. 2017).
Extended European Search Report received for EP application No. 19746921.6, dated Sep. 24, 2021, 7 pages.
Zhao, M. et al., "Itaconic acid production in microorganisms," Biotechnology Letters, vol. 40, No. 3, pp. 455-464 (Jan. 2018).

\* cited by examiner

SEQUENCE LISTING

```
<160> NUMBER OF SEQ ID NOS: 65

<210> SEQ ID NO 1
<211> LENGTH: 490
<212> TYPE: PRT
<213> ORGANISM: A. terreus

<400> SEQUENCE: 1

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205
```

```
Ser Ala Gln Tyr Gly Gly Met Val Lys Arg Val Gln His Gly Phe Ala
    210                 215                 220
Ala Arg Asn Gly Leu Leu Gly Gly Leu Leu Ala His Gly Gly Tyr Glu
225                 230                 235                 240
Ala Met Lys Gly Val Leu Glu Arg Ser Tyr Gly Gly Phe Leu Lys Met
                245                 250                 255
Phe Thr Lys Gly Asn Gly Arg Glu Pro Pro Tyr Lys Glu Glu Glu Val
                260                 265                 270
Val Ala Gly Leu Gly Ser Phe Trp His Thr Phe Thr Ile Arg Ile Lys
            275                 280                 285
Leu Tyr Ala Cys Cys Gly Leu Val His Gly Pro Val Glu Ala Ile Glu
    290                 295                 300
Asn Leu Gln Gly Arg Tyr Pro Glu Leu Leu Asn Arg Ala Asn Leu Ser
305                 310                 315                 320
Asn Ile Arg His Val His Val Gln Leu Ser Thr Ala Ser Asn Ser His
                325                 330                 335
Cys Gly Trp Ile Pro Glu Glu Arg Pro Ile Ser Ser Ile Ala Gly Gln
                340                 345                 350
Met Ser Val Ala Tyr Ile Leu Ala Val Gln Leu Val Asp Gln Gln Cys
            355                 360                 365
Leu Leu Ser Gln Phe Ser Glu Phe Asp Asp Asn Leu Glu Arg Pro Glu
    370                 375                 380
Val Trp Asp Leu Ala Arg Lys Val Thr Ser Ser Gln Ser Glu Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Ile Thr Glu Ser Val Glu Lys Pro Leu Gly Val
                420                 425                 430
Lys Glu Pro Met Pro Asn Glu Arg Ile Leu His Lys Tyr Arg Thr Leu
            435                 440                 445
Ala Gly Ser Val Thr Asp Glu Ser Arg Val Lys Glu Ile Glu Asp Leu
    450                 455                 460
Val Leu Gly Leu Asp Arg Leu Thr Asp Ile Ser Pro Leu Leu Glu Leu
465                 470                 475                 480
Leu Asn Cys Pro Val Lys Ser Pro Leu Val
                485                 490
```

<210> SEQ ID NO 2
<211> LENGTH: 1473
<212> TYPE: DNA
<213> ORGANISM: Artificial sequence
<220> FEATURE:
<223> OTHER INFORMATION: Synthetic

<400> SEQUENCE: 2

```
atgaccaaac aaagcgcgga cagcaatgca aaatcgggtg tgactagcga aatctgccac      60
tgggcgtcga acctggcgac cgacgatatc cccagcgacg tgctcgaacg cgccaagtac     120
ctgatcctgg atgggatcgc ctgcgcctgg gtcggtgccc gggtgccgtg gtcggaaaag     180
tacgtgcaag ccacgatgag cttcgagcct cggggcgcgt gccgcgtgat cggctacggc     240
caaaagctcg gcccagtcgc agccgccatg accaactcgg catttatcca ggccacagag     300
ctggacgact atcattcgga agcgcctctg cactccgcca gcatcgtgct gcccgccgtg     360
ttcgccgcca gcgaagtgct ggccgaacag ggtaagacga tctcgggcat tgacgtcatc     420
ctggcggcca tcgtcggctt cgagagcggc ccgcgcatcg gcaaggccat ctatggctcc     480
```

```
gacttgttga acaacggctg gcattgcggc gccgtgtacg gcgcccccgc gggcgccctg    540
gccaccggca agctcctggg cctgacgccg gacagcatgg aagatgccct gggcatcgcg    600
tgcacccagg cgtgcggcct gatgtcggcg caatacggcg gcatggtcaa gcgcgtccag    660
cacggcttcg cagcgcgtaa cgggctgctg ggggggctgc tggcgcatgg gggctatgaa    720
gccatgaagg gcgtgctgga acgcagctac ggcggcttcc tcaagatgtt taccaagggc    780
aacgggcggg aaccccgta caaggaagag aagtcgtgg cgggcctggg ctccttctgg    840
catacccttca ccatccgcat caagctgtac gcgtgctgcg gcttggtcca cggtccggtc    900
gaggccatcg agaatctcca gggccgctat cccgagctgc tgaaccgggc gaacctgagc    960
aacattcgtc acgtgcacgt gcagctgagc accgcatcga actcgcactg cggttggatt   1020
ccggaggaac gcccgatctc ctcgatcgca ggcagatgt cggtggcgta catcctggcc   1080
gtgcagctcg tcgatcagca gtgcctcctg agccagttct ccgagttcga cgacaatttg   1140
gaacggcccg aagtctggga cctggcgcgc aaggtgacgt cgtcccaatc cgaggagttc   1200
gaccaggacg gcaactgcct gagcgccggt cgggtccgca tcgagttcaa cgacggctcg   1260
tccatcaccg agtccgtgga aaagccgctg gcgtgaagg aaccgatgcc gaacgaacgc   1320
atcctgcaca agtaccgcac gctggccggc tcggtgaccg acgagtcccg cgtgaaggag   1380
attgaggacc tggtgctcgg cctggaccgc ctgacggata tctcgccgct gctggaactg   1440
ctcaactgcc ccgtcaagtc gccgctggtc tga                               1473
```

<210> SEQ ID NO 3
<211> LENGTH: 437
<212> TYPE: PRT
<213> ORGANISM: C. glutamicum

<400> SEQUENCE: 3

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190
```

```
Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 4
<211> LENGTH: 1314
<212> TYPE: DNA
<213> ORGANISM: Artificial sequence
<220> FEATURE:
<223> OTHER INFORMATION: Synthetic

<400> SEQUENCE: 4
atgtttgagc gtgatattgt agcaactgat aataataaag ccgtcttgca ctacccgggt      60
ggcgagttcg agatggatat catcgaagcg agcgagggca acaacggcgt ggtcctgggc     120
aagatgctgt cggaaaccgg cctgatcacc tttgacccgg gctacgtcag cacgggcagc     180
accgagtcga agatcacgta tattgacggc gacgccggca tcctgcggta ccggggttat     240
gacatcgcgg acctggcgga gaatgccacc ttcaacgagg tgtcctacct cctcatcaat     300
ggcgagctgc caacgcccga cgaactgcac aagttcaacg acgaaatccg ccaccatacc     360
ctgctggacg aagatttcaa gtcccaattc aacgtgttcc cgcgcgacgc gcacccgatg     420
gccacgctgg cgtccagcgt caacatcctg tcgacctact accaggacca gctgaacccc     480
ctcgacgaag cgcagctgga caaggccacc gtgcgtctga tggccaaggt ccctatgctg     540
gcggcctacg cgcaccgcgc cgcaagggc gccccgtaca tgtatccgga caactcgctg     600
aacgcacgcg agaacttcct ccgcatgatg ttcggctacc ctaccgaacc gtacgaaatc     660
```

```
gacccgatca tggtgaaggc cctggacaag ttgctgatct tgcatgcgga ccacgaacag    720
aactgcagca cctcgacggt gcggatgatc ggcagcgccc aggccaacat gttcgtgtcc    780
attgcgggtg gcatcaacgc cctgtcgggc ccgctgcacg ggggggccaa ccaagccgtc    840
ctggaaatgc tggaggacat caagtcgaat cacggcggcg acgccacgga atttatgaac    900
aaggtcaaga caaggaaga tggcgtgcgg ttgatgggct tcggccaccg cgtgtacaag     960
aactatgatc gcgggcggc catcgtcaaa gaaacagcgc atgaaatcct ggagcacctg    1020
ggcggggacg atctcctgga cctggccatc aagttggaag agatcgccct gcggacgat    1080 tacttcatca gccgcaagct gtacccgaac gtcgacttct ataccggcct gatctaccgc    1140
gcaatgggct tccccacaga cttcttcacg gtgctgttcg caatcggtcg cctgccgggc    1200
tggatcgccc attaccgcga gcaactgggc gcagccggca acaagatcaa ccgcccccgc    1260
caggtctaca ccggcaacga atcgcgtaag ctcgtgccgc gtgaggaacg ctga          1314
```

<210> SEQ ID NO 5
<211> LENGTH: 433
<212> TYPE: PRT
<213> ORGANISM: C. necator

<400> SEQUENCE: 5

```
Met Thr Pro Ser Asp Val Lys Ala Thr Leu Ser Phe Ser Asp Gly Ser
1               5                   10                  15

Pro Ser Val Glu Leu Pro Ile Tyr Thr Gly Thr Val Gly Pro Asp Val
            20                  25                  30

Ile Asp Ile Arg Lys Leu Tyr Gly Gln Thr Gly Lys Phe Thr Tyr Asp
        35                  40                  45

Pro Gly Phe Met Ser Thr Ala Ser Cys Asn Ser Lys Ile Thr Tyr Ile
    50                  55                  60

Asp Gly Asp Lys Gly Glu Leu Leu Tyr Arg Gly Tyr Pro Ile Glu Gln
65                  70                  75                  80

Leu Ala Gln Lys Cys Asp His Leu Glu Thr Cys Tyr Leu Leu Leu Lys
                85                  90                  95

Gly Glu Leu Pro Asn Ala Lys Gln Lys Glu Glu Phe Val Gly His Val
            100                 105                 110

Met Asn His Thr Met Val His Glu Gln Met Gln Phe Phe Met Arg Gly
        115                 120                 125

Phe Arg Arg Asp Ala His Pro Met Ala Val Leu Thr Gly Met Val Gly
    130                 135                 140

Ala Met Ser Ala Phe Tyr His Asp Ala Met Asp Ile Asp Asp Pro His
145                 150                 155                 160

Gln Arg Glu Ile Ser Ala Ile Arg Leu Ile Ala Lys Met Pro Thr Leu
                165                 170                 175

Val Ala Met Ala Tyr Lys Tyr Asn Ile Gly Gln Pro Tyr Ile Tyr Pro
            180                 185                 190

Gln Asn Asp Leu Ser Tyr Ser Gly Asn Phe Met Arg Met Phe Gly
        195                 200                 205

Thr Pro Cys Ala Pro Tyr Thr Val Asn Pro Val Leu Glu Arg Ala Leu
    210                 215                 220

Asp Arg Ile Phe Ile Leu His Ala Asp His Glu Gln Asn Ala Ser Thr
225                 230                 235                 240

Ser Thr Val Arg Leu Ala Gly Ser Ser Gly Thr Asn Pro Phe Ala Ala
                245                 250                 255
```

| Ile | Ala | Ala | Gly | Val | Ala | Cys | Leu | Trp | Pro | His | Gly | Gly | Ala |
|     |     | 260 |     |     |     |     | 265 |     |     |     | 270 |     |     |

Asn Glu Ala Ala Leu Lys Met Leu Glu Glu Ile Gly Ser Val Asp Asn
            275                 280                 285

Ile Asn Glu Phe Ile Lys Gln Val Lys Asp Lys Asn Ser Gly Val Arg
        290                 295                 300

Leu Met Gly Phe Gly His Arg Val Tyr Lys Asn Tyr Asp Pro Arg Ala
305                 310                 315                 320

Lys Leu Met Arg Glu Thr Cys His Glu Val Leu Glu Glu Leu Gly Leu
                325                 330                 335

His Asn Asp Pro Leu Phe Lys Leu Ala Met Glu Leu Gly Lys Ile Ala
            340                 345                 350

Leu Glu Asp Glu Tyr Phe Val Ser Arg Lys Leu Tyr Pro Asn Val Asp
        355                 360                 365

Phe Tyr Ser Gly Ile Val Gln Arg Ala Leu Gly Ile Pro Thr Ser Leu
370                 375                 380

Phe Thr Cys Ile Phe Ala Leu Ala Arg Thr Pro Gly Trp Ile Ser Gln
385                 390                 395                 400

Trp Glu Glu Met Ile Thr Asp Pro Glu Tyr Lys Ile Gly Arg Pro Arg
                405                 410                 415

Gln Leu Phe Val Gly Ala Ala Thr Arg Asp Val Pro Asp Val Ala Lys
            420                 425                 430

Arg

<210> SEQ ID NO 6
<211> LENGTH: 1302
<212> TYPE: DNA
<213> ORGANISM: Artificial sequence
<220> FEATURE:
<223> OTHER INFORMATION: Synthetic

<400> SEQUENCE: 6

```
atgacaccta gcgacgtgaa agcaacactc tcattttccg acggctcccc tagcgtagag      60
ctgccaattt acaccggcac cgtcggtccc gacgtcatcg acatccgcaa actgtacggc     120
cagaccggca agttcaccta cgaccccggc ttcatgtcga ccgcctcctg caactcgaag     180
atcacgtaca tcgatggtga caagggcgag ctgctgtatc ggggctaccc gatcgaacag     240
ctggcccaga agtgcgacca cctggaaacg tgctacttgc tgctgaaggg cgaactgccg     300
aacgccaagc aaaaggaaga gttcgtcggc catgtgatga ccacacgat ggtgcacgag      360 cagatgcagt tcttcatgcg tgggttccgc cgggacgccc acccgatggc cgtgctgacc     420
ggcatggtcg gcgccatgtc ggcgttttac catgacgcga tggatattga tgacccgcac     480
cagcgcgaga ttagcgccat ccgcttgatc gcgaagatgc cgaccctggt ggcgatggcc     540
tataagtaca acatcggcca gccgtacatc tacccgcaga acgacctgtc gtacagcggg     600
aacttcatgc ggatgatgtt cggcaccccg tgcgccccgt ataccgtgaa ccccgtcctg     660
gaacgcgcgc tggaccgcat cttcatcctg catgcagacc atgagcaaaa cgcctcgacc     720
tcgactgtgc gcctcgcagg ctcctcgggc acgaacccgt cgccgccat cgcggcaggg     780 gtcgcgtgcc tctgggccc cgcccacggt ggcgccaatg aagccgccct gaagatgctg     840
gaagaaatcg gctccgtgga acatcaac gagttcatca acaggtgaa ggacaagaac      900 agcggtgtcc gcctgatggg cttcggccac gcgtgtaca agaactacga cccgcgcgcc     960
aagctgatgc gtgaaacgtg ccacgaagtg ctggaagaac tcgggttgca caacgacccc    1020
```

-continued

| | |
|---|---|
| ctcttcaagc tcgcgatgga actggaaaag atcgccctgg aggacgagta ctttgtctcg | 1080 |
| cgcaagctgt atccgaatgt cgacttctac agcggcatcg tgcaacgggc cctgggcatc | 1140 |
| ccgacgtccc tgttcacgtg catcttcgcc ctggcccgca ccccgggttg atcagccag | 1200 |
| tgggaagaaa tgatcaccga tccggagtat aagatcggcc ggccccgcca gctgttcgtg | 1260 |
| ggggcggcga cgcgcgacgt gccagatgtg gcgaagcgct ga | 1302 |

<210> SEQ ID NO 7
<211> LENGTH: 1314
<212> TYPE: DNA
<213> ORGANISM: Artificial sequence
<220> FEATURE:
<223> OTHER INFORMATION: Synthetic

<400> SEQUENCE: 7

| | |
|---|---|
| atgttcgaac gtgatattgt ggcgacagat aacaacaagg cagtcttgca ctacccgggc | 60 |
| ggggagttcg agatggatat catcgaagcg agcgaaggca acaacggcgt ggtcctgggc | 120 |
| aagatgctct ccgaaaccgg cctgatcacc ttcgaccccg gttacgtgag cactggcagc | 180 |
| accgagtcga agatcaccta catcgacggc gatgcgggca tcctgcgcta tcggggctat | 240 |
| gacatcgccg acctcgcgga gaacgccaca ttcaacgaag tgagctacct cctcattaac | 300 |
| ggcgagctcc cgaccccgga cgaactgcac aagttcaacg acgagatccg gcatcacacg | 360 |
| ctgctggatg aggacttcaa gtcgcagttc aacgtgttcc ccgcgacgc acacccgatg | 420 |
| gcgaccctgg catcgagcgt gaatatcctg tcgacgtact accaggacca gctgaatccg | 480 |
| ctcgacgaag cgcagctgga taaggccact gtccgcctca tggcgaaagt cccgatgctg | 540 |
| gccgcatacg cgcaccgcgc ccgcaagggt gccccttaca tgtacccgga caactcgctg | 600 |
| aacgcgcgcg agaatttcct gcggatgatg ttcggctatc ccacggaacc gtacgaaatc | 660 |
| gacccgatca tggtcaaggc cctggacaag ctgctgatcc tgcacgccga ccacgagcag | 720 |
| aattgctcca gtccacggt gcggatgatc ggctcggcgc aagccaacat gttcgtcagc | 780 |
| atcgcgggcg ggatcaacgc gctgtccggc cccctccacg gcggcgccaa ccaagccgtg | 840 |
| ctggaaatgc tggaagatat caagtcgaac cacggcggcg acgcaaccga gttcatgaat | 900 |
| aaagtcaaga caaagaaga tggcgtccgt ctgatgggct tcggtcatcg cgtctacaag | 960 |
| aactacgacc cgcgcgcagc catcgtgaag gaaacggcgc acgaaatcct ggagcatttg | 1020 |
| gcggcgacg acttgctgga cctggccatt aagctcgaag agattgccct ggccgacgac | 1080 |
| tactttatca gccgcaagct gtaccccaat gtggacttct ataccggctt gatctatcgt | 1140 |
| gcgatgggct tcccaaccga tttcttcacc gtcctgttcg ccatcggccg tctgcccggc | 1200 |
| tggatcgccc attatcgcga gcagctgggg cggcgggta acaagatcaa tcgcccgcgt | 1260 |
| caggtgtaca ccgggaacga atcgcgcaaa ctggtgccgc gcgaagaacg gtga | 1314 |

<210> SEQ ID NO 8
<211> LENGTH: 901
<212> TYPE: PRT
<213> ORGANISM: C. necator

<400> SEQUENCE: 8

Met Pro His Asn Leu Lys Asn Thr Leu Lys Glu Phe Lys Ile Gly Ser
1               5                   10                  15

Ser Gly Lys Gly Gln Tyr Tyr Ser Leu Pro Gln Leu Gly Glu Glu Leu
            20                  25                  30

Asp Val Ala Val Gly Arg Leu Pro Val Ser Ile Arg Val Val Leu Glu

```
             35                  40                  45
Ser Val Leu Arg Asn Cys Asp Gly Lys Lys Val Thr Glu Glu His Val
            50                  55                  60
Arg Gln Leu Ala Asn Trp Lys Pro Asn Ala Glu Arg Val Asp Glu Ile
 65                  70                  75                  80
Pro Phe Val Val Ala Arg Val Val Leu Gln Asp Phe Thr Gly Val Pro
                    85                  90                  95
Leu Leu Ala Asp Leu Ala Ala Met Arg Asn Val Ala Glu Lys Met Gly
                100                 105                 110
Lys Asn Pro Lys Lys Ile Glu Pro Leu Val Pro Val Asp Leu Val Val
            115                 120                 125
Asp His Ser Val Gln Val Asp His Phe Arg Glu Lys Lys Ala Leu Asp
            130                 135                 140
Leu Asn Met Gln Leu Glu Phe Gln Arg Asn Asn Glu Arg Tyr Gln Phe
145                 150                 155                 160
Met Lys Trp Gly Met Gln Ala Phe Asp Thr Phe Gly Val Val Gln Pro
                165                 170                 175
Gly Phe Gly Ile Val His Gln Val Asn Leu Glu Tyr Leu Ala Arg Gly
                180                 185                 190
Val His Lys Lys Asp Gly Val Tyr Tyr Pro Asp Thr Leu Val Gly Thr
            195                 200                 205
Asp Ser His Thr Thr Met Ile Asn Gly Ile Gly Val Val Gly Trp Gly
210                 215                 220
Val Gly Gly Ile Glu Ala Glu Ala Gly Met Leu Gly Gln Pro Val Tyr
225                 230                 235                 240
Phe Leu Thr Pro Asp Val Val Gly Val Glu Leu Lys Gly Arg Leu Arg
                245                 250                 255
Glu Gly Val Thr Ala Thr Asp Leu Val Leu Thr Ile Thr Glu Met Leu
                260                 265                 270
Arg Lys Glu Lys Val Val Gly Lys Phe Val Glu Phe Phe Gly Glu Gly
            275                 280                 285
Thr Ala Ser Leu Ala Leu Pro Asp Arg Ala Thr Ile Gly Asn Met Ala
            290                 295                 300
Pro Glu Tyr Gly Ala Thr Met Gly Phe Phe Pro Val Asp Glu Lys Thr
305                 310                 315                 320
Ile Asp Tyr Phe Lys Gly Thr Gly Arg Thr Glu Glu Glu Ile Ala Ala
                325                 330                 335
Phe Glu Gly Tyr Phe Arg Ala Gln Lys Met Phe Gly Ile Pro Arg Ala
                340                 345                 350
Gly Glu Ile Asp Tyr Ser Lys Val Val Thr Leu Asp Leu Gly Thr Val
                355                 360                 365
Ala Pro Ser Leu Ala Gly Pro Lys Arg Pro Gln Asp Arg Ile Glu Ile
            370                 375                 380
Gly Asn Val Lys Ser Thr Phe Ala Ser Leu Phe Ser Lys Pro Val Ala
385                 390                 395                 400
Glu Asn Gly Phe Asn Lys Glu Ala Ala Asp Leu Asp Arg Ala Tyr Thr
                405                 410                 415
Thr Thr Asp Gly Leu Glu Val Lys Asn Gly Asp Val Leu Ile Ala Ala
                420                 425                 430
Ile Thr Ser Cys Thr Asn Thr Ser Asn Pro Ser Val Leu Leu Gly Ala
            435                 440                 445
Gly Leu Leu Ala Lys Lys Ala Val Glu Ala Gly Leu Thr Val Ala Pro
            450                 455                 460
```

His Ile Lys Thr Ser Leu Ala Pro Gly Ser Arg Val Thr Glu Tyr
465                 470                 475                 480

Leu Thr Ala Ala Gly Leu Leu Pro Tyr Leu Glu Lys Leu Gly Phe Gly
                485                 490                 495

Val Thr Ala Tyr Gly Cys Thr Thr Cys Ile Gly Asn Ala Gly Asp Leu
            500                 505                 510

Thr Pro Glu Leu Asn Glu Ala Ile Thr Arg Asn Asp Leu Val Ala Ala
        515                 520                 525

Ala Val Leu Ser Gly Asn Arg Asn Phe Glu Ala Arg Ile His Pro Asn
    530                 535                 540

Ile Arg Ala Asn Phe Leu Ala Ser Pro Pro Leu Val Ala Tyr Ala
545                 550                 555                 560

Ile Ala Gly Asn Val Thr Arg Asp Leu Met Thr Glu Pro Val Gly Lys
                565                 570                 575

Gly Lys Lys Gly Arg Asp Ile Tyr Leu Gly Asp Ile Trp Pro Thr Ser
            580                 585                 590

Glu Glu Ile His Ala Leu Met Lys Tyr Ala Met Asp Ala Lys Thr Phe
        595                 600                 605

Lys Gly Asn Tyr Glu Gln Val Lys Lys Pro Ser Lys Leu Trp Ala Gly
    610                 615                 620

Ile Lys Gly Thr Lys Gly Gln Val Tyr Asp Trp Pro Lys Ser Thr Tyr
625                 630                 635                 640

Ile Ala Glu Pro Pro Phe Phe Gln Asp Phe Ser Met Gln Pro Ala Ala
                645                 650                 655

Thr Ser Ala Ser Val Arg Gly Ala Arg Ala Leu Gly Ile Phe Gly Asp
            660                 665                 670

Ser Val Thr Thr Asp His Ile Ser Pro Ala Gly Ser Ile Lys Asp Thr
        675                 680                 685

Ser Pro Ala Gly Lys Tyr Leu Leu Ser His Gly Val Leu Lys Ala Asp
    690                 695                 700

Phe Asn Ser Tyr Gly Ser Arg Arg Gly Asn His Glu Val Met Met Arg
705                 710                 715                 720

Gly Thr Phe Ala Asn Val Arg Ile Lys Asn Leu Met Ile Pro Pro Lys
                725                 730                 735

Ala Asp Gly Ser Arg Val Glu Gly Gly Ile Thr Leu His Gln Pro Thr
            740                 745                 750

Gly Asp Glu Met Ser Ile Tyr Asp Ala Ala Met Lys Tyr Val Ala Glu
        755                 760                 765

Gly Thr Pro Thr Val Val Phe Gly Gly Glu Glu Tyr Gly Thr Gly Ser
    770                 775                 780

Ser Arg Asp Trp Ala Ala Lys Gly Thr Gln Leu Leu Gly Val Lys Ala
785                 790                 795                 800

Val Val Ala Arg Ser Phe Glu Arg Ile His Arg Ser Asn Leu Val Gly
                805                 810                 815

Met Gly Val Leu Pro Leu Gln Phe Lys Gly Asn Asp Ser Ala Gln Thr
            820                 825                 830

Leu Gly Ile Thr Gly Asn Glu Thr Phe Asp Ile Glu Gly Ile Glu Gly
        835                 840                 845

Asp Leu Lys Pro Gln Gln Asp Val Val Leu Ile His Arg Ala Asn
    850                 855                 860

Gly Asp Val Gln Arg Val Pro Val Leu Leu Arg Ile Asp Thr Pro Ile
865                 870                 875                 880

Glu Val Asp Tyr Tyr Asn His Gly Gly Ile Leu Pro Phe Val Leu Arg
            885                 890                 895

Gln Leu Leu Ala Ala
        900

<210> SEQ ID NO 9
<211> LENGTH: 2706
<212> TYPE: DNA
<213> ORGANISM: Artificial sequence
<220> FEATURE:
<223> OTHER INFORMATION: Synthetic

<400> SEQUENCE: 9

| | | | | | |
|---|---|---|---|---|---|
| atgccacata | atctgaaaaa | cacactcaaa | gaatttaaga | tcggcagctc | cggcaagggc | 60 |
| cagtactatt | ccctccctca | gctgggcgag | gagctcgacg | tcgcggtggg | tcgcctgccc | 120 |
| gtgagcatcc | gggtggtcct | ggaatcggtg | ctgcgcaact | gcgacggcaa | gaaggtcacg | 180 |
| gaggagcacg | tgcgccagct | ggcgaattgg | aagcccaacg | ccgaacgggt | ggacgagatc | 240 |
| ccgttcgtgg | tcgcccgcgt | ggtcctgcaa | gacttcacag | gcgtgccgct | cctggcggat | 300 |
| ttggcggcca | tgcgcaacgt | ggccgagaag | atgggcaaga | cccgaagaa | gatcgagccg | 360 |
| ctggtcccgg | tggacctggt | cgtggatcat | agcgtccagg | tggaccactt | cgtgagaag | 420 |
| aaggccctgg | acctgaacat | gcagctggag | ttccagcgca | ataacgaacg | ctaccagttc | 480 |
| atgaagtggg | gcatgcaagc | gttcgacacg | ttcggcgtgg | tccagccggg | ttttggcatc | 540 |
| gtccaccagg | tcaacctgga | gtatctcgcc | cgtggcgtcc | acaagaaaga | cggcgtctac | 600 |
| tacccggaca | ccctggtcgg | caccgactcg | cacacgacca | tgatcaacgg | gatcggcgtg | 660 |
| gtgggctggg | gcgtgggcgg | catcgaggcc | gaagcgggga | tgctgggcca | accggtgtac | 720 |
| tttctcaccc | cggatgtcgt | cggcgtcgag | ctgaagggtc | ggctgcgcga | aggcgtgacc | 780 |
| gcgaccgacc | tggtcctgac | cattacggaa | atgctccgca | aggaaaaagt | ggtgggcaag | 840 |
| ttcgtcgagt | tcttcggtga | aggcaccgcc | tcgttggcgc | tgcccgatcg | ggcgaccatc | 900 |
| gggaacatgg | cgccggaata | tggggccacg | atgggcttct | ttcccgtgga | tgagaaaacc | 960 |
| atcgattact | tcaagggcac | agggcgcacc | gaagaggaaa | tcgccgcgtt | cgaaggctat | 1020 |
| ttccgtgccc | agaaaatgtt | cggcatcccc | cgtgcgggcg | agatcgacta | cagcaaggtg | 1080 |
| gtgacactgg | acctcggcac | cgtcgcgccg | tcgctggccg | ggccgaagcg | cccccaggac | 1140 |
| cggatcgaga | tcggcaatgt | gaagtcgacc | tttgccagcc | tgttctcgaa | gcccgtggcc | 1200 |
| gaaaacggtt | tcaacaaaga | gcggcggac | ctggatcgcg | cctatacgac | caccgacggc | 1260 |
| ctggaggtga | agaatggcga | cgtgctgatc | gcggccatca | cgtcgtgcac | aaacaccagc | 1320 |
| aacccgtccg | tgctgctggg | tgccggcctg | ttggccaaaa | aggcagtgga | agccgggctc | 1380 |
| accgtggcgc | cacacatcaa | gaccagcttg | gcgccgggtt | cccgcgtcgt | gactgagtac | 1440 |
| ctcaccgccg | caggcctgct | gccgtatctc | gaaaagctgg | gcttcggcgt | cacggcctac | 1500 |
| ggttgcacca | cttgcatcgg | caacgccggc | gacctgaccc | ccgagctgaa | cgaagcaatc | 1560 |
| acgcgcaacg | acctggtggc | agccgccgtc | ctgtcgggca | accgcaactt | cgaagcccgc | 1620 |
| atccacccga | catccgggc | gaacttcctg | gcctccccgc | cattggtcgt | ggcgtacgcc | 1680 |
| atcgcgggca | acgtcacgcg | tgacctgatg | acggaaccgg | tgggcaaggg | caagaagggc | 1740 |
| cgcgacatct | acctgggcga | tatctggccc | acgtccgaag | aaattcacgc | gctgatgaaa | 1800 |
| tatgcgatga | tgccaagac | gttcaagggc | aactacgaac | aggtgaagaa | gcctagcaag | 1860 |
| ctgtgggcag | gcattaaggg | caccaagggc | caggtgtacg | actggcccaa | gtcgacctac | 1920 |

```
atcgccgagc cgccgttttt ccaagatttc agcatgcagc ccgcggcgac ctcggcctcg    1980
gtgcgcggtg cacgcgccct gggtatcttc ggcgatagcg tcactactga ccacatctcc    2040
cctgcggggt cgatcaagga cacgagcccc gcaggcaagt atctcctgtc gcatggcgtg    2100
ctgaaggccg acttcaactc ctacggctcc cgccgtggta accatgaagt catgatgcgg    2160
ggcaccttcg cgaatgtccg cattaagaac ctgatgatcc ccccgaaggc cgacggcagc    2220
cgtgtggagg gcggcatcac gctgcaccag ccgacgggtg acgaaatgtc gatctatgac    2280
gccgccatga agtacgtggc cgagggcacc ccgaccgtcg tgttcggggg cgaagagtac    2340
gggacgggca gcagccgcga ctgggcagcc aagggcaccc agctgctggg cgtgaaggca    2400
gtggtggcgc gcagcttcga gcgcatccac cgctcgaact tggtgggtat gggcgtgctg    2460
ccgctgcagt tcaagggcaa cgactcggcc caaacgctgg gcatcacggg caatgaaacc    2520
ttcgacatcg agggcatcga gggcgacctg aagccgcagc aagacgtggt gctggtcatc    2580
caccgcgcga acgcgacgt ccagcgcgtg ccggtgctgc tgcggatcga caccccgatt    2640
gaagtggact attacaacca cggcggcatc ctcccgttcg tcctgcgcca gttgctggcc    2700
gcgtga                                                               2706
```

<210> SEQ ID NO 10
<211> LENGTH: 863
<212> TYPE: PRT
<213> ORGANISM: C. necator

<400> SEQUENCE: 10

```
Met Leu Glu Asn Tyr Arg Ala His Val Ala Glu Arg Ala Ala Leu Gly
1               5                   10                  15

Ile Pro Pro Leu Pro Leu Thr Ala Lys Gln Thr Ala Glu Leu Val Glu
            20                  25                  30

Leu Leu Lys Asn Pro Pro Ala Gly Glu Glu Gln Thr Leu Val Glu Leu
        35                  40                  45

Ile Thr Tyr Arg Val Pro Ala Gly Val Asp Asp Ala Ala Lys Val Lys
    50                  55                  60

Ala Ser Tyr Leu Ala Ala Val Ala Leu Gly Lys Glu Lys Cys Ala Leu
65                  70                  75                  80

Ile Ser Arg Ala Lys Ala Thr Glu Leu Leu Gly Thr Met Leu Gly Gly
            85                  90                  95

Tyr Asn Ile Ser Pro Leu Ile Glu Leu Leu Asp Asp Ala Glu Val Gly
            100                 105                 110

Thr Val Ala Ala Glu Ala Leu Lys Lys Thr Leu Leu Met Phe Asp Ala
        115                 120                 125

Phe His Asp Val Lys Glu Lys Ala Asp Gln Gly Asn Ala Asn Ala Lys
    130                 135                 140

Ala Val Leu Gln Ser Trp Ala Asp Ala Glu Trp Phe Thr Ser Arg Pro
145                 150                 155                 160

Glu Val Pro Gln Ser Leu Thr Ile Thr Val Phe Lys Val Pro Gly Glu
                165                 170                 175

Thr Asn Thr Asp Asp Leu Ser Pro Ala Pro Asp Ala Thr Thr Arg Pro
            180                 185                 190

Asp Ile Pro Met His Ala Leu Ala Met Leu Lys Asn Lys Arg Glu Gly
        195                 200                 205

Ala Ala Phe Gln Pro Glu Glu Asp Gly Lys Arg Gly Pro Val Lys Phe
    210                 215                 220
```

```
Ile Glu Ser Leu Lys Glu Lys Gly His Leu Val Ala Tyr Val Gly Asp
225                 230                 235                 240

Val Val Gly Thr Gly Ser Ser Arg Lys Ser Ala Thr Asn Ser Val Leu
            245                 250                 255

Trp Phe Thr Gly Glu Asp Ile Pro Phe Ile Pro Asn Lys Arg Phe Gly
        260                 265                 270

Gly Val Cys Leu Gly Asn Lys Ile Ala Pro Ile Phe Tyr Asn Thr Met
        275                 280                 285

Glu Asp Ala Gly Ala Leu Pro Ile Glu Leu Asp Val Ser Lys Met Glu
    290                 295                 300

Met Gly Asp Val Val Glu Leu Arg Pro Tyr Glu Gly Lys Ala Leu Lys
305                 310                 315                 320

Asp Gly Ala Val Ile Ala Glu Phe Lys Val Lys Ser Asp Val Leu Phe
                325                 330                 335

Asp Glu Val Arg Ala Gly Gly Arg Ile Pro Leu Ile Val Gly Arg Gly
            340                 345                 350

Leu Thr Ala Lys Ala Arg Glu Ala Leu Gly Leu Ala Pro Ser Thr Leu
        355                 360                 365

Phe Arg Leu Pro Gln Asn Pro Ala Asp Thr Gly Arg Gly Phe Thr Leu
    370                 375                 380

Ala Gln Lys Met Val Gly Arg Ala Cys Gly Leu Pro Glu Gly Lys Gly
385                 390                 395                 400

Ile Arg Pro Gly Thr Tyr Cys Glu Pro Lys Met Thr Ser Val Gly Ser
                405                 410                 415

Gln Asp Thr Thr Gly Pro Met Thr Arg Asp Glu Leu Lys Asp Leu Ala
            420                 425                 430

Cys Leu Gly Phe Ser Ala Asp Leu Val Met Gln Ser Phe Cys His Thr
        435                 440                 445

Ala Ala Tyr Pro Lys Pro Val Asp Val Lys Thr His His Thr Leu Pro
    450                 455                 460

Glu Phe Ile Ser Thr Arg Gly Gly Ile Ser Leu Arg Pro Gly Asp Gly
465                 470                 475                 480

Val Ile His Ser Trp Leu Asn Arg Met Leu Leu Pro Asp Thr Val Gly
                485                 490                 495

Thr Gly Gly Asp Ser His Thr Arg Phe Pro Ile Gly Ile Ser Phe Pro
            500                 505                 510

Ala Gly Ser Gly Leu Val Ala Phe Ala Ala Ala Thr Gly Val Met Pro
        515                 520                 525

Leu Asp Met Pro Glu Ser Val Leu Val Arg Phe Lys Gly Lys Met Gln
    530                 535                 540

Pro Gly Val Thr Leu Arg Asp Leu Val Asn Ala Ile Pro Leu Tyr Ala
545                 550                 555                 560

Ile Lys Gln Gly Leu Leu Thr Val Ala Lys Gln Gly Lys Lys Asn Ile
                565                 570                 575

Phe Ser Gly Arg Val Leu Glu Ile Glu Gly Leu Pro Asp Leu Lys Val
            580                 585                 590

Glu Gln Ala Phe Glu Leu Ser Asp Ala Ser Ala Glu Arg Ser Ala Ala
        595                 600                 605

Gly Cys Thr Val Arg Leu Asn Lys Asp Pro Ile Ile Glu Tyr Ile Asn
    610                 615                 620

Ser Asn Ile Thr Leu Leu Lys Trp Met Ile Ala Gln Gly Tyr Gln Asp
625                 630                 635                 640

Pro Arg Ser Leu Gln Arg Arg Ile Lys Ala Met Glu Ala Trp Leu Ala
```

```
            645                 650                 655
Asp Pro Lys Leu Leu Glu Pro Asp Ala Asp Ala Glu Tyr Ala Ala Val
            660                 665                 670

Ile Glu Ile Asp Leu Ala Asp Val His Glu Pro Ile Val Ala Cys Pro
            675                 680                 685

Asn Asp Pro Asp Asp Val Lys Thr Leu Ser Glu Val Ala Gly Ala Lys
            690                 695                 700

Ile Asp Glu Val Phe Ile Gly Ser Cys Met Thr Asn Ile Gly His Phe
705                 710                 715                 720

Arg Ala Ala Ser Lys Leu Leu Glu Gly Lys Arg Asp Ile Pro Val Lys
                725                 730                 735

Leu Trp Val Ala Pro Pro Thr Lys Met Asp Gln Lys Gln Leu Thr Glu
            740                 745                 750

Glu Gly His Tyr Gly Val Phe Gly Thr Ala Gly Ala Arg Thr Glu Met
            755                 760                 765

Pro Gly Cys Ser Leu Cys Met Gly Asn Gln Ala Gln Val Arg Glu Gly
            770                 775                 780

Ala Thr Val Met Ser Thr Ser Thr Arg Asn Phe Pro Asn Arg Leu Gly
785                 790                 795                 800

Lys Asn Thr Asn Val Tyr Leu Gly Ser Ala Glu Leu Ala Ala Ile Cys
                805                 810                 815

Ser Arg Leu Gly Arg Ile Pro Thr Lys Glu Tyr Met Ala Asp Met
                820                 825                 830

Gly Val Leu Asn Ala Asn Gly Asp Lys Ile Tyr Lys Tyr Met Asn Phe
            835                 840                 845

Asp Gln Ile Glu Asp Phe Lys Glu Val Ala Asp Gly Val Thr Val
            850                 855                 860

<210> SEQ ID NO 11
<211> LENGTH: 2592
<212> TYPE: DNA
<213> ORGANISM: Artificial sequence
<220> FEATURE:
<223> OTHER INFORMATION: Synthetic

<400> SEQUENCE: 11
atgttggaaa attatagagc acacgtcgca gaaagggcag cactgggcat tccaccgctc      60
ccgctgacgg ccaagcaaac cgccgagctg gtcgaactcc tgaagaaccc tcccgcgggc     120
gaggaacaga ccctggtcga gctcatcacc taccgcgtgc cggcgggcgt ggacgacgcc     180
gcgaaggtca aggcctccta cctggcagcg gtggcgctcg gcaaggagaa atgcgccctg     240
atcagccgtg cgaaggcgac cgaactgctg ggtaccatgc tgggcggcta taacatcagc     300
ccactgatcg agctgctgga tgacgccgaa gtggggactg tcgccgccga ggcactcaag     360
aaaacgctct tgatgttcga cgccttccac gacgtcaagg aaaaggccga tcaaggcaac     420
gccaacgcga aggcagtgct gcagtcgtgg gcggatgcag aatggttcac cagccgtccc     480
gaagtgccgc agagcctgac catcaccgtg ttcaaggtcc aggcgaaaac caacaccgac     540
gacctgagcc ccgccccgga cgcaaccacc cgccccgata tccccatgca tgccctggcc     600
atgctgaaga caagcgcga aggcgccgcg ttccagccgg aagaggacgg caagcggggc     660
cccgtgaagt tcatcgagag cctcaaggaa aagggccatc tcgtggcgta cgtcggtgat     720
gtggtcggca ccggctcgtc ccgcaagtcg gccaccaact cggtcctgtg gttcaccggc     780
gaggacatcc cgttcatccc taataagcgc ttcggggcgc tctgcctggg caataagatc     840
```

| | |
|---|---:|
| gcaccgatct tttacaacac gatggaggac gccggggccc tgccgatcga gctggatgtg | 900 |
| tcgaagatgg agatgggtga tgtcgtggaa ctgcggccgt acgagggaa ggccctcaag | 960 |
| gacggcgccg tgatcgccga gttcaaggtc aagtcggatg tcctgttcga cgaagtgcgc | 1020 |
| gccggggtc gcatcccact gattgtgggt cgcggcctga ccgccaaggc ccgtgaggcc | 1080 |
| ctgggcctcg ccccgtccac actgttccgc ctgccgcaga accccgccga caccggtcgc | 1140 |
| ggcttcaccc tggcgcagaa gatggtgggc cgtgcctgcg ggttccgga aggcaagggc | 1200 |
| atccgccccg gcacctactg cgagccgaag atgaccagcg tcggcagcca agatacaacc | 1260 |
| ggcccgatga ctcgcgacga actgaaggac ctggcgtgcc tgggcttctc cgcagacctg | 1320 |
| gtgatgcagt cgttctgcca cacggccgca tacccaaagc cagtcgacgt caagacccat | 1380 |
| cacacgctgc cggagttcat ctccacccgc ggtggcatct ccctccgccc gggcgacggc | 1440 |
| gtgatccact cctggctcaa tcgcatgctg ctgccggaca cggtcggtac cggcggcgac | 1500 |
| agccacaccc gcttcccgat cggcatcagc ttccccgcgg gctcgggcct ggtggcgttt | 1560 |
| gccgcagcga ccggcgtgat gccgctggac atgccgaaaa gcgtcctggt gcggtttaag | 1620 |
| ggcaagatgc agcccggcgt gacccteegc gacctggtga acgccatccc gctgtacgcc | 1680 |
| atcaagcagg gcctcctgac cgtggcgaag cagggcaaga gaacatcttc tcgggccgc | 1740 |
| gtcctggaga tcgagggcct gcccgacctc aaggtggagc aagccttcga gctctcggac | 1800 |
| gcatcggcg agcggagcgc ggccggttgc accgtccgcc tgaacaaaga cccgatcatc | 1860 |
| gagtatatca acagcaatat cacgctgctg aagtggatga tcgcccaagg ctaccaggac | 1920 |
| ccgcgctcgc tgcagcggcg cattaaggca atggaagcct ggctggcaga cccgaagctg | 1980 |
| ctggaacccg acgccgacgc ggagtacgcg gccgtgatcg aaatcgatct cgccgacgtg | 2040 |
| catgagccta tcgtggcctg cccgaacgac ccggacgatg tgaaaacgct gtcggaagtc | 2100 |
| gcgggcgcca agatcgacga agtgttcatc ggcagctgca tgaccaatat cggccacttt | 2160 |
| cgtgccgcct cgaagttgct ggaaggcaag gcgacatcc cggtgaagct gtgggtcgcg | 2220 |
| cctcccacga aaatggatca gaagcagctg actgaggagg gccactacgg cgtgttcggc | 2280 |
| acggcgggcg cgcggacaga gatgccgggc tgcagcctgt gcatgggcaa ccaggcccag | 2340 |
| gtccgcgaag gcgcgaccgt gatgagcacg tcgacgcgga atttccctaa ccgcctgggc | 2400 |
| aagaacacca acgtgtacct cggctcggcg gagttggccg cgatctgctc ccgcctgggc | 2460 |
| cgcatcccca ccaaagaaga gtacatggcc gacatgggcg tgctcaacgc caacggcgac | 2520 |
| aagatttaca agtacatgaa cttcgatcag atcgaggact tcaaggaagt cgccgacggc | 2580 |
| gtcacagtgt ga | 2592 |

<210> SEQ ID NO 12
<211> LENGTH: 1203
<212> TYPE: DNA
<213> ORGANISM: Artificial sequence
<220> FEATURE:
<223> OTHER INFORMATION: Synthetic

<400> SEQUENCE: 12

| | |
|---|---:|
| atgcttgcgc tacaaggaat tcgcgtgctg gacctgagca aggtgctggc cggcccgctg | 60 |
| tgcggccagt atctggggga actcggcgcc gacgtcgtca aggtcgagcc gatcggcgtg | 120 |
| ggggacgata cccgcgcctg gctgccgcag gagcagggcc agtcggcaac cttcctttcg | 180 |
| gtcaaccaca caagcgcag catcgcggtc gacctcaaga ccgccgaggg acagcagctc | 240 |
| gtgcagaccc tggccgccgg cgcggacatc gtgctgcagg gcttcggcgg aggcaccgcg | 300 |

```
gcccggctgg gcgtggacca tgacagcctg agcgcgcgca atccccgcct gatctactgc    360
gagatctccg gctatggccg caccggcccg ctcggcaacg agcccggcta tgacgtcatg    420
ctgcaggcgt tcagcggcat gattagcacc atgggcgatc cggcaggcaa gctggcgcgc    480
gccagtttct ctccggtcga cctgggcacg ggcatgcatg ccttcagcgg catcctggcc    540
gcgttgatcg aacgcgaaaa gacccgggcac ggcgtctacc tggaggtctc gctgctcgat    600
accgcgctcg gcttcatggg ctacatggcg cagaactact ggcgcaccgg ccgggcgccg    660
gcgcgcatgg ggaccgcgca ccccgccatg gccccgtacc aggccttcga tgcagcggat    720
ggcccgctca tgatcggcgt cggcaacgat gcccagtggc gccgcttctg cacggtcgcc    780
gggctgcacg accacgtcga cgaccccgcg ttcgccacca tgcggcgcg cgtggccaac    840 ttcgcgcgca ccgtggacct cgtgcagcgc cgcatcgcca cgcagccggt cgcattctgg    900
ctgcaggcat tgcgcgcggc aggcgtggcc tgctcgccca tccacacact cgaccaggcc    960
cttgcccacc cgcagctgga ggcgcggcag ctggtggtcg aatcggaaca cccggtgctg   1020
ggcacggtcc ggaacatggg tttgccggtg cggtttcgcg acggcaagcg gcaggcgcac   1080
cgcgcgccgc ccctgctggg gcagcacacc gaggaaattc tgcgcgaggc aggctttggc   1140
cccgacatga tccggcgcta ccaggccgac ggcatcgtgg cggtcgccgg atccgtcacg   1200
tag                                                                  1203
```

<210> SEQ ID NO 13
<211> LENGTH: 400
<212> TYPE: PRT
<213> ORGANISM: Artificial sequence
<220> FEATURE:
<223> OTHER INFORMATION: Synthetic

<400> SEQUENCE: 13

```
Met Leu Ala Leu Gln Gly Ile Arg Val Leu Asp Leu Ser Lys Val Leu
1               5                   10                  15

Ala Gly Pro Leu Cys Gly Gln Tyr Leu Gly Glu Leu Gly Ala Asp Val
                20                  25                  30

Val Lys Val Glu Pro Ile Gly Val Gly Asp Asp Thr Arg Ala Trp Leu
            35                  40                  45

Pro Gln Glu Gln Gly Gln Ser Ala Thr Phe Leu Ser Val Asn His Asn
        50                  55                  60

Lys Arg Ser Ile Ala Val Asp Leu Lys Thr Ala Glu Gly Gln Gln Leu
65                  70                  75                  80

Val Gln Thr Leu Ala Ala Gly Ala Asp Ile Val Leu Gln Gly Phe Gly
                85                  90                  95

Gly Gly Thr Ala Ala Arg Leu Gly Val Asp His Asp Ser Leu Ser Ala
                100                 105                 110

Arg Asn Pro Arg Leu Ile Tyr Cys Glu Ile Ser Gly Tyr Gly Arg Thr
            115                 120                 125

Gly Pro Leu Gly Asn Glu Pro Gly Tyr Asp Val Met Leu Gln Ala Phe
        130                 135                 140

Ser Gly Met Ile Ser Thr Met Gly Asp Pro Ala Gly Lys Leu Ala Arg
145                 150                 155                 160

Ala Ser Phe Ser Pro Val Asp Leu Gly Thr Gly Met His Ala Phe Ser
                165                 170                 175

Gly Ile Leu Ala Ala Leu Ile Glu Arg Glu Lys Thr Gly His Gly Val
                180                 185                 190
```

```
Tyr Leu Glu Val Ser Leu Leu Asp Thr Ala Leu Gly Phe Met Gly Tyr
            195                 200                 205
Met Ala Gln Asn Tyr Trp Arg Thr Gly Arg Ala Pro Ala Arg Met Gly
        210                 215                 220
Thr Ala His Pro Ala Met Ala Pro Tyr Gln Ala Phe Asp Ala Ala Asp
225                 230                 235                 240
Gly Pro Leu Met Ile Gly Val Gly Asn Asp Ala Gln Trp Arg Arg Phe
                245                 250                 255
Cys Thr Val Ala Gly Leu His Asp His Val Asp Asp Pro Ala Phe Ala
            260                 265                 270
Thr Asn Ala Ala Arg Val Ala Asn Phe Ala Arg Thr Val Asp Leu Val
        275                 280                 285
Gln Arg Arg Ile Ala Thr Gln Pro Val Ala Phe Trp Leu Gln Ala Leu
290                 295                 300
Arg Ala Ala Gly Val Ala Cys Ser Pro Ile His Thr Leu Asp Gln Ala
305                 310                 315                 320
Leu Ala His Pro Gln Leu Glu Ala Arg Gln Leu Val Val Glu Ser Glu
                325                 330                 335
His Pro Val Leu Gly Thr Val Arg Asn Met Gly Leu Pro Val Arg Phe
            340                 345                 350
Arg Asp Gly Lys Arg Gln Ala His Arg Ala Pro Pro Leu Leu Gly Gln
        355                 360                 365
His Thr Glu Glu Ile Leu Arg Glu Ala Gly Phe Gly Pro Asp Met Ile
370                 375                 380
Arg Arg Tyr Gln Ala Asp Gly Ile Val Ala Val Ala Gly Ser Val Thr
385                 390                 395                 400
```

<210> SEQ ID NO 14
<211> LENGTH: 1167
<212> TYPE: DNA
<213> ORGANISM: Artificial sequence
<220> FEATURE:
<223> OTHER INFORMATION: Synthetic

<400> SEQUENCE: 14

| | | | | | |
|---|---|---|---|---|---|
| atgaatatcc | atgagtatca | aggcaaggaa | atcctgcgca | aatacaatgt | gccggttccg | 60 |
| cgcggcatcc | ccgcgttctc | ggttgacgag | gccctgaagg | ccgcagaaac | gctcggcggc | 120 |
| ccggtgtggg | tcgtcaaggc | tcagattcat | gcgggtggcc | gcggcaaggg | cggcggcgtg | 180 |
| aaggttgcca | agagcatcga | cgacgtcaag | acctacgctt | cgaacatcct | gggcatgcag | 240 |
| ctggtcacgc | accagaccgg | cccggaaggc | aagaaggtca | accgtctgct | gatcgaagaa | 300 |
| ggcgccgaca | tcaagaagga | actgtacgtt | tcgctggtgg | tggaccgtgt | ttcgcagaag | 360 |
| gtcgcgctga | tggcctcgag | cgaaggcggc | atggacatcg | aagaagtcgc | cgcccacagc | 420 |
| ccggaaaaga | tccacaccct | gatcatcgag | ccgtcggttg | gcctgaccga | cgctgaagcc | 480 |
| gacgacatcg | cccgcaagat | cggcgtgccc | gacacgagcg | tggcgcaagc | cgccaggcc | 540 |
| ctgcaaggcc | tgtacaaggc | gttctatgaa | accgacgctt | cgctggctga | aatcaacccg | 600 |
| ctgatcctga | ccggcgacgg | caaggtcatc | gcgctggacg | ccaagttcaa | cttcgactcg | 660 |
| aacgcgctgt | tccgtcaccc | ggaaatcgtt | gcctaccgcg | acctggatga | agaagacgcc | 720 |
| aacgaaatcg | aagcctcgaa | gttcgacctg | gcctacatct | cgctggacgg | caacatcggc | 780 |
| tgcctggtga | acggcgccgg | cctggccatg | gccaccatgg | acaccatcaa | gctgttcggc | 840 |
| ggcgagccgg | ccaacttcct | cgacgtgggc | ggcggtgcca | ccaccgagaa | ggtgaccgaa | 900 |

```
gccttcaagc tgatgctgag caacaagaac gtgcaggcca tcctggtcaa catcttcggc    960
ggcatcatgc gttgcgacgt gatcgccgaa ggcgtgatct ccgcttccaa ggccgtgcac   1020
ctgacggtgc cgctggtcgt gcgcatgaag ggcaccaacg aagacctcgg caagaagatg   1080
ctggccgact cgggcctgcc catcatctcg ccgacacga tggaagaagc cgcccagaag    1140
gtggtggccg ctgccgctgg caagtaa                                       1167
```

<210> SEQ ID NO 15
<211> LENGTH: 388
<212> TYPE: PRT
<213> ORGANISM: Artificial sequence
<220> FEATURE:
<223> OTHER INFORMATION: Synthetic

<400> SEQUENCE: 15

```
Met Asn Ile His Glu Tyr Gln Gly Lys Glu Ile Leu Arg Lys Tyr Asn
1               5                   10                  15

Val Pro Val Pro Arg Gly Ile Pro Ala Phe Ser Val Asp Glu Ala Leu
            20                  25                  30

Lys Ala Glu Thr Leu Gly Gly Pro Val Trp Val Lys Ala Gln
        35                  40                  45

Ile His Ala Gly Gly Arg Gly Lys Gly Gly Val Lys Val Ala Lys
    50                  55                  60

Ser Ile Asp Asp Val Lys Thr Tyr Ala Ser Asn Ile Leu Gly Met Gln
65                  70                  75                  80

Leu Val Thr His Gln Thr Gly Pro Glu Gly Lys Lys Val Asn Arg Leu
                85                  90                  95

Leu Ile Glu Glu Gly Ala Asp Ile Lys Lys Glu Leu Tyr Val Ser Leu
            100                 105                 110

Val Val Asp Arg Val Ser Gln Lys Val Ala Leu Met Ala Ser Ser Glu
        115                 120                 125

Gly Gly Met Asp Ile Glu Glu Val Ala Ala His Ser Pro Glu Lys Ile
    130                 135                 140

His Thr Leu Ile Ile Glu Pro Ser Val Gly Leu Thr Asp Ala Glu Ala
145                 150                 155                 160

Asp Asp Ile Ala Arg Lys Ile Gly Val Pro Asp Thr Ser Val Ala Gln
                165                 170                 175

Ala Arg Gln Ala Leu Gln Gly Leu Tyr Lys Ala Phe Tyr Glu Thr Asp
            180                 185                 190

Ala Ser Leu Ala Glu Ile Asn Pro Leu Ile Leu Thr Gly Asp Gly Lys
        195                 200                 205

Val Ile Ala Leu Asp Ala Lys Phe Asn Phe Asp Ser Asn Ala Leu Phe
    210                 215                 220

Arg His Pro Glu Ile Val Ala Tyr Arg Asp Leu Asp Glu Glu Asp Ala
225                 230                 235                 240

Asn Glu Ile Glu Ala Ser Lys Phe Asp Leu Ala Tyr Ile Ser Leu Asp
                245                 250                 255

Gly Asn Ile Gly Cys Leu Val Asn Gly Ala Gly Leu Ala Met Ala Thr
            260                 265                 270

Met Asp Thr Ile Lys Leu Phe Gly Gly Glu Pro Ala Asn Phe Leu Asp
        275                 280                 285

Val Gly Gly Gly Ala Thr Thr Glu Lys Val Thr Glu Ala Phe Lys Leu
    290                 295                 300

Met Leu Ser Asn Lys Asn Val Gln Ala Ile Leu Val Asn Ile Phe Gly
305                 310                 315                 320
```

```
Gly Ile Met Arg Cys Asp Val Ile Ala Glu Gly Val Ile Ser Ala Ser
                325                 330                 335

Lys Ala Val His Leu Thr Val Pro Leu Val Val Arg Met Lys Gly Thr
            340                 345                 350

Asn Glu Asp Leu Gly Lys Lys Met Leu Ala Asp Ser Gly Leu Pro Ile
        355                 360                 365

Ile Ser Ala Asp Thr Met Glu Glu Ala Ala Gln Lys Val Val Ala Ala
    370                 375                 380

Ala Ala Gly Lys
385
```

<210> SEQ ID NO 16
<211> LENGTH: 882
<212> TYPE: DNA
<213> ORGANISM: Artificial sequence
<220> FEATURE:
<223> OTHER INFORMATION: Synthetic

<400> SEQUENCE: 16

```
atgtcgattc tgatcaacaa agacaccaag gtcatcaccc agggcatcac cggcaagacc        60
ggccagttcc acacccgtgg ctgccgcgac tacgccaacg gcaagaactg cttcgtcgcg       120
ggcgtgaacc cgaagaaggc cggtgaagac ttcgaaggca ttcccatcta cgccagcgtc       180
aaggacgcca aggctcagac cggcgccacc gtgtcggtca tctacgtgcc gcctgcaggc       240
gccgctgccg cgatctggga agccgttgac gccgacctgg acctggtggt ctgcattacc       300
gaaggcatcc ccgtgcgcga catgatggaa gtcaaggacc gcatgcgccg cgagaagaag       360
aagaccctgc tgctgggacc gaactgcccg ggcctgatca cgccggacga aatcaagatc       420
ggcatcatgc cgggccatat ccacaagaag ggccgcatcg cgtggtgtc gcgctcgggc        480
acgctgacgt acgaagccgt gggccagctg accgcgctgg gcctgggcca gtcgtcggct       540
gtcggcatcg gtggcgaccc catcaacggc ctgaagcaca tcgacgtgat gaagatgttc       600
aacgacgatc cggaaacgga cgccgtggtc atgatcggtg agatcggtgg tccggacgaa       660
gccaacgcgg cttactggat caaggaaaac atgaagaagc cggtggttgg cttcatcgct       720
ggcgtgaccg cgcctccggg caagcgcatg ggccacgccg cgcgcgctga tctcgggcggt       780
gccgataccg cccaggccaa gctggaaatc atggaagcct gcggtatcaa ggtgaccaag       840
aacccgtcgg agatgggccg cctgctgaag gcaatgctgt aa                         882
```

<210> SEQ ID NO 17
<211> LENGTH: 293
<212> TYPE: PRT
<213> ORGANISM: Artificial sequence
<220> FEATURE:
<223> OTHER INFORMATION: Synthetic

<400> SEQUENCE: 17

```
Met Ser Ile Leu Ile Asn Lys Asp Thr Lys Val Ile Thr Gln Gly Ile
1               5                   10                  15

Thr Gly Lys Thr Gly Gln Phe His Thr Arg Gly Cys Arg Asp Tyr Ala
            20                  25                  30

Asn Gly Lys Asn Cys Phe Val Ala Gly Val Asn Pro Lys Lys Ala Gly
        35                  40                  45

Glu Asp Phe Glu Gly Ile Pro Ile Tyr Ala Ser Val Lys Asp Ala Lys
    50                  55                  60

Ala Gln Thr Gly Ala Thr Val Ser Val Ile Tyr Val Pro Pro Ala Gly
```

```
                65                  70                  75                  80
Ala Ala Ala Ala Ile Trp Glu Ala Val Asp Ala Asp Leu Asp Leu Val
                    85                  90                  95

Val Cys Ile Thr Glu Gly Ile Pro Val Arg Asp Met Met Glu Val Lys
                100                 105                 110

Asp Arg Met Arg Arg Glu Lys Lys Lys Thr Leu Leu Leu Gly Pro Asn
                115                 120                 125

Cys Pro Gly Leu Ile Thr Pro Asp Glu Ile Lys Ile Gly Ile Met Pro
    130                 135                 140

Gly His Ile His Lys Lys Gly Arg Ile Gly Val Val Ser Arg Ser Gly
145                 150                 155                 160

Thr Leu Thr Tyr Glu Ala Val Gly Gln Leu Thr Ala Leu Gly Leu Gly
                165                 170                 175

Gln Ser Ser Ala Val Gly Ile Gly Gly Asp Pro Ile Asn Gly Leu Lys
                180                 185                 190

His Ile Asp Val Met Lys Met Phe Asn Asp Asp Pro Glu Thr Asp Ala
                195                 200                 205

Val Val Met Ile Gly Glu Ile Gly Gly Pro Asp Glu Ala Asn Ala Ala
            210                 215                 220

Tyr Trp Ile Lys Glu Asn Met Lys Lys Pro Val Val Gly Phe Ile Ala
225                 230                 235                 240

Gly Val Thr Ala Pro Pro Gly Lys Arg Met Gly His Ala Gly Ala Leu
                245                 250                 255

Ile Ser Gly Gly Ala Asp Thr Ala Gln Ala Lys Leu Glu Ile Met Glu
                260                 265                 270

Ala Cys Gly Ile Lys Val Thr Lys Asn Pro Ser Glu Met Gly Arg Leu
                275                 280                 285

Leu Lys Ala Met Leu
    290
```

<210> SEQ ID NO 18
<211> LENGTH: 1197
<212> TYPE: DNA
<213> ORGANISM: Artificial sequence
<220> FEATURE:
<223> OTHER INFORMATION: Synthetic

<400> SEQUENCE: 18

```
atggcgcaac agatcctcga gggcattcgc gtcctcgaac tcggacaact catcgccggc      60
cccttttgccg ccaagaccct ggccgacttt ggcgcccaca tcatcaaggt ggagccgccg    120
gggcagggcg acccgctgcg caaatggcgc atgctgcatg aaggcacctc ggtctggtgg    180
gaggcgcagt cgcgcaacaa ggagtcgatc tgcatcgacc tgcgccagcc ggaaggccag    240
gcactggtgc gcaagctggc cgccgaggcc gacgtgctga tcgagaactt ccgccccggc    300
accatggaga gtggggcct gggctgggac gtgctgcatg ccgacaaccc cgcgcctgatc    360
atgctgcgcg tgtcgggcta tgccagacc gggccgaaga aggatgagcc cggctttgcc    420
gcggtggccg aagccatggc cggcctgcgc cacctgaccg cgagcccgg ccgcgcgccg    480
gtgcgcgccg gcctgtcgct gggcgacacc atcgccggcc tgcacggcgc catgggcgtg    540
ctgctggcgc tgtaccagcg cgacgcgcgc ggcggcgaag ccaggtcat cgacgtggcg    600
ctgtacgagt cgctgttcaa cctgagcgaa agtctgctgc cggaatactc ggcttttggc    660
gcggtgcggg agcccgccgg cggcgcgctg ccggggatcg cgccgtccaa cgcgtacccc    720
tgtgccagcg gcgaatacgt gctggtggcg gccaatggcg acgccatctt caagcgcatg    780
```

```
atgctggcca tcggccggcc cgacctggcc gacgatccgt cgctggcgca gaacgatggc     840
cgcgtgaagc gcgtcgacga gatcgatgcc gccatcgccg actggacccg cacgcagacg     900
gtggactcgg cgctggccct gctgcgcgac gcgcaggtgc cgtcgggccg catctatacc     960
gtcaaggaca ttgccgaaga cccgcactac cgcgcccgcg cgtgatcga gtcggtgacc    1020 tcggccggcg gactcacggt ggaagtgccg ggcgtggtgc ccaagctgtc ggccagcccc    1080
ggcgagatcc atgaccgcgc gccgacgctc ggcgagcata ccgatacggt gctgaagcag    1140
gcaggcttcg acgacgccgc catcgccgac ctgcgtgcgc gcaaggtgat cgcatga       1197
```

<210> SEQ ID NO 19
<211> LENGTH: 398
<212> TYPE: PRT
<213> ORGANISM: Artificial sequence
<220> FEATURE:
<223> OTHER INFORMATION: Synthetic

<400> SEQUENCE: 19

```
Met Ala Gln Gln Ile Leu Glu Gly Ile Arg Val Leu Glu Leu Gly Gln
1               5                   10                  15

Leu Ile Ala Gly Pro Phe Ala Ala Lys Thr Leu Ala Asp Phe Gly Ala
            20                  25                  30

His Ile Ile Lys Val Glu Pro Pro Gly Gln Gly Asp Pro Leu Arg Lys
        35                  40                  45

Trp Arg Met Leu His Glu Gly Thr Ser Val Trp Trp Glu Ala Gln Ser
    50                  55                  60

Arg Asn Lys Glu Ser Ile Cys Ile Asp Leu Arg Gln Pro Glu Gly Gln
65                  70                  75                  80

Ala Leu Val Arg Lys Leu Ala Ala Glu Ala Asp Val Leu Ile Glu Asn
                85                  90                  95

Phe Arg Pro Gly Thr Met Glu Lys Trp Gly Leu Gly Trp Asp Val Leu
            100                 105                 110

His Ala Asp Asn Pro Arg Leu Ile Met Leu Arg Val Ser Gly Tyr Gly
        115                 120                 125

Gln Thr Gly Pro Lys Lys Asp Glu Pro Gly Phe Ala Ala Val Ala Glu
    130                 135                 140

Ala Met Ala Gly Leu Arg His Leu Thr Gly Glu Pro Gly Arg Ala Pro
145                 150                 155                 160

Val Arg Ala Gly Leu Ser Leu Gly Asp Thr Ile Ala Gly Leu His Gly
                165                 170                 175

Ala Met Gly Val Leu Leu Ala Leu Tyr Gln Arg Asp Ala Arg Gly Gly
            180                 185                 190

Glu Gly Gln Val Ile Asp Val Ala Leu Tyr Glu Ser Leu Phe Asn Leu
        195                 200                 205

Ser Glu Ser Leu Leu Pro Glu Tyr Ser Ala Phe Gly Ala Val Arg Gln
    210                 215                 220

Pro Ala Gly Gly Ala Leu Pro Gly Ile Ala Pro Ser Asn Ala Tyr Pro
225                 230                 235                 240

Cys Ala Ser Gly Glu Tyr Val Leu Val Ala Ala Asn Gly Asp Ala Ile
                245                 250                 255

Phe Lys Arg Met Met Leu Ala Ile Gly Arg Pro Asp Leu Ala Asp Asp
            260                 265                 270

Pro Ser Leu Ala Gln Asn Asp Gly Arg Val Lys Arg Val Asp Glu Ile
        275                 280                 285
```

Asp Ala Ala Ile Ala Asp Trp Thr Arg Thr Gln Thr Val Asp Ser Ala
290                 295                 300

Leu Ala Leu Leu Arg Asp Ala Gln Val Pro Ser Gly Arg Ile Tyr Thr
305                 310                 315                 320

Val Lys Asp Ile Ala Glu Asp Pro His Tyr Arg Ala Arg Gly Val Ile
            325                 330                 335

Glu Ser Val Thr Ser Ala Gly Gly Leu Thr Val Glu Val Pro Gly Val
            340                 345                 350

Val Pro Lys Leu Ser Ala Ser Pro Gly Glu Ile His Asp Arg Ala Pro
355                 360                 365

Thr Leu Gly Glu His Thr Asp Thr Val Leu Lys Gln Ala Gly Phe Asp
370                 375                 380

Asp Ala Ala Ile Ala Asp Leu Arg Ala Arg Lys Val Ile Ala
385                 390                 395

<210> SEQ ID NO 20
<211> LENGTH: 1191
<212> TYPE: DNA
<213> ORGANISM: Artificial sequence
<220> FEATURE:
<223> OTHER INFORMATION: Synthetic

<400> SEQUENCE: 20

```
atgcaacccc tcaaagacat cacggttgtc acatttgaac acgcgattgc ggcgcctttt      60
gccacacggc agcttgccga tctgggtgca cgagttatta agatcgagcg gcctggggtc     120
ggcgatttcg cccgtggtta cgatgagcgg gtccgtggcc tggcctcgca tttcgtctgg     180
acaaaccgct cgaaggaaag cctgacgctc gatgtcaagc accggccgc ggctggcgta      240
ttacagcgtc tgattgagga aaaggcggac gtggtggttc agaacctcgc accaggcgcc     300
gcagcacggc ttggtctggg ctacgaaacg ctttccgccg taaagcccca aatcattgtg     360
tgtgatattt cgggctatgg cgacaacccg aagaatcctg accataccg cgacaagaag      420
gcctatgacc ttctcgttca gagcgaagcc ggatttctgt ccgtgacggg gacgcctgac     480
gtgccttgca aggctgggcc ttccattgcc gatatcgccg ccggcatgta tgcctacaca     540
aacattctgg ccgctctgtt acaacgcaat cagacgggcc gagggcaacg tattgacatc     600
tccatgctag aggcgctggc ggaatggaat agttaccctc tctactacgc ttttgatggg     660
gcacagccgc cgcagcgcac gggcgcaagc acgccacaa tctacccta tggaccgttt       720
ccggctggcg atgggcgac agtaatgttg gggttgcaga acgagcggga atgggcaaac     780
ttctgcaaca cagtgctcca gcggcccgaa ctgatcgaag atccccgctt tagctcaaac     840
tcgagacgcg tggccgagcg cactgcactg aggcagatca tcgtagatgc ctttttgcct     900
ctaaccggtg cccaagtggt gcagcgattg gagttggccc agatcgcgaa tgccagtgtc     960
aatgacatgc agggggtgtg ggagcatgct caactcaagg cgcgcggccg ctggactgaa    1020
gtcgactcgc ccaagggcat gctgccggct ctcttgcccc caggaacctg gaacgaaggg    1080
ccgcgtatgg atccgatacc ggcacttggt cagcacaccg acacaattct cgcggagctt    1140
ggatacgcct ccgacgaaat cgccgtgatg cgcgctgata gcgttgtgta a             1191
```

<210> SEQ ID NO 21
<211> LENGTH: 396
<212> TYPE: PRT
<213> ORGANISM: Artificial sequence
<220> FEATURE:
<223> OTHER INFORMATION: Synthetic

<400> SEQUENCE: 21

```
Met Gln Pro Leu Lys Asp Ile Thr Val Val Thr Phe Glu His Ala Ile
1               5                   10                  15

Ala Ala Pro Phe Ala Thr Arg Gln Leu Ala Asp Leu Gly Ala Arg Val
            20                  25                  30

Ile Lys Ile Glu Arg Pro Gly Val Gly Asp Phe Ala Arg Gly Tyr Asp
        35                  40                  45

Glu Arg Val Arg Gly Leu Ala Ser His Phe Val Trp Thr Asn Arg Ser
    50                  55                  60

Lys Glu Ser Leu Thr Leu Asp Val Lys His Pro Ala Ala Gly Val
65                  70                  75                  80

Leu Gln Arg Leu Ile Glu Glu Lys Ala Asp Val Val Gln Asn Leu
                85                  90                  95

Ala Pro Gly Ala Ala Arg Leu Gly Leu Gly Tyr Glu Thr Leu Ser
            100                 105                 110

Ala Val Lys Pro Gln Ile Ile Val Cys Asp Ile Ser Gly Tyr Gly Asp
        115                 120                 125

Asn Pro Lys Asn Pro Gly Pro Tyr Arg Asp Lys Lys Ala Tyr Asp Leu
    130                 135                 140

Leu Val Gln Ser Glu Ala Gly Phe Leu Ser Val Thr Gly Thr Pro Asp
145                 150                 155                 160

Val Pro Cys Lys Ala Gly Pro Ser Ile Ala Asp Ile Ala Ala Gly Met
                165                 170                 175

Tyr Ala Tyr Thr Asn Ile Leu Ala Ala Leu Leu Gln Arg Asn Gln Thr
            180                 185                 190

Gly Arg Gly Gln Arg Ile Asp Ile Ser Met Leu Glu Ala Leu Ala Glu
        195                 200                 205

Trp Asn Ser Tyr Pro Leu Tyr Tyr Ala Phe Asp Gly Ala Gln Pro Pro
    210                 215                 220

Gln Arg Thr Gly Ala Ser His Ala Thr Ile Tyr Pro Tyr Gly Pro Phe
225                 230                 235                 240

Pro Ala Gly Asp Gly Ala Thr Val Met Leu Gly Leu Gln Asn Glu Arg
                245                 250                 255

Glu Trp Ala Asn Phe Cys Asn Thr Val Leu Gln Arg Pro Glu Leu Ile
            260                 265                 270

Glu Asp Pro Arg Phe Ser Ser Asn Ser Arg Val Ala Glu Arg Thr
        275                 280                 285

Ala Leu Arg Gln Ile Ile Val Asp Ala Phe Leu Pro Leu Thr Gly Ala
    290                 295                 300

Gln Val Val Gln Arg Leu Glu Leu Ala Gln Ile Ala Asn Ala Ser Val
305                 310                 315                 320

Asn Asp Met Gln Gly Val Trp Glu His Ala Gln Leu Lys Ala Arg Gly
                325                 330                 335

Arg Trp Thr Glu Val Asp Ser Pro Lys Gly Met Leu Pro Ala Leu Leu
            340                 345                 350

Pro Pro Gly Thr Trp Asn Glu Gly Pro Arg Met Asp Pro Ile Pro Ala
        355                 360                 365

Leu Gly Gln His Thr Asp Thr Ile Leu Ala Glu Leu Gly Tyr Ala Ser
    370                 375                 380

Asp Glu Ile Ala Val Met Arg Ala Asp Ser Val Val
385                 390                 395
```

<210> SEQ ID NO 22

<211> LENGTH: 861
<212> TYPE: DNA
<213> ORGANISM: Artificial sequence
<220> FEATURE:
<223> OTHER INFORMATION: Synthetic

<400> SEQUENCE: 22

```
gtggacgaac aggcagttga ccccaggacg tggattggac gcagcgagca gtgggaggac    60
acagtcactg ccgcgccgat cgcagcgctg cgtgcgacga tggattaccc cgcagcagcg   120
cagacagcag gcactccatt gccgccactg tggcattggc tttatttctt acccatgcat   180
cgtcaaagcg aaattgggca cgatggccat gccaagcgcg gcggctttct accccctgtg   240
ccattgcccc gccgcatgtg ggcaggcggc caattcgagt ttcgccatcc acttcgggtg   300
ggcgacaaga tccagcgcac ctccgtcatc gacgatgtta caagcaagga ggggcggacc   360
ggaaagttag tatttgtaag agtgcgtcat gagatccgcg ccatcggtac tgcggaaccg   420
gcgttagtgg agtttcacga catcgtttac cgagaggcac agcagtcggg cgaggcgcct   480
gtcatgcccc aagcggcgcc cgcggaagcg gcttggcagc gccaaattgt tccggacgac   540
gtcttgctgt ccgctattc ggccctgact ttcaatgggc atcgcatcca ctatgaccgt   600
cgctacgtga cagaggtcga aggctacccc ggcttgattg tccacggccc gctgatcgct   660
acgttgctac tggatctgct gcggcgtgaa ttgccccagg cagaggtcgc cagctttcga   720
ttccgtgcgg tgcgcccgac cttcgacctg catcccttcc gggtcagcgg tcaaccgcag   780
tctgacggca aaacagttcg cttgtgggca tccgaccacg agggctggct gaccatggac   840
gccacggcag tccttcgctg a                                             861
```

<210> SEQ ID NO 23
<211> LENGTH: 286
<212> TYPE: PRT
<213> ORGANISM: Artificial sequence
<220> FEATURE:
<223> OTHER INFORMATION: Synthetic

<400> SEQUENCE: 23

```
Met Asp Glu Gln Ala Val Asp Pro Arg Thr Trp Ile Gly Arg Ser Glu
1               5                   10                  15

Gln Trp Glu Asp Thr Val Thr Ala Ala Pro Ile Ala Ala Leu Arg Ala
            20                  25                  30

Thr Met Asp Tyr Pro Ala Ala Ala Gln Thr Ala Gly Thr Pro Leu Pro
        35                  40                  45

Pro Leu Trp His Trp Leu Tyr Phe Leu Pro Met His Arg Gln Ser Glu
    50                  55                  60

Ile Gly His Asp Gly His Ala Lys Arg Gly Gly Phe Leu Pro Pro Val
65                  70                  75                  80

Pro Leu Pro Arg Arg Met Trp Ala Gly Gly Gln Phe Glu Phe Arg His
                85                  90                  95

Pro Leu Arg Val Gly Asp Lys Ile Gln Arg Thr Ser Val Ile Asp Asp
            100                 105                 110

Val Thr Ser Lys Glu Gly Arg Thr Gly Lys Leu Val Phe Val Arg Val
        115                 120                 125

Arg His Glu Ile Arg Ala Ile Gly Thr Ala Glu Pro Ala Leu Val Glu
    130                 135                 140

Phe His Asp Ile Val Tyr Arg Glu Ala Gln Gln Ser Gly Glu Ala Pro
145                 150                 155                 160

Val Met Pro Gln Ala Ala Pro Ala Glu Ala Ala Trp Gln Arg Gln Ile
```

165                 170                 175

Val Pro Asp Asp Val Leu Leu Phe Arg Tyr Ser Ala Leu Thr Phe Asn
                180                 185                 190

Gly His Arg Ile His Tyr Asp Arg Arg Tyr Val Thr Glu Val Glu Gly
            195                 200                 205

Tyr Pro Gly Leu Ile Val His Gly Pro Leu Ile Ala Thr Leu Leu Leu
        210                 215                 220

Asp Leu Leu Arg Arg Glu Leu Pro Gln Ala Glu Val Ala Ser Phe Arg
225                 230                 235                 240

Phe Arg Ala Val Arg Pro Thr Phe Asp Leu His Pro Phe Arg Val Ser
                245                 250                 255

Gly Gln Pro Gln Ser Asp Gly Lys Thr Val Arg Leu Trp Ala Ser Asp
            260                 265                 270

His Glu Gly Trp Leu Thr Met Asp Ala Thr Ala Val Leu Arg
        275                 280                 285

<210> SEQ ID NO 24
<211> LENGTH: 1221
<212> TYPE: DNA
<213> ORGANISM: Artificial sequence
<220> FEATURE:
<223> OTHER INFORMATION: Synthetic

<400> SEQUENCE: 24
atgggagctt taagccatct ccgcgtcctc gacctgaccc gcgtccttgc cgggccgtgg      60
tgcgcccaga accttgccga tttcggcgcc gacgtgatca agatcgagcg ccccggcgcc     120
ggcgacgata cccgcacctg ggcccgccc tggctcaagg acgaggacgg ccgcgacacc     180
gccgaagccg cctactacct ggccgccaac cgcaacaagc gctccgtgac ctgcgacatc     240
agcacgccgg aaggtcagca gatcgtgcgc gagctggcgg cgcagagcga cgtggtgctg     300
gagaactaca aggtaggcca gctcaggaag tacggcctgg actatgagtc gctcaggcag     360
gtcaagcccg acctgatcta ctgctcggtc accggcttcg ccagaccggg ccgtacgcc      420 gcgcgcccgg gctatgactt catcatccag ggcatgggcg gcttcatgag cctgaccggc     480
gagcgcgacg acctgcccgg cggcggcccg cagaaggccg gcgtggccat ttccgacctg     540
atgaccggcc agtacgccac catcgccgtg ctggcggcgc tggcgcaccg cgaccgcacc     600
ggcgagggcc agtacatcga catggccctg ctggacgtgc aggtggcgat gctggccaac     660
atgaacacca actacctggc cagcggccag gcgccgcgcc gctggggcaa tgcgcacccc     720
aatatcgtcc cctaccagac cttccaggcc gccgatggct ggatcatcgt ggcggtgggc     780
aacgacgggc agttccgcaa gttcgtcacc gacggcggca agcccgagct ggccgacgac     840
ccgcgctttg ccaccaaccc gcagcgcgtg gccaaccgcg acgtgctggt gccgatcctg     900
gccgagatgg tgcgcccgcg caccgcgcc cagtggatcc gcgacctgga ggccgccggc     960
gtgccgtgcg gccgatcaa caccctcgac gacgtgttcg aggacgacca ggtcaaggcg    1020
cgcggcctgc gcgtggacct gccccacccc agcgccggcg aggtcaggct ggtgggcagc    1080
ccgatcaaga tgagcgccac gccgccgcag gcactgcgcc acccgccgct gctgggcgag    1140
cacaccgaca cggtgctggc cgagacgctg ggctacggcc ctgagcagat cgaagcgctg    1200
cgtgcaaagg gtgtgctgta a                                              1221

<210> SEQ ID NO 25
<211> LENGTH: 406
<212> TYPE: PRT

<213> ORGANISM: Artificial sequence
<220> FEATURE:
<223> OTHER INFORMATION: Synthetic

<400> SEQUENCE: 25

Met Gly Ala Leu Ser His Leu Arg Val Leu Asp Leu Thr Arg Val Leu
1               5                   10                  15

Ala Gly Pro Trp Cys Ala Gln Asn Leu Ala Asp Phe Gly Ala Asp Val
            20                  25                  30

Ile Lys Ile Glu Arg Pro Gly Ala Gly Asp Asp Thr Arg Thr Trp Gly
        35                  40                  45

Pro Pro Trp Leu Lys Asp Glu Asp Gly Arg Asp Thr Ala Glu Ala Ala
50                  55                  60

Tyr Tyr Leu Ala Ala Asn Arg Asn Lys Arg Ser Val Thr Cys Asp Ile
65                  70                  75                  80

Ser Thr Pro Glu Gly Gln Gln Ile Val Arg Glu Leu Ala Ala Gln Ser
                85                  90                  95

Asp Val Val Leu Glu Asn Tyr Lys Val Gly Gln Leu Arg Lys Tyr Gly
            100                 105                 110

Leu Asp Tyr Glu Ser Leu Arg Gln Val Lys Pro Asp Leu Ile Tyr Cys
        115                 120                 125

Ser Val Thr Gly Phe Gly Gln Thr Gly Pro Tyr Ala Ala Arg Pro Gly
130                 135                 140

Tyr Asp Phe Ile Ile Gln Gly Met Gly Gly Phe Met Ser Leu Thr Gly
145                 150                 155                 160

Glu Arg Asp Asp Leu Pro Gly Gly Pro Gln Lys Ala Gly Val Ala
                165                 170                 175

Ile Ser Asp Leu Met Thr Gly Gln Tyr Ala Thr Ile Ala Val Leu Ala
            180                 185                 190

Ala Leu Ala His Arg Asp Arg Thr Gly Glu Gly Gln Tyr Ile Asp Met
        195                 200                 205

Ala Leu Leu Asp Val Gln Val Ala Met Leu Ala Asn Met Asn Thr Asn
210                 215                 220

Tyr Leu Ala Ser Gly Gln Ala Pro Arg Arg Trp Gly Asn Ala His Pro
225                 230                 235                 240

Asn Ile Val Pro Tyr Gln Thr Phe Gln Ala Ala Asp Gly Trp Ile Ile
                245                 250                 255

Val Ala Val Gly Asn Asp Gly Gln Phe Arg Lys Phe Val Thr Asp Gly
            260                 265                 270

Gly Lys Pro Glu Leu Ala Asp Asp Pro Arg Phe Ala Thr Asn Pro Gln
        275                 280                 285

Arg Val Ala Asn Arg Asp Val Leu Val Pro Ile Leu Ala Glu Met Val
290                 295                 300

Arg Pro Arg Thr Arg Ala Gln Trp Ile Arg Asp Leu Glu Ala Ala Gly
305                 310                 315                 320

Val Pro Cys Gly Pro Ile Asn Thr Leu Asp Asp Val Phe Glu Asp Asp
                325                 330                 335

Gln Val Lys Ala Arg Gly Leu Arg Val Asp Leu Pro His Pro Ser Ala
            340                 345                 350

Gly Glu Val Arg Leu Val Gly Ser Pro Ile Lys Met Ser Ala Thr Pro
        355                 360                 365

Pro Gln Ala Leu Arg His Pro Pro Leu Leu Gly Glu His Thr Asp Thr
370                 375                 380

Val Leu Ala Glu Thr Leu Gly Tyr Gly Pro Glu Gln Ile Glu Ala Leu

Arg Ala Lys Gly Val Leu
            405

<210> SEQ ID NO 26
<211> LENGTH: 1236
<212> TYPE: DNA
<213> ORGANISM: Artificial sequence
<220> FEATURE:
<223> OTHER INFORMATION: Synthetic

<400> SEQUENCE: 26

```
atgacagatt tccgcgactc gggcgcacag gcgcctgcct ccaccttgcc gctggccggc    60
gtgcgcgtgc tcgacgtcag ccaggtcatg gccgggccct acgcctgcat gctgctggct   120
gatctgggcg ccgacgtgat caagatcgaa ccgcccgatg gcggcgacca gacgcgcggc   180
gcgatgggtt tcaagatgaa gggctcggac agcatgggct cctcaacat gaaccgcaac    240
aagcgcagcg tcaccctgga tctgaagacc gaatccggcc ggcaggtgct ttatcgcctg   300
gcggaaacgg ccgacatcct ggtggagaac taccgacccg cgtgatgaa gcggctgggg    360
atcgactatg agaccctcgc caggatcaat cccaagctgg tctactgcag catctcgggc   420
tttggccaga gcgggccgtg ggccgggcgg ccgggctttg acctgatggc gcaggcgatg   480
tcgggcgtga tgagcgtcac cggctacccg ggcggcgcgc cggtgaaggc gggcgtaccg   540
gtggccgaca tcggctgcgc gctgttcgcc acctacggca tgctgtctgc ctatatcggc   600
gccagggaga cgggcaaggg gcagtatgtc gatgcatcgc tgttcgactc cgcgctggcg   660
ttctcggtgt gggacacctg cgaatactgg ggcacgggcc gcgagcccga ccgctgggc    720
acggccaacc gcatgagcgc gccttaccag gcgatgaagt ccgccgacgg ctacttcgtc   780
atggggggcca ccaaccagaa gctgtggcaa ctgctgtgca cacgctcga ccggcccgac    840
ctgctcgcgg acgagcgctt tgccaccgtg gcgctgcgcc tggccaaccg gcaggcactg   900
atcgcgatgc tggaggagag cttcgtcaag gagagcagcg actactggat cgagcgcctg   960
ctcggcgtcg gcattccggc cgggccgatc ctgacctacc gcaggcctt cgacagcgag  1020
cacggccgcc accgccagat gcgcatcgaa atcgatcatc cgatcgaggg caaggtgccc  1080
aatatcggct tcgcggtgaa gatgggcggc acgccccagc aggtacggcg cgcgccgccg  1140
ctgctcggcc agcatacgga agaaatcctg gccgagctgg gtatcccgaa ggacgaacaa  1200
cagtcgctgg ctgtagccgg cgcattcgga tcatga                            1236
```

<210> SEQ ID NO 27
<211> LENGTH: 411
<212> TYPE: PRT
<213> ORGANISM: Artificial sequence
<220> FEATURE:
<223> OTHER INFORMATION: Synthetic

<400> SEQUENCE: 27

Met Thr Asp Phe Arg Asp Ser Gly Ala Gln Ala Pro Ala Ser Thr Leu
1               5                   10                  15

Pro Leu Ala Gly Val Arg Val Leu Asp Val Ser Gln Val Met Ala Gly
            20                  25                  30

Pro Tyr Ala Cys Met Leu Leu Ala Asp Leu Gly Ala Asp Val Ile Lys
        35                  40                  45

Ile Glu Pro Pro Asp Gly Gly Asp Gln Thr Arg Gly Ala Met Gly Phe
    50                  55                  60

Lys Met Lys Gly Ser Asp Ser Met Gly Phe Leu Asn Met Asn Arg Asn
 65                  70                  75                  80

Lys Arg Ser Val Thr Leu Asp Leu Lys Thr Glu Ser Gly Arg Gln Val
                 85                  90                  95

Leu Tyr Arg Leu Ala Glu Thr Ala Asp Ile Leu Val Glu Asn Tyr Arg
            100                 105                 110

Pro Gly Val Met Lys Arg Leu Gly Ile Asp Tyr Glu Thr Leu Ala Arg
        115                 120                 125

Ile Asn Pro Lys Leu Val Tyr Cys Ser Ile Ser Gly Phe Gly Gln Ser
    130                 135                 140

Gly Pro Trp Ala Gly Arg Pro Gly Phe Asp Leu Met Ala Gln Ala Met
145                 150                 155                 160

Ser Gly Val Met Ser Val Thr Gly Tyr Pro Gly Gly Ala Pro Val Lys
                165                 170                 175

Ala Gly Val Pro Val Ala Asp Ile Gly Cys Ala Leu Phe Ala Thr Tyr
            180                 185                 190

Gly Met Leu Ser Ala Tyr Ile Gly Ala Arg Glu Thr Gly Lys Gly Gln
        195                 200                 205

Tyr Val Asp Ala Ser Leu Phe Asp Ser Ala Leu Ala Phe Ser Val Trp
    210                 215                 220

Asp Thr Cys Glu Tyr Trp Gly Thr Gly Arg Glu Pro Glu Pro Leu Gly
225                 230                 235                 240

Thr Ala Asn Arg Met Ser Ala Pro Tyr Gln Ala Met Lys Ser Ala Asp
                245                 250                 255

Gly Tyr Phe Val Met Gly Ala Thr Asn Gln Lys Leu Trp Gln Leu Leu
            260                 265                 270

Cys Asn Thr Leu Asp Arg Pro Asp Leu Leu Ala Asp Glu Arg Phe Ala
        275                 280                 285

Thr Val Ala Leu Arg Leu Ala Asn Arg Gln Ala Leu Ile Ala Met Leu
    290                 295                 300

Glu Glu Ser Phe Val Lys Glu Ser Ser Asp Tyr Trp Ile Glu Arg Leu
305                 310                 315                 320

Leu Gly Val Gly Ile Pro Ala Gly Pro Ile Leu Thr Tyr Pro Gln Ala
                325                 330                 335

Phe Asp Ser Glu His Gly Arg His Arg Gln Met Arg Ile Glu Ile Asp
            340                 345                 350

His Pro Ile Glu Gly Lys Val Pro Asn Ile Gly Phe Ala Val Lys Met
        355                 360                 365

Gly Gly Thr Pro Gln Val Arg Arg Ala Pro Pro Leu Leu Gly Gln
    370                 375                 380

His Thr Glu Glu Ile Leu Ala Glu Leu Gly Ile Pro Lys Asp Glu Gln
385                 390                 395                 400

Gln Ser Leu Ala Val Ala Gly Ala Phe Gly Ser
                405                 410

<210> SEQ ID NO 28
<211> LENGTH: 1191
<212> TYPE: DNA
<213> ORGANISM: Artificial sequence
<220> FEATURE:
<223> OTHER INFORMATION: Synthetic

<400> SEQUENCE: 28
atgaaaccca gcctacgccc ccttgatggc atcaccgttc tggcgcttga gcacgctgta      60
gcggcgccct tcgccagccg ccagctcgcc gatctcggcg cccgcgtcat caaggtggaa     120

```
cgcccgctcg ttggcgattt cgcccgcgac tatgaccatt ccgtgcacgg ccagtcgtcg      180
ttctttgtct gggcaaatcg cggcaaggaa agcctcacgc tggatctcaa gaagcccgag      240
gccaaggcga tcgtgcacaa gctgctcgcc gaagcggacg tgttcatcca gaacctggcg      300
ccgggagccg cccaacgcat gggactggac ttcgagtcat tgcatgctga ctatcctgag      360
ctgatcgtct gcgatatctc agggtatggt gacagcgggc ataccgcga caagaaggcc       420 tatgacctgt tgatccaggc cgctgcgggc ctgatctcgg taagcggtac ggaagctgcg      480
ccgtcgcgca ccggcatttc catcgcggac attgccgctg gcatgtacgc ctataccggc      540
atcctgtccg ccttgctgca acgcgcacgg actggcgccg gcctccgggt tgaagtcacc      600
atgctcgagg cgttgagcga atggatgtca tatcccctga actttgctca ctatggcggc      660
acgccgccgg cacgcaacgg cgttgcgcat ccgggtatcg cccctatgg ccagtaccag       720 accggcgatg gggccagcgt catcttcggg ctgcagaacg aacgggaatg cagcggttc       780 tgctccgagt gctggagga cccggccctg gcggcagatg accgctttaa ctccaatctc       840
caacgcgtcg ccaatcgcgc ggcgctggac caggagatcg ccagtcatct ccgctccatg      900
accggggaac agctggtcaa acgtctcgat cgcggggca ttgccaactc gccctgaac       960 gacatgcatg atgtttggca gcacgcgcaa tttgccgcac gcaatcgctg gcgggaagtc      1020
cagacgccgg gtggcgccat ccaggcactt ctgccgccgg ctacgctgtc gggcgtaccg      1080
gcttccatgg ggaatgttcc ggcagtcggc gagcactctg cttctgtcct gaagtcgctc      1140
ggcatgaacg aggcagagat cgaggcactg gtggcggcgg gcacgatctg a              1191
```

```
<210> SEQ ID NO 29
<211> LENGTH: 396
<212> TYPE: PRT
<213> ORGANISM: Artificial sequence
<220> FEATURE:
<223> OTHER INFORMATION: Synthetic

<400> SEQUENCE: 29
```

Met Lys Pro Ser Leu Arg Pro Leu Asp Gly Ile Thr Val Leu Ala Leu
1               5                   10                  15

Glu His Ala Val Ala Ala Pro Phe Ala Ser Arg Gln Leu Ala Asp Leu
                20                  25                  30

Gly Ala Arg Val Ile Lys Val Glu Arg Pro Leu Val Gly Asp Phe Ala
            35                  40                  45

Arg Asp Tyr Asp His Ser Val His Gly Gln Ser Ser Phe Phe Val Trp
        50                  55                  60

Ala Asn Arg Gly Lys Glu Ser Leu Thr Leu Asp Leu Lys Lys Pro Glu
65                  70                  75                  80

Ala Lys Ala Ile Val His Lys Leu Leu Ala Glu Ala Asp Val Phe Ile
                85                  90                  95

Gln Asn Leu Ala Pro Gly Ala Ala Gln Arg Met Gly Leu Asp Phe Glu
                100                 105                 110

Ser Leu His Ala Asp Tyr Pro Glu Leu Ile Val Cys Asp Ile Ser Gly
            115                 120                 125

Tyr Gly Asp Ser Gly Pro Tyr Arg Asp Lys Lys Ala Tyr Asp Leu Leu
        130                 135                 140

Ile Gln Ala Ala Ala Gly Leu Ile Ser Val Ser Gly Thr Glu Ala Ala
145                 150                 155                 160

Pro Ser Arg Thr Gly Ile Ser Ile Ala Asp Ile Ala Ala Gly Met Tyr
                165                 170                 175

```
Ala Tyr Thr Gly Ile Leu Ser Ala Leu Leu Gln Arg Ala Arg Thr Gly
            180                 185                 190

Ala Gly Leu Arg Val Glu Val Thr Met Leu Glu Ala Leu Ser Glu Trp
        195                 200                 205

Met Ser Tyr Pro Leu Asn Phe Ala His Tyr Gly Gly Thr Pro Pro Ala
210                 215                 220

Arg Asn Gly Val Ala His Pro Gly Ile Ala Pro Tyr Gly Gln Tyr Gln
225                 230                 235                 240

Thr Gly Asp Gly Ala Ser Val Ile Phe Gly Leu Gln Asn Glu Arg Glu
                245                 250                 255

Trp Gln Arg Phe Cys Ser Glu Val Leu Glu Asp Pro Ala Leu Ala Ala
            260                 265                 270

Asp Asp Arg Phe Asn Ser Asn Leu Gln Arg Val Ala Asn Arg Ala Ala
        275                 280                 285

Leu Asp Gln Glu Ile Ala Ser His Leu Arg Ser Met Thr Gly Glu Gln
290                 295                 300

Leu Val Lys Arg Leu Asp Arg Gly Gly Ile Ala Asn Ser Pro Leu Asn
305                 310                 315                 320

Asp Met His Asp Val Trp Gln His Ala Gln Phe Ala Ala Arg Asn Arg
                325                 330                 335

Trp Arg Glu Val Gln Thr Pro Gly Gly Ala Ile Gln Ala Leu Leu Pro
            340                 345                 350

Pro Ala Thr Leu Ser Gly Val Pro Ala Ser Met Gly Asn Val Pro Ala
        355                 360                 365

Val Gly Glu His Ser Ala Ser Val Leu Lys Ser Leu Gly Met Asn Glu
370                 375                 380

Ala Glu Ile Glu Ala Leu Val Ala Ala Gly Thr Ile
385                 390                 395

<210> SEQ ID NO 30
<211> LENGTH: 1224
<212> TYPE: DNA
<213> ORGANISM: Artificial sequence
<220> FEATURE:
<223> OTHER INFORMATION: Synthetic

<400> SEQUENCE: 30
atgcagcagt catcccccgg cgccctcgcc ggcctgcgtg tgatcgacct cacccagatg      60
ctggccggcc cgttttgcac ccagatcctg gccgaccacg gtgccgacgt catcaaggtc     120
gaggccatga cgggcgacgg cacgcgcctg accgccccct ctgcgaggac gacacgctc     180 cgcgagtatg cggctatttt ccaaagcgtc aaccgcaaca agcggtcgat tgccgtcgat     240
ctgaagaccg tcgaggggct ggcgcttgcc cgcaagctga tcgacggcgc cgatatcgtg     300
gtcgagaact tccgcgccgg cgtgatggaa cgcctcgggc tgggctggga aggctgcgg     360 gagcgcaacc cgcgcctcgt ctatggcacc gtgcggggct tcggcgatcc cgctcgggc     420 gccagcccct acgcggactg ccagcctat gacgtagtcg cacaggcgat gggcggcatg     480
acgggcatca ccggccccga ccaccaaaca ccgatgaaga ttggccccgg cgtaggcgac     540
accatcccgg cgctgatgct ctgcatcggc atcctgtcgg ctgtacaccg ggtgaaggaa     600
accggcaagg gccagttcgt ggacgtggcg atgacggacg ccgtgctggc catgtgcgag     660
cgcatcgtct accagacctc ctacaccggc gtggtacccg gccggaaggg caaccgccat     720
cccctgctgt gcccgttcgg cctgttccgg gcgcgcgacg gctacgtgtc catcgccgtc     780
```

```
gccaacgatc cgctgtggga gaagctggcc gccgccatcg gccatccgga actgggcacc        840
gatccggctt tctcgaccaa tgcggcgcgc gtcgccaaca tgcagcaagt catcgatttg        900
ctcgaagact tcacgtccgg ccgcaccaag gaacaaatcg cggccgtcct gggcggcaag        960
gtgccgttcg gccggtctg cacgtccgcc gagatctttg ccgatccgca ttatgcggtg       1020
cggcagatgc tggtggatgt cgagcagccc ggttcggcgc agcgcgtgaa gatcgccggc       1080
gtgccgatca agctgagcga caccccgggg gcggtccggc gccgtgcccc gatgctgggc       1140
gagcacaccg atgaagtctt gcgcgccgcc ggctacagcg gcgacgacat cgacgatctg       1200
cgcgcggtcg gtgctatccg ctaa                                              1224
```

<210> SEQ ID NO 31
<211> LENGTH: 407
<212> TYPE: PRT
<213> ORGANISM: Artificial sequence
<220> FEATURE:
<223> OTHER INFORMATION: Synthetic

<400> SEQUENCE: 31

```
Met Gln Gln Ser Ser Pro Gly Ala Leu Ala Gly Leu Arg Val Ile Asp
1               5                   10                  15

Leu Thr Gln Met Leu Ala Gly Pro Phe Cys Thr Gln Ile Leu Ala Asp
            20                  25                  30

His Gly Ala Asp Val Ile Lys Val Glu Ala Met Thr Gly Asp Gly Thr
        35                  40                  45

Arg Leu Thr Ala Pro Phe Cys Glu Asp Asp Thr Leu Arg Glu Tyr Gly
    50                  55                  60

Gly Tyr Phe Gln Ser Val Asn Arg Asn Lys Arg Ser Ile Ala Val Asp
65                  70                  75                  80

Leu Lys Thr Val Glu Gly Leu Ala Leu Ala Arg Lys Leu Ile Asp Gly
                85                  90                  95

Ala Asp Ile Val Val Glu Asn Phe Arg Ala Gly Val Met Glu Arg Leu
            100                 105                 110

Gly Leu Gly Trp Glu Arg Leu Arg Glu Arg Asn Pro Arg Leu Val Tyr
        115                 120                 125

Gly Thr Val Arg Gly Phe Gly Asp Pro Arg Ser Gly Ala Ser Pro Tyr
    130                 135                 140

Ala Asp Trp Pro Ala Tyr Asp Val Val Ala Gln Ala Met Gly Gly Met
145                 150                 155                 160

Thr Gly Ile Thr Gly Pro Asp His Gln Thr Pro Met Lys Ile Gly Pro
                165                 170                 175

Gly Val Gly Asp Thr Ile Pro Ala Leu Met Leu Cys Ile Gly Ile Leu
            180                 185                 190

Ser Ala Val His Arg Val Lys Glu Thr Gly Lys Gly Gln Phe Val Asp
        195                 200                 205

Val Ala Met Thr Asp Ala Val Leu Ala Met Cys Glu Arg Ile Val Tyr
    210                 215                 220

Gln Thr Ser Tyr Thr Gly Val Val Pro Gly Pro Glu Gly Asn Arg His
225                 230                 235                 240

Pro Leu Leu Cys Pro Phe Gly Leu Phe Arg Ala Arg Asp Gly Tyr Val
                245                 250                 255

Ser Ile Ala Val Ala Asn Asp Pro Leu Trp Glu Lys Leu Ala Ala Ala
            260                 265                 270

Ile Gly His Pro Glu Leu Gly Thr Asp Pro Ala Phe Ser Thr Asn Ala
        275                 280                 285
```

```
Ala Arg Val Ala Asn Met Gln Gln Val Ile Asp Leu Leu Glu Asp Phe
        290                 295                 300

Thr Ser Gly Arg Thr Lys Glu Gln Ile Ala Ala Val Leu Gly Gly Lys
305                 310                 315                 320

Val Pro Phe Gly Pro Val Cys Thr Ser Ala Glu Ile Phe Ala Asp Pro
                325                 330                 335

His Tyr Ala Val Arg Gln Met Leu Val Asp Val Glu Gln Pro Gly Ser
            340                 345                 350

Ala Gln Arg Val Lys Ile Ala Gly Val Pro Ile Lys Leu Ser Asp Thr
        355                 360                 365

Pro Gly Ala Val Arg Arg Ala Pro Met Leu Gly Glu His Thr Asp
    370                 375                 380

Glu Val Leu Arg Ala Ala Gly Tyr Ser Gly Asp Asp Ile Asp Asp Leu
385                 390                 395                 400

Arg Ala Val Gly Ala Ile Arg
                405

<210> SEQ ID NO 32
<211> LENGTH: 1212
<212> TYPE: DNA
<213> ORGANISM: Artificial sequence
<220> FEATURE:
<223> OTHER INFORMATION: Synthetic

<400> SEQUENCE: 32
atgacaggcc cctccaagg cgttcgcatc atcgacatga ccacggtcct gatgggaccg      60
tacgccacac agatcctcgg cgacctcggt gccgacgtga tcaaggtcga acctccgacg    120
ggagacaccg tccgcgacgt gggttaccgc cgcaacgacg gcatggcggg catcttcctg    180
cacgtcaacc gcagcaagcg cagcatcgtg ctggacctga agaagccttg cgggcgcgat    240
gcgctgctgc gcctcgtggc cgacgccgac gtgctggtct acaacgtgcg tccgcaggcg    300
atggcgcggc tgaacctggg ttacgaggaa atcgccaagg tcaatccagg catcctgtac    360
gtgggcctct acggctatgg ccaggccggc ccctatgcgg ccaagacggc ctacgacgac    420
ctgatccagg gcgccgtcgc cattcccaca ctgtcgaaga tggccggtgc cgacatcccg    480
cgctacgcgc ccagcgccat tgcggaccgc atcgtcggca tctccgccgt gaacgccatc    540
accgcgggcc tctaccaccg cctgcgtacc ggcgaaggcc agtccatcga cgtgccgatg    600
ttcgagacca tggcgcagtt catcctgggc gaccacatgg gcggcgcgac cttcgagccg    660
ccgctcggtc cgacgggcta tgggcgtgtg ctcgatccta accgccgccc gtaccgcacg    720
aaggacggct acctctgcgt gctggtctac aacgacaagc agtggcgcaa gttcttcgag    780
ctgatcggca gccgggcct gatggacagc gaccgcgct tcgccaccat cggcgagcgc      840
acgaagcata tcgacgctct ctatggcatg gttgccgagg tgatgcccac gcgcaccagc    900
gcggagtgga ccgcgctgct ggagtccacc gacatgccgg tgatgcagct ccacaccgtc    960
gattcgctga tgaccgaccc gcacctcgac gcggtgggct catcgacgt ggtcgagcac    1020 ccgaccgaag gcagatccg ctcgatggcg atcccgtcgc actggtcgaa gaccacgccg    1080
aaagtggaac gccaggcacc gcgcctcggc gaacacagcg cggaagtgct ggccgaggcc    1140
ggcttcagtg ccgacgagat ccgcaagctc gcggaagagg gcgtgacgct gatcgcgccc    1200
gccaccgagt ga                                                        1212

<210> SEQ ID NO 33
```

<211> LENGTH: 403
<212> TYPE: PRT
<213> ORGANISM: Artificial sequence
<220> FEATURE:
<223> OTHER INFORMATION: Synthetic

<400> SEQUENCE: 33

Met Thr Gly Pro Leu Gln Gly Val Arg Ile Ile Asp Met Thr Thr Val
1               5                   10                  15

Leu Met Gly Pro Tyr Ala Thr Gln Ile Leu Gly Asp Leu Gly Ala Asp
            20                  25                  30

Val Ile Lys Val Glu Pro Pro Thr Gly Asp Thr Val Arg Asp Val Gly
        35                  40                  45

Tyr Arg Arg Asn Asp Gly Met Ala Gly Ile Phe Leu His Val Asn Arg
    50                  55                  60

Ser Lys Arg Ser Ile Val Leu Asp Leu Lys Pro Cys Gly Arg Asp
65                  70                  75                  80

Ala Leu Leu Arg Leu Val Ala Asp Ala Asp Val Leu Val Tyr Asn Val
                85                  90                  95

Arg Pro Gln Ala Met Ala Arg Leu Asn Leu Gly Tyr Glu Glu Ile Ala
            100                 105                 110

Lys Val Asn Pro Gly Ile Leu Tyr Val Gly Leu Tyr Gly Tyr Gly Gln
        115                 120                 125

Ala Gly Pro Tyr Ala Ala Lys Thr Ala Tyr Asp Asp Leu Ile Gln Gly
    130                 135                 140

Ala Val Ala Ile Pro Thr Leu Ser Lys Met Ala Gly Ala Asp Ile Pro
145                 150                 155                 160

Arg Tyr Ala Pro Ser Ala Ile Ala Asp Arg Ile Val Gly Ile Ser Ala
                165                 170                 175

Val Asn Ala Ile Thr Ala Gly Leu Tyr His Arg Leu Arg Thr Gly Glu
            180                 185                 190

Gly Gln Ser Ile Asp Val Pro Met Phe Glu Thr Met Ala Gln Phe Ile
        195                 200                 205

Leu Gly Asp His Met Gly Gly Ala Thr Phe Glu Pro Pro Leu Gly Pro
    210                 215                 220

Thr Gly Tyr Gly Arg Val Leu Asp Pro Asn Arg Arg Pro Tyr Arg Thr
225                 230                 235                 240

Lys Asp Gly Tyr Leu Cys Val Leu Val Tyr Asn Asp Lys Gln Trp Arg
                245                 250                 255

Lys Phe Phe Glu Leu Ile Gly Lys Pro Gly Leu Met Asp Ser Asp Pro
            260                 265                 270

Arg Phe Ala Thr Ile Gly Glu Arg Thr Lys His Ile Asp Ala Leu Tyr
        275                 280                 285

Gly Met Val Ala Glu Val Met Pro Thr Arg Thr Ser Ala Glu Trp Thr
    290                 295                 300

Ala Leu Leu Glu Ser Thr Asp Met Pro Val Met Gln Leu His Thr Val
305                 310                 315                 320

Asp Ser Leu Met Thr Asp Pro His Leu Asp Ala Val Gly Phe Ile Asp
                325                 330                 335

Val Val Glu His Pro Thr Glu Gly Gln Ile Arg Ser Met Ala Ile Pro
            340                 345                 350

Ser His Trp Ser Lys Thr Thr Pro Lys Val Glu Arg Gln Ala Pro Arg
        355                 360                 365

Leu Gly Glu His Ser Ala Glu Val Leu Ala Glu Ala Gly Phe Ser Ala
    370                 375                 380

Asp Glu Ile Arg Lys Leu Ala Glu Glu Gly Val Thr Leu Ile Ala Pro
385                 390                 395                 400

Ala Thr Glu

<210> SEQ ID NO 34
<211> LENGTH: 1203
<212> TYPE: DNA
<213> ORGANISM: Artificial sequence
<220> FEATURE:
<223> OTHER INFORMATION: Synthetic

<400> SEQUENCE: 34

| | | | | | |
|---|---|---|---|---|---|
| atggaaacaa | gcaagtcaaa | gcccctcgcc | ggcgtacgcg | tcctggaact | ggggcagctg | 60 |
| atcgcgggc | cgtttgccgc | gcgcatgctg | gcggcgttcg | gcgcggaagt | gatcaaggtc | 120 |
| gagccgccgg | gcacgggcga | tccgctgcgc | aagtggcggc | tgttgcatga | aggcacctcg | 180 |
| gtctggtggg | aggcacagtc | ccgcgacaag | cagtcggtca | cgctggacct | gcgcacgccg | 240 |
| caaggccagg | aagtcgtgcg | caagctggcc | gcgcaaagcg | acgtgctgat | cgagaacttc | 300 |
| cgcccgggca | cgctggaagg | ctggggcctg | gctgggaca | gctgtgcgc | ggccaatccc | 360 |
| gggctggtga | tgctgcgcgt | gtccggctat | ggccagaccg | gccctatcg | cgaccggccg | 420 |
| ggcttcggcg | tcattggcga | agcgatgggc | ggcttgcgcc | acctgagcgg | cgagccgggc | 480 |
| cgcaccccgg | tgcgcgtggg | ggtatcgatg | ggggactccc | tgtccgcgct | gcacggtgtg | 540 |
| atcggcatcc | tgctggcgtt | gcggcaccgg | gagcagaacg | gcggccaggg | ccaggtcgtg | 600 |
| gatgtggcct | gtacgagtc | ggtgttcagc | atgatggaga | gctgctgcc | ggaatactcg | 660 |
| gtgttcggcg | ccgtgcggca | ggcggccggc | agcagtcttc | ccggcatcgc | gccgaccaat | 720 |
| gcgtaccgct | gcgccgacgg | caagtatgtg | ctgatcgctg | gcaatggcga | tggcatcttc | 780 |
| aggcggctga | tggacatgat | cgagcgcccc | gacctgcgcg | acgaccctgc | gctggcccac | 840 |
| aacgacggcc | gggtcagcca | ggtcgcgatg | ctcgacgccg | ccattggcga | atgggcggca | 900 |
| cagcgcagcc | tggaagcggc | actcgacgcg | ctcaatggcg | cccgcatccc | cgcgggcaag | 960 |
| atctatgacg | tcgccgatat | cgccagcgat | ccgcactacc | gtgcgcgcga | catgatcctg | 1020 |
| gacgcgcaat | tgccggacgg | cacccccgtc | cagttgcccg | gcatcgtgcc | gaagctgagc | 1080 |
| gccaccccg | gcgcactgcc | caaccccgcc | ccgcgcttg | gccagcatac | cgacgcggtg | 1140 |
| ctggaaggcc | ttggcatcgg | cacggcacag | cgcgaggcat | ggcgcatggc | agggattatc | 1200 |
| tga | | | | | | 1203 |

<210> SEQ ID NO 35
<211> LENGTH: 400
<212> TYPE: PRT
<213> ORGANISM: Artificial sequence
<220> FEATURE:
<223> OTHER INFORMATION: Synthetic

<400> SEQUENCE: 35

Met Glu Thr Ser Lys Ser Lys Pro Leu Ala Gly Val Arg Val Leu Glu
1               5                   10                  15

Leu Gly Gln Leu Ile Ala Gly Pro Phe Ala Ala Arg Met Leu Ala Ala
            20                  25                  30

Phe Gly Ala Glu Val Ile Lys Val Glu Pro Pro Gly Thr Gly Asp Pro
        35                  40                  45

Leu Arg Lys Trp Arg Leu Leu His Glu Gly Thr Ser Val Trp Trp Glu
    50                  55                  60

Ala Gln Ser Arg Asp Lys Gln Ser Val Thr Leu Asp Leu Arg Thr Pro
 65                  70                  75                  80

Gln Gly Gln Glu Val Arg Lys Leu Ala Gln Ser Asp Val Leu
             85                  90                  95

Ile Glu Asn Phe Arg Pro Gly Thr Leu Glu Gly Trp Gly Leu Gly Trp
            100                 105                 110

Asp Ser Leu Cys Ala Ala Asn Pro Gly Leu Val Met Leu Arg Val Ser
            115                 120                 125

Gly Tyr Gly Gln Thr Gly Pro Tyr Arg Asp Arg Pro Gly Phe Gly Val
            130                 135                 140

Ile Gly Glu Ala Met Gly Gly Leu Arg His Leu Ser Gly Glu Pro Gly
145                 150                 155                 160

Arg Thr Pro Val Arg Val Gly Val Ser Met Gly Asp Ser Leu Ser Ala
                165                 170                 175

Leu His Gly Val Ile Gly Ile Leu Leu Ala Leu Arg His Arg Glu Gln
                180                 185                 190

Asn Gly Gly Gln Gly Gln Val Val Asp Val Ala Leu Tyr Glu Ser Val
            195                 200                 205

Phe Ser Met Met Glu Ser Leu Leu Pro Glu Tyr Ser Val Phe Gly Ala
210                 215                 220

Val Arg Gln Ala Ala Gly Ser Ser Leu Pro Gly Ile Ala Pro Thr Asn
225                 230                 235                 240

Ala Tyr Arg Cys Ala Asp Gly Lys Tyr Val Leu Ile Ala Gly Asn Gly
                245                 250                 255

Asp Gly Ile Phe Arg Arg Leu Met Asp Met Ile Glu Arg Pro Asp Leu
            260                 265                 270

Arg Asp Asp Pro Ala Leu Ala His Asn Asp Gly Arg Val Ser Gln Val
            275                 280                 285

Ala Met Leu Asp Ala Ala Ile Gly Glu Trp Ala Ala Gln Arg Ser Leu
            290                 295                 300

Glu Ala Ala Leu Asp Ala Leu Asn Gly Ala Arg Ile Pro Ala Gly Lys
305                 310                 315                 320

Ile Tyr Asp Val Ala Asp Ile Ala Ser Asp Pro His Tyr Arg Ala Arg
                325                 330                 335

Asp Met Ile Leu Asp Ala Gln Leu Pro Asp Gly Thr Pro Val Gln Leu
            340                 345                 350

Pro Gly Ile Val Pro Lys Leu Ser Ala Thr Pro Gly Ala Leu Pro Asn
            355                 360                 365

Pro Ala Pro Ala Leu Gly Gln His Thr Asp Ala Val Leu Glu Gly Leu
            370                 375                 380

Gly Ile Gly Thr Ala Gln Arg Glu Ala Trp Arg Met Ala Gly Ile Ile
385                 390                 395                 400

<210> SEQ ID NO 36
<211> LENGTH: 867
<212> TYPE: DNA
<213> ORGANISM: Artificial sequence
<220> FEATURE:
<223> OTHER INFORMATION: Synthetic

<400> SEQUENCE: 36
atgactgacg ccactcctga actcgaacgc ctgcgcggct ggatcggccg cagcgaatcg    60
cgcaccgaaa cgctgtcgcc ggaaccggtg atcggcctcg ccgccacctt cgacctcgac   120
cccgaggccg tcgccgccgg cccgctgccg ccgctgtggc actggctcta cttcctgccg   180

```
cgcgcgccgc agcgtgaact gggacgcgac ggccatccca ccctcggcgg cttcatgccg      240
ccggtgccgc tgccgcgccg catgtgggcc ggcagcgaac tgagcttcag ccatccactg      300
catatcggcg ataccgtcac gcgcacctcc accatcaagg acgtgcagta caagaccggg      360
cgcaccggtg aactgtggtt tgtcgccgtc gatcacgagc tgaccgtcaa cggcaagacc      420
gcggtcaacg agcgccacga tatcgtctac cgcgccatgc ccgacccgtc caggccgcag      480
ccgccgcgcc cgcgcctgga gcaggccgcg cagtggcagc gcacgctgca ggcagatccg      540
gtgatgctgt tccgctactc ggcactgacc ttcaacggcc accgcatcca ctatgaccgc      600
cagtacacgc gcgaggtcga gggctacccc ggcctggtgg tgcacgggcc gatgcaggcc      660
atgctgatgc tggacctggt ggcgcgcgag caaccgcagg cgcgcgtgcg ccgctttggc      720
ttccgcggcc tggcgccgct gttcgaccag gacaccatca tcgttggcgg cgcggctgat      780
ccggcgcagg ctgggcggct ggtgctgtgg acggggacg atgccggcgg gcaggcgatg      840
caggggtggg cggaagtgga aggttaa                                          867
```

<210> SEQ ID NO 37
<211> LENGTH: 288
<212> TYPE: PRT
<213> ORGANISM: Artificial sequence
<220> FEATURE:
<223> OTHER INFORMATION: Synthetic

<400> SEQUENCE: 37

```
Met Thr Asp Ala Thr Pro Glu Leu Glu Arg Leu Arg Gly Trp Ile Gly
1               5                   10                  15

Arg Ser Glu Ser Arg Thr Glu Thr Leu Ser Pro Glu Pro Val Ile Gly
                20                  25                  30

Leu Ala Ala Thr Phe Asp Leu Asp Pro Glu Ala Val Ala Ala Gly Pro
            35                  40                  45

Leu Pro Pro Leu Trp His Trp Leu Tyr Phe Leu Pro Arg Ala Pro Gln
        50                  55                  60

Arg Glu Leu Gly Arg Asp Gly His Pro Thr Leu Gly Gly Phe Met Pro
65                  70                  75                  80

Pro Val Pro Leu Pro Arg Arg Met Trp Ala Gly Ser Glu Leu Ser Phe
                85                  90                  95

Ser His Pro Leu His Ile Gly Asp Thr Val Thr Arg Thr Ser Thr Ile
            100                 105                 110

Lys Asp Val Gln Tyr Lys Thr Gly Arg Thr Gly Glu Leu Trp Phe Val
        115                 120                 125

Ala Val Asp His Glu Leu Thr Val Asn Gly Lys Thr Ala Val Asn Glu
    130                 135                 140

Arg His Asp Ile Val Tyr Arg Ala Met Pro Asp Pro Ser Arg Pro Gln
145                 150                 155                 160

Pro Pro Arg Pro Arg Leu Glu Gln Ala Ala Gln Trp Gln Arg Thr Leu
                165                 170                 175

Gln Ala Asp Pro Val Met Leu Phe Arg Tyr Ser Ala Leu Thr Phe Asn
            180                 185                 190

Gly His Arg Ile His Tyr Asp Arg Gln Tyr Thr Arg Glu Val Glu Gly
        195                 200                 205

Tyr Pro Gly Leu Val Val His Gly Pro Met Gln Ala Met Leu Met Leu
    210                 215                 220

Asp Leu Val Ala Arg Glu Gln Pro Gln Ala Arg Val Arg Arg Phe Gly
225                 230                 235                 240
```

Phe Arg Gly Leu Ala Pro Leu Phe Asp Gln Asp Thr Ile Ile Val Gly
            245                 250                 255

Gly Ala Ala Asp Pro Ala Gln Ala Gly Arg Leu Val Leu Trp Thr Gly
        260                 265                 270

Asp Asp Ala Gly Gly Gln Ala Met Gln Gly Trp Ala Glu Val Glu Gly
    275                 280                 285

<210> SEQ ID NO 38
<211> LENGTH: 825
<212> TYPE: DNA
<213> ORGANISM: Artificial sequence
<220> FEATURE:
<223> OTHER INFORMATION: Synthetic

<400> SEQUENCE: 38
atgtccactg cagtcaccta cctgttcgtg ccgggcgacc ggccggaacg cttcgacaag      60
gccgctgccg ccggccccga tgtgatgatc ctggacctcg aggacgcggt ccatccggac     120
gccaagcccg ccgcgcgcgc agccatcgcc gcgtggctgg ccggactgcc cgcggccaat     180
gcctttgtcc gcatcaacga cagcgcctcg ccgtcctttg ccgccgacct ggcctggctg     240
cgcgcgctgc ccccgggtac cgcgctggca ggcctgctgg tgcccaaggc agaagatgcc     300
gccgcgctgg ccaccatcgc gcaggccctg cactcgatca acccgcaggg cgaactggtc     360
gcgatcatcg aaaccgcgct gggcctgcat cagatcgacg ccgtggccac cgccaccggc     420
gtggcacgtc ttgccttcgg ctcgctcgac tatgcggtcg acctgggctg cagccatacg     480
cgcgacgcgc tcgcctttgc acgcgcgcgc atcgtgctgg cctcacgcgt ggccgggctg     540
ccgccgccgg tcgacggcgt gaccaccgca ctgaaagacg aagccgtgct ggccagcgac     600
gttgcctatg cgcgcgaact cggctttgcc ggcaagctct gcatccaccc ggcccagctg     660
ggcgcggcgc gcgcaggctt cctgcccagc ccgagcagc tcgactgggc cgccgtgtg      720 ctggaagcta ccgccagcgg cagccatgcg gtgcaggtca tggcaagat ggtggaccgg     780 cccgtgatcg agcaggcccg ccggctgctg gcactggcgc aataa                    825

<210> SEQ ID NO 39
<211> LENGTH: 274
<212> TYPE: PRT
<213> ORGANISM: Artificial sequence
<220> FEATURE:
<223> OTHER INFORMATION: Synthetic

<400> SEQUENCE: 39

Met Ser Thr Ala Val Thr Tyr Leu Phe Val Pro Gly Asp Arg Pro Glu
1               5                   10                  15

Arg Phe Asp Lys Ala Ala Ala Ala Gly Pro Asp Val Met Ile Leu Asp
            20                  25                  30

Leu Glu Asp Ala Val His Pro Asp Ala Lys Pro Ala Ala Arg Ala Ala
        35                  40                  45

Ile Ala Ala Trp Leu Ala Gly Leu Pro Ala Ala Asn Ala Phe Val Arg
    50                  55                  60

Ile Asn Asp Ser Ala Ser Pro Ser Phe Ala Ala Asp Leu Ala Trp Leu
65                  70                  75                  80

Arg Ala Leu Pro Pro Gly Thr Ala Leu Ala Gly Leu Leu Val Pro Lys
                85                  90                  95

Ala Glu Asp Ala Ala Ala Leu Ala Thr Ile Ala Gln Ala Leu His Ser
            100                 105                 110

Ile Asn Pro Gln Gly Glu Leu Val Ala Ile Glu Thr Ala Leu Gly
    115                 120                 125

Leu His Gln Ile Asp Ala Val Ala Thr Ala Thr Gly Val Ala Arg Leu
130                 135                 140

Ala Phe Gly Ser Leu Asp Tyr Ala Val Asp Leu Gly Cys Ser His Thr
145                 150                 155                 160

Arg Asp Ala Leu Ala Phe Ala Arg Ala Arg Ile Val Leu Ala Ser Arg
                165                 170                 175

Val Ala Gly Leu Pro Pro Pro Val Asp Gly Val Thr Thr Ala Leu Lys
            180                 185                 190

Asp Glu Ala Val Leu Ala Ser Asp Val Ala Tyr Ala Arg Glu Leu Gly
            195                 200                 205

Phe Ala Gly Lys Leu Cys Ile His Pro Ala Gln Leu Gly Ala Ala Arg
        210                 215                 220

Ala Gly Phe Leu Pro Ser Pro Glu Gln Leu Asp Trp Ala Arg Arg Val
225                 230                 235                 240

Leu Glu Ala Thr Ala Ser Gly Ser His Ala Val Gln Val Asp Gly Lys
                245                 250                 255

Met Val Asp Arg Pro Val Ile Glu Gln Ala Arg Arg Leu Leu Ala Leu
            260                 265                 270

Ala Gln

<210> SEQ ID NO 40
<211> LENGTH: 1197
<212> TYPE: DNA
<213> ORGANISM: Artificial sequence
<220> FEATURE:
<223> OTHER INFORMATION: Synthetic

<400> SEQUENCE: 40

| | | | | | |
|---|---|---|---|---|---|
| atgtcccatt | cccccaaagg | catccgcccg | ctcgacggca | tccgcgtggt | ctcgctcgag | 60 |
| cacgccgtgg | ccgcgccctt | cgccacgcgc | cagctggccg | accttggtgc | ccgcgtcatc | 120 |
| aagatcgagc | gccccggagt | gggcgacttc | gcgcgcggct | atgaccagtc | cgtgcacggc | 180 |
| caggcctcgt | actttgtgtg | gcttaaccgg | ggcaaggaaa | gcctgaccct | ggatctgaag | 240 |
| gatcgagagg | cgcaggccat | cctgcaccgg | ctgctggccg | atgccgatgt | gctggtgcag | 300 |
| aacctcgccc | ccgcgcggc | agtgcgcatg | ggcctggact | cgacagcct | gcacggcaag | 360 |
| tacgacaagc | tcatcgtctg | tgacatctcg | ggctatggcg | actccggtcc | ctatcgcgac | 420 |
| aagaaggcct | acgacctgct | gatccaggcc | gccgccggcc | tggtgggcct | caccggcgga | 480 |
| ccgaacgagc | cgtcgcgcgc | cggcgtttcg | atcgccgaca | tctcggccgg | catgtacgcc | 540 |
| tacagcggca | tcctttcggc | gctgctgcag | cgtggccgca | ccggcaaggg | cctgcgcgtg | 600 |
| caggtgacca | tgctcgaggc | gatggccgag | tggatgaacc | aggtcctcta | cttcggccac | 660 |
| tacgccggca | agccgccggg | acgcttcggc | gcttcgcatc | cgaccatcgc | ccgtatggc | 720 |
| gtgcatcgca | ccggcaatgg | cagcgtgatc | ttcagcgtgc | agaacgaacg | cgagttcgcc | 780 |
| aatttctgcg | agatcgtgct | cggcaaccgg | gaactggcgc | aggacgaacg | cttctccagc | 840 |
| aatacggccc | gtgtgcacaa | tcgccccgaa | ctcaccgcca | tcatcgaaga | gcgcttcgcg | 900 |
| ccgatgactg | tggcgcaggc | cgaggcactg | ctcgacgagg | cgcagatcgc | caatgccccg | 960 |
| atgaacgaca | tcgagggcgt | atggaaccat | ccgcagttgc | aggcacgcca | gcgctggcgc | 1020 |
| gaagtggcca | ccccgggcgg | tccgatcggc | gcgctgctgc | cgcccgccaa | cctgtcgggc | 1080 |
| gtggagcctg | tcatgggcga | cgtaccggca | ctgggcgcgc | acagccggca | gatcctggcc | 1140 | gagctcggct atgacgacgg cgatatcgcc gcgctggctg acaagcggac catctga   1197

<210> SEQ ID NO 41
<211> LENGTH: 398
<212> TYPE: PRT
<213> ORGANISM: Artificial sequence
<220> FEATURE:
<223> OTHER INFORMATION: Synthetic

<400> SEQUENCE: 41

Met Ser His Ser Pro Lys Gly Ile Arg Pro Leu Asp Gly Ile Arg Val
1               5                   10                  15

Val Ser Leu Glu His Ala Val Ala Pro Phe Ala Thr Arg Gln Leu
            20                  25                  30

Ala Asp Leu Gly Ala Arg Val Ile Lys Ile Glu Arg Pro Gly Val Gly
            35                  40                  45

Asp Phe Ala Arg Gly Tyr Asp Gln Ser Val His Gly Gln Ala Ser Tyr
    50                  55                  60

Phe Val Trp Leu Asn Arg Gly Lys Glu Ser Leu Thr Leu Asp Leu Lys
65                  70                  75                  80

Asp Arg Glu Ala Gln Ala Ile Leu His Arg Leu Leu Ala Asp Ala Asp
                85                  90                  95

Val Leu Val Gln Asn Leu Ala Pro Gly Ala Ala Val Arg Met Gly Leu
            100                 105                 110

Asp Phe Asp Ser Leu His Gly Lys Tyr Asp Lys Leu Ile Val Cys Asp
    115                 120                 125

Ile Ser Gly Tyr Gly Asp Ser Gly Pro Tyr Arg Asp Lys Lys Ala Tyr
130                 135                 140

Asp Leu Leu Ile Gln Ala Ala Gly Leu Val Gly Leu Thr Gly Gly
145                 150                 155                 160

Pro Asn Glu Pro Ser Arg Ala Gly Val Ser Ile Ala Asp Ile Ser Ala
                165                 170                 175

Gly Met Tyr Ala Tyr Ser Gly Ile Leu Ser Ala Leu Leu Gln Arg Gly
            180                 185                 190

Arg Thr Gly Lys Gly Leu Arg Val Gln Val Thr Met Leu Glu Ala Met
        195                 200                 205

Ala Glu Trp Met Asn Gln Val Leu Tyr Phe Gly His Tyr Gly Gly Lys
    210                 215                 220

Pro Pro Gly Arg Phe Gly Ala Ser His Pro Thr Ile Ala Pro Tyr Gly
225                 230                 235                 240

Val His Arg Thr Gly Asn Gly Ser Val Ile Phe Ser Val Gln Asn Glu
                245                 250                 255

Arg Glu Phe Ala Asn Phe Cys Glu Ile Val Leu Gly Asn Arg Glu Leu
            260                 265                 270

Ala Gln Asp Glu Arg Phe Ser Ser Asn Thr Ala Arg Val His Asn Arg
        275                 280                 285

Pro Glu Leu Thr Ala Ile Ile Glu Glu Arg Phe Ala Pro Met Thr Val
    290                 295                 300

Ala Gln Ala Glu Ala Leu Leu Asp Glu Ala Gln Ile Ala Asn Ala Pro
305                 310                 315                 320

Met Asn Asp Ile Glu Gly Val Trp Asn His Pro Gln Leu Gln Ala Arg
                325                 330                 335

Gln Arg Trp Arg Glu Val Ala Thr Pro Gly Gly Pro Ile Gly Ala Leu
            340                 345                 350

```
Leu Pro Pro Ala Asn Leu Ser Gly Val Glu Pro Val Met Gly Asp Val
            355                 360                 365

Pro Ala Leu Gly Ala His Ser Arg Gln Ile Leu Ala Glu Leu Gly Tyr
        370                 375                 380

Asp Asp Gly Asp Ile Ala Ala Leu Ala Asp Lys Arg Thr Ile
385                 390                 395
```

<210> SEQ ID NO 42
<211> LENGTH: 1245
<212> TYPE: DNA
<213> ORGANISM: Artificial sequence
<220> FEATURE:
<223> OTHER INFORMATION: Synthetic

<400> SEQUENCE: 42

```
atggcgggca gccaggccgc ggcgcacggc gcgcttgccg gcgtgcgggt gctggacctg      60
tcgcgcatcc tggccggtcc ctggtgcgcg cagaacctgg cggacctggg cgccgaagtc     120
atcaaggtgg agcggcccgg cgcgggcgac gacacccgtt cgtggggcc gccctggctg      180 cccggcgcgg acgggcagcc gtcgcgcgac gccacctact ttgccggcgc caaccgcggc     240
aagcagtcgg tgacgctcga tatcgccagc ccgcaagggc aggagattgt gcgcgaactg     300
gcggccaagt cgcagatcgt gctggagaac tacaaggtcg gcgacctgaa cgctacgggg     360
ctggactatg acagcctcaa ggcgatcaac ccgtccatcg tctactgctc gatcacgggc     420
tacggccaga ccgggccgag cgcgcacaag cccggctatg acttcatctt ccagggcctg     480 ggcgcctga tgagcgtcac cggcgagcgc gacgacctgc ccggcggcgg gccgcagaag     540
gtgggcgtgg cggtggtcga catgcttacc ggcatgtatg ccaccgtggc cgtgctggcc     600
gcgttgcgcc atgccgagcg caccggcgag ggccagcata tcgacatggc gctgctcgat     660
gcggtggtgg cggtcggcgc cacgccgatc atcgcccagc gcgtgaccgg caaggccatg     720
ccgcgctacg gcaatgcgca cgccaatatg gtgccctacc atgtgttcgc caccgccgac     780
ggctacatga tcgtggcggc cggtaacgac gggcagtggc aggcgtattg ccgcggcgtc     840
gagcgtcccg acctggccgc cgacgagcgc tttgccaccg gccccggccg catcatccat     900
cgcgacacgc tggtgccgct gctcgaggcg catatgcgca cgcggccgac ggcgcactgg     960
gtgcaggcgc tggaagcgca gggcatcccg tgcggccga tcaacgacta cggccaggtg    1020
ctggaagacc cgcaggtgcg gcatcgcgag ctgcaggtcg acctggtgcg cgacgacggc    1080
agcctgtgcc cgaccgtcaa gagcccgttg cggctgtcgg caaccccggt gcaatacgac    1140
gcaccgccgc cgcggctggg cgagcatacc gaacaggtgc tggaatcggt gctgggtatg    1200
tcggccgagc gcatcgccag gctgcgcgag caaggcgtgg tctga                    1245
```

<210> SEQ ID NO 43
<211> LENGTH: 414
<212> TYPE: PRT
<213> ORGANISM: Artificial sequence
<220> FEATURE:
<223> OTHER INFORMATION: Synthetic

<400> SEQUENCE: 43

```
Met Ala Gly Ser Gln Ala Ala His Gly Ala Leu Ala Gly Val Arg
1               5                   10                  15

Val Leu Asp Leu Ser Arg Ile Leu Ala Gly Pro Trp Cys Ala Gln Asn
            20                  25                  30

Leu Ala Asp Leu Gly Ala Glu Val Ile Lys Val Glu Arg Pro Gly Ala
        35                  40                  45
```

Gly Asp Asp Thr Arg Ser Trp Gly Pro Pro Trp Leu Pro Gly Ala Asp
             50                  55                  60

Gly Gln Pro Ser Arg Asp Ala Thr Tyr Phe Ala Gly Ala Asn Arg Gly
 65                  70                  75                  80

Lys Gln Ser Val Thr Leu Asp Ile Ala Ser Pro Gln Gly Gln Glu Ile
                 85                  90                  95

Val Arg Glu Leu Ala Ala Lys Ser Gln Ile Val Leu Glu Asn Tyr Lys
            100                 105                 110

Val Gly Asp Leu Lys Arg Tyr Gly Leu Asp Tyr Asp Ser Leu Lys Ala
            115                 120                 125

Ile Asn Pro Ser Ile Val Tyr Cys Ser Ile Thr Gly Tyr Gly Gln Thr
130                 135                 140

Gly Pro Ser Ala His Lys Pro Gly Tyr Asp Phe Ile Phe Gln Gly Leu
145                 150                 155                 160

Gly Gly Leu Met Ser Val Thr Gly Glu Arg Asp Asp Leu Pro Gly Gly
                165                 170                 175

Gly Pro Gln Lys Val Gly Val Ala Val Val Asp Met Leu Thr Gly Met
            180                 185                 190

Tyr Ala Thr Val Ala Val Leu Ala Ala Leu Arg His Ala Glu Arg Thr
            195                 200                 205

Gly Glu Gly Gln His Ile Asp Met Ala Leu Leu Asp Ala Val Val Ala
210                 215                 220

Val Gly Ala Thr Pro Ile Ile Ala Gln Arg Val Thr Gly Lys Ala Met
225                 230                 235                 240

Pro Arg Tyr Gly Asn Ala His Ala Asn Met Val Pro Tyr His Val Phe
                245                 250                 255

Ala Thr Ala Asp Gly Tyr Met Ile Val Ala Ala Gly Asn Asp Gly Gln
            260                 265                 270

Trp Gln Ala Tyr Cys Arg Gly Val Glu Arg Pro Asp Leu Ala Ala Asp
            275                 280                 285

Glu Arg Phe Ala Thr Gly Pro Gly Arg Ile Ile His Arg Asp Thr Leu
290                 295                 300

Val Pro Leu Leu Glu Ala His Met Arg Thr Arg Pro Thr Ala His Trp
305                 310                 315                 320

Val Gln Ala Leu Glu Ala Gln Gly Ile Pro Cys Gly Pro Ile Asn Asp
                325                 330                 335

Tyr Gly Gln Val Leu Glu Asp Pro Gln Val Arg His Arg Glu Leu Gln
            340                 345                 350

Val Asp Leu Val Arg Asp Asp Gly Ser Leu Cys Pro Thr Val Lys Ser
            355                 360                 365

Pro Leu Arg Leu Ser Ala Thr Pro Val Gln Tyr Asp Ala Pro Pro Pro
370                 375                 380

Arg Leu Gly Glu His Thr Glu Gln Val Leu Glu Ser Val Leu Gly Met
385                 390                 395                 400

Ser Ala Glu Arg Ile Ala Arg Leu Arg Glu Gln Gly Val Val
            405                 410

<210> SEQ ID NO 44
<211> LENGTH: 1224
<212> TYPE: DNA
<213> ORGANISM: Artificial sequence
<220> FEATURE:
<223> OTHER INFORMATION: Synthetic

<400> SEQUENCE: 44

```
atgctgccgc ttgcaggcat ccgcgtggtc gacctgtcca ccgtggtgat ggggccgtat      60
gccagccagt ggctggccga ccttggcgcc gaggtgatca aggtcgagcc gcccgaaggc     120
gattccacgc gccgcaccgg ccccgccgcc gagcccggca tggcggccat tttcctgggc     180
gtgaaccgca gcaagcgcag cgtggtgctg gacctgaagc agccggccgc gcaggccgcg     240
ctggaccgcg tgctggccgg cgccgacgtg ctgatgcaca gcatgcgccc gcaaaagctg     300
gccgcactgg ggctggcacc cgacgacgtg cgggcgcgcc acccggagct ggtctttgtc     360
agcctgctcg gctttgccga ggaaggcccc tatggcggcc gcccggcgta cgacgacatc     420
atccagggcc tgtcgggcaa tgccgcgctg atggcggcgc aaaccggcga cagccgctac     480
ttccctacca tcgccgcgga caagaccagc gggctggtgg ccgcgctgtc ggtctgcgcg     540
gcgctggccg ggcgcgcgcg gcgcaatgcc gatggcggca cggccacgg cacgctggtc      600
gaagtgccga tgttcgaatc catggtcgcc ttcaacctgg tcgagcactt ctacggccgc     660
catttcgagc cgccgcgcgg ccccagcggc tatccgcgcg tgctggcacc gctgcgccgc     720
ccgtaccgca gcgccgacgg ctatgtctgc atgatgccgt acaccgacgc gcactggtgc     780
gacttcttcc acgccgccgg cgccccgag ctggccgccg atgcgcgctt tgccgacatc      840
gcggcacgca cgcggcatat cgagacgctg tacgagctca ccggcgaaat cgtgcacgga     900
cagaccaccg cgcactgggt tgacctgtgc gaacgcctgc agatcccggt ggcgcgcatc     960
aatgaactcg acgacctgcc ggccgatccg cacctggccg ccactggctt cttcgaaacc    1020
gtcgaagacc cggccatggg cacgctgcgt tttcccggcg cgccggtgcg tttcgacagc    1080
cagcgcgcgc cgctgggcat cccgccgcgg ctgggcgagc acaccgcgag cgtgctggcc    1140
caggcgggac tgtccgcaga agcgatcgcg caattgcaac taagcggtgc cgcacgctgc    1200
gcacccgcca aggagacacc atga                                          1224
```

<210> SEQ ID NO 45
<211> LENGTH: 407
<212> TYPE: PRT
<213> ORGANISM: Artificial sequence
<220> FEATURE:
<223> OTHER INFORMATION: Synthetic

<400> SEQUENCE: 45

```
Met Leu Pro Leu Ala Gly Ile Arg Val Val Asp Leu Ser Thr Val Val
1               5                   10                  15

Met Gly Pro Tyr Ala Ser Gln Trp Leu Ala Asp Leu Gly Ala Glu Val
            20                  25                  30

Ile Lys Val Glu Pro Pro Glu Gly Asp Ser Thr Arg Arg Thr Gly Pro
        35                  40                  45

Ala Ala Glu Pro Gly Met Ala Ala Ile Phe Leu Gly Val Asn Arg Ser
    50                  55                  60

Lys Arg Ser Val Val Leu Asp Leu Lys Gln Pro Ala Ala Gln Ala Ala
65                  70                  75                  80

Leu Asp Arg Val Leu Ala Gly Ala Asp Val Leu Met His Ser Met Arg
                85                  90                  95

Pro Gln Lys Leu Ala Ala Leu Gly Leu Ala Pro Asp Asp Val Arg Ala
            100                 105                 110

Arg His Pro Glu Leu Val Phe Val Ser Leu Leu Gly Phe Ala Glu Glu
        115                 120                 125

Gly Pro Tyr Gly Gly Arg Pro Ala Tyr Asp Asp Ile Ile Gln Gly Leu
    130                 135                 140
```

Ser Gly Asn Ala Ala Leu Met Ala Ala Gln Thr Gly Asp Ser Arg Tyr
145                 150                 155                 160

Phe Pro Thr Ile Ala Ala Asp Lys Thr Ser Gly Leu Val Ala Ala Leu
            165                 170                 175

Ser Val Cys Ala Ala Leu Ala Gly Arg Ala Arg Arg Asn Ala Asp Gly
        180                 185                 190

Gly Ser Gly His Gly Thr Leu Val Glu Val Pro Met Phe Glu Ser Met
    195                 200                 205

Val Ala Phe Asn Leu Val Glu His Phe Tyr Gly Arg His Phe Glu Pro
210                 215                 220

Pro Arg Gly Pro Ser Gly Tyr Pro Arg Val Leu Ala Pro Leu Arg Arg
225                 230                 235                 240

Pro Tyr Arg Ser Ala Asp Gly Tyr Val Cys Met Met Pro Tyr Thr Asp
                245                 250                 255

Ala His Trp Cys Asp Phe Phe His Ala Ala Gly Arg Pro Glu Leu Ala
            260                 265                 270

Ala Asp Ala Arg Phe Ala Asp Ile Ala Ala Arg Thr Arg His Ile Glu
        275                 280                 285

Thr Leu Tyr Glu Leu Thr Gly Glu Ile Val His Gly Gln Thr Thr Ala
    290                 295                 300

His Trp Val Asp Leu Cys Glu Arg Leu Gln Ile Pro Val Ala Arg Ile
305                 310                 315                 320

Asn Glu Leu Asp Asp Leu Pro Ala Asp Pro His Leu Ala Ala Thr Gly
                325                 330                 335

Phe Phe Glu Thr Val Glu Asp Pro Ala Met Gly Thr Leu Arg Phe Pro
            340                 345                 350

Gly Ala Pro Val Arg Phe Asp Ser Gln Arg Ala Pro Leu Gly Ile Pro
        355                 360                 365

Pro Arg Leu Gly Glu His Thr Ala Ser Val Leu Ala Gln Ala Gly Leu
    370                 375                 380

Ser Ala Glu Ala Ile Ala Gln Leu Gln Leu Ser Gly Ala Ala Arg Cys
385                 390                 395                 400

Ala Pro Ala Lys Glu Thr Pro
                405

<210> SEQ ID NO 46
<211> LENGTH: 1224
<212> TYPE: DNA
<213> ORGANISM: Artificial sequence
<220> FEATURE:
<223> OTHER INFORMATION: Synthetic

<400> SEQUENCE: 46
atgacgaacc ggcaagacct gccgctggca ggcatacgcg tggcggagtt cgggcagttc      60
atcgcggcgc cgggcgcggc catgatgctg gccgacctgg cgccgacgt ggtcaaggtg     120 gaggccttgc gcggcgacag cgcgcggcgc tttgacggca ccagcccgca gagcccgatg     180
tacctggcct acaaccgcgg caagcgcggc atagcgctgg acctgcgcac gcccggcggg     240
ctggacgccg cacggcggct ggcgctggca agcgacgtgg tgctgcacaa cacccgcgcc     300
ggcgtgatgg aagcgctggg gctggacgcc gccacgctgc gcgggcgcg tcccgacctg     360 atccatgcct ccatcagcgg cttcggcacg cgtgggccgt cgcgcacgcg ccccgggctg     420
gatattgccg cgcaggccga gagcggcatg atgtccgtca ccggcgaggc cggcgggcag     480
ccgctgaagg ccggttttgc gctgatcgac gcggccaccg cgctggcgac cggcaacgcc     540

-continued

```
atcctggcgg cgctgttccg gcgcgagcgc accggcgccg gcgagaccat cgagacctcg      600
ctgctgtcgg tcggcgtgca gatgcaggcc cagctgtggg ccgagtacca gtgctccggc      660
gcgctgccgg tgcgcagcgg caacagccag cccaaggccg cgccggccgc ggatgtgatc      720
gcggtggcga cgggcatat cgtgctgtcg gcctatctcg acgagcactg gacgcgcctg       780
tgcgaggcca tcggccagcc ggcgctggcg cacgatccgc gctttgcctg caacgcgctg      840
cgcgtgcaga accgcccggc gctgctggcc atcctgcacg acgccatgcg ccacctcagc      900
ggcgacgccg cgcgcacgct gctggagcgc caccaggtgg tggtgggcgt ggtgcgcgac      960
taccaccagg tcaacgcgag ccccgacgtg cgcgccagtg gcgtgctgca agccgttgac     1020
gacggcgagg cggccagct ggagctgccg ggactgccct tcaccatggc cagcatgccg      1080
gcaggcgcga tgcccgcggt gccgcgcctc ggccagcata cgaccgaggt gctggccgag     1140
ctcggcttca cgccgcgga gattcacacc atggcccgcg ccggcgcgat cggcgtggaa      1200
caagcccggc aggagcccgc atga                                            1224
```

<210> SEQ ID NO 47
<211> LENGTH: 407
<212> TYPE: PRT
<213> ORGANISM: Artificial sequence
<220> FEATURE:
<223> OTHER INFORMATION: Synthetic

<400> SEQUENCE: 47

```
Met Thr Asn Arg Gln Asp Leu Pro Leu Ala Gly Ile Arg Val Ala Glu
1               5                   10                  15

Phe Gly Gln Phe Ile Ala Ala Pro Gly Ala Ala Met Met Leu Ala Asp
            20                  25                  30

Leu Gly Ala Asp Val Val Lys Val Glu Ala Leu Arg Gly Asp Ser Ala
        35                  40                  45

Arg Arg Phe Asp Gly Thr Ser Pro Gln Ser Pro Met Tyr Leu Ala Tyr
    50                  55                  60

Asn Arg Gly Lys Arg Gly Ile Ala Leu Asp Leu Arg Thr Pro Gly Gly
65                  70                  75                  80

Leu Asp Ala Ala Arg Leu Ala Leu Ala Ser Asp Val Val Leu His
                85                  90                  95

Asn Thr Arg Ala Gly Val Met Glu Ala Leu Gly Leu Asp Ala Ala Thr
                100                 105                 110

Leu Arg Ala Ala Arg Pro Asp Leu Ile His Ala Ser Ile Ser Gly Phe
            115                 120                 125

Gly Thr Arg Gly Pro Ser Arg Thr Arg Pro Gly Leu Asp Ile Ala Ala
        130                 135                 140

Gln Ala Glu Ser Gly Met Met Ser Val Thr Gly Glu Ala Gly Gly Gln
145                 150                 155                 160

Pro Leu Lys Ala Gly Phe Ala Leu Ile Asp Ala Ala Thr Ala Leu Ala
                165                 170                 175

Thr Gly Asn Ala Ile Leu Ala Ala Leu Phe Arg Arg Glu Arg Thr Gly
                180                 185                 190

Ala Gly Glu Thr Ile Glu Thr Ser Leu Leu Ser Val Gly Val Gln Met
            195                 200                 205

Gln Ala Gln Leu Trp Ala Glu Tyr Gln Cys Ser Gly Ala Leu Pro Val
    210                 215                 220

Arg Ser Gly Asn Ser Gln Pro Lys Ala Ala Pro Ala Ala Asp Val Ile
225                 230                 235                 240
```

Ala Val Ala Asp Gly His Ile Val Leu Ser Ala Tyr Leu Asp Glu His
            245                 250                 255

Trp Thr Arg Leu Cys Glu Ala Ile Gly Gln Pro Ala Leu Ala His Asp
        260                 265                 270

Pro Arg Phe Ala Cys Asn Ala Leu Arg Val Gln Asn Arg Pro Ala Leu
    275                 280                 285

Leu Ala Ile Leu His Asp Ala Met Arg His Leu Ser Gly Asp Ala Ala
290                 295                 300

Arg Thr Leu Leu Glu Arg His Gln Val Val Gly Val Val Arg Asp
305                 310                 315                 320

Tyr His Gln Val Asn Ala Ser Pro Asp Val Arg Ala Ser Gly Val Leu
                325                 330                 335

Gln Ala Val Asp Asp Gly Glu Gly Gly Gln Leu Glu Leu Pro Gly Leu
            340                 345                 350

Pro Phe Thr Met Ala Ser Met Pro Ala Gly Ala Met Pro Ala Val Pro
        355                 360                 365

Arg Leu Gly Gln His Thr Thr Glu Val Leu Ala Glu Leu Gly Phe Ser
    370                 375                 380

Ala Ala Glu Ile His Thr Met Arg Ala Gly Ala Ile Gly Val Glu
385                 390                 395                 400

Gln Ala Arg Gln Glu Pro Ala
            405

<210> SEQ ID NO 48
<211> LENGTH: 1197
<212> TYPE: DNA
<213> ORGANISM: Artificial sequence
<220> FEATURE:
<223> OTHER INFORMATION: Synthetic

<400> SEQUENCE: 48
gtgactcatt ccgacctgcc gcttgccggc atccgcgtga tcgatttctc gcgcgtgctg      60
gcgggccctt actgcacggc gctgctcggc gaccttggcg cagaggtgat caagatcgaa     120
ccgcctggcg gcgatgacta ccgcgcggtc ggtcccttcg tcgatggcaa gagcggtctg     180
ttctctgcca tgaaccgcaa caagcagagc atcgtgatcg acctgaagac ggcagcgggc     240
ctggagctgg cgcgctcgct ctgcgcccgg gccgacgtgg tggtcgagaa cttccgcccg     300
ggtgtcgcgg acaagctggg catcggctat gaggcgctgc gtgcgctgaa tccgccggtg     360
gtctacgcca gcgtgtcggg cttcggccag accggccgg aatcgcaccg tccggcctac     420
gacatcatcc tgcaggcaat gtgcgggctg atggatgcca ccggcgcccc ggacggcacc     480
ccgaccatgc tggcgaggc cgtctccgat gcggtcagcg gcctgttcgc tcatggggc     540 gtgctggccg cgctgctggc gcgcgagaag accggcgggg gcacgcatgt cgatgtctcg     600
atgttcgacg ccaccctgag cctgagcgcc accctggtcg cgcgctatgc gcgaccggc     660 ctggcgccgc tgcgcgtcgg caaccgccat ccctcgtccg cgccgttcgg cgtgtaccgc     720
gccgcggacg gcttctatgt ggtggcggtg ctgaacaaca agctgttcca ggcgctggcc     780
aatgccatcg gcggccgga gatggcgcag gacccgcgct tgccgacga cgagacgcgc     840 tgccgcttcg agggcgatct gcgcgccggt ctcgaagcct ggtcggccag ccgttccgtg     900
gccgaggtga accgcctgct gagcgaggcg gcatccctg tcgcgcctat ccgcaacgtc     960
aaggaagccc tggagagcga ccatgccgcc accgcggcc tgcttgccga agtgcccggg    1020
ccggagggcg gcaccgtgcg gttgccgtcg cagccggtga agttctccgg ctacggcgcc    1080

```
aaccgcgtga cgcccgcgcc ggcgctgggg cagcacaccg aagccatcct ggccgagctg    1140
gccaacgctg ccacggcgca tccgcaagtg ttcagcaagg agaaacaaca tgcataa      1197
```

<210> SEQ ID NO 49
<211> LENGTH: 398
<212> TYPE: PRT
<213> ORGANISM: Artificial sequence
<220> FEATURE:
<223> OTHER INFORMATION: Synthetic

<400> SEQUENCE: 49

```
Met Thr His Ser Asp Leu Pro Leu Ala Gly Ile Arg Val Ile Asp Phe
1               5                  10                  15

Ser Arg Val Leu Ala Gly Pro Tyr Cys Thr Ala Leu Leu Gly Asp Leu
            20                  25                  30

Gly Ala Glu Val Ile Lys Ile Glu Pro Pro Gly Gly Asp Asp Tyr Arg
        35                  40                  45

Ala Val Gly Pro Phe Val Asp Gly Lys Ser Gly Leu Phe Ser Ala Met
    50                  55                  60

Asn Arg Asn Lys Gln Ser Ile Val Ile Asp Leu Lys Thr Ala Ala Gly
65                  70                  75                  80

Leu Glu Leu Ala Arg Ser Leu Cys Ala Arg Ala Asp Val Val Glu
            85                  90                  95

Asn Phe Arg Pro Gly Val Ala Asp Lys Leu Gly Ile Gly Tyr Glu Ala
            100                 105                 110

Leu Arg Ala Leu Asn Pro Pro Val Val Tyr Ala Ser Val Ser Gly Phe
        115                 120                 125

Gly Gln Thr Gly Pro Glu Ser His Arg Pro Ala Tyr Asp Ile Ile Leu
    130                 135                 140

Gln Ala Met Cys Gly Leu Met Asp Ala Thr Gly Ala Pro Asp Gly Thr
145                 150                 155                 160

Pro Thr Met Leu Gly Glu Ala Val Ser Asp Ala Val Ser Gly Leu Phe
                165                 170                 175

Ala Ser Trp Gly Val Leu Ala Ala Leu Leu Ala Arg Glu Lys Thr Gly
            180                 185                 190

Arg Gly Thr His Val Asp Val Ser Met Phe Asp Ala Thr Leu Ser Leu
        195                 200                 205

Ser Ala Thr Leu Val Ala Arg Tyr Ala Ala Thr Gly Leu Ala Pro Leu
    210                 215                 220

Arg Val Gly Asn Arg His Pro Ser Ser Ala Pro Phe Gly Val Tyr Arg
225                 230                 235                 240

Ala Ala Asp Gly Phe Tyr Val Val Ala Val Leu Asn Asn Lys Leu Phe
                245                 250                 255

Gln Ala Leu Ala Asn Ala Ile Gly Arg Pro Glu Met Ala Gln Asp Pro
            260                 265                 270

Arg Phe Ala Asp Asp Glu Thr Arg Cys Arg Phe Glu Gly Asp Leu Arg
        275                 280                 285

Ala Gly Leu Glu Ala Trp Ser Ala Ser Arg Ser Val Ala Glu Val Asn
    290                 295                 300

Arg Leu Leu Ser Glu Ala Gly Ile Pro Val Ala Pro Ile Arg Asn Val
305                 310                 315                 320

Lys Glu Ala Leu Glu Ser Asp His Ala Ala His Arg Gly Leu Leu Ala
                325                 330                 335

Glu Val Pro Gly Pro Glu Gly Gly Thr Val Arg Leu Pro Ser Gln Pro
```

```
            340                 345                 350
Val Lys Phe Ser Gly Tyr Gly Ala Asn Arg Val Thr Pro Ala Pro Ala
        355                 360                 365

Leu Gly Gln His Thr Glu Ala Ile Leu Ala Glu Leu Ala Asn Ala Ala
    370                 375                 380

Thr Ala His Pro Gln Val Phe Ser Lys Glu Lys Gln His Ala
385                 390                 395
```

<210> SEQ ID NO 50
<211> LENGTH: 1251
<212> TYPE: DNA
<213> ORGANISM: Artificial sequence
<220> FEATURE:
<223> OTHER INFORMATION: Synthetic

<400> SEQUENCE: 50

```
atggagacac cgactggagc actcgctggc gtcaaggtcg tggacatcac ggcggtgttc      60
atgggcccct cggccactca gatgctcggc gacctcggcg cggatgtgat caaggtggag     120
ccgcccgcgg gcgatagcac ccgtggcatc gggccctgcg gcaatgagaa gatggggccg     180
cttttcctcg ggctgaaccg caacaagcgc agcatcgtgc tggacctgaa gtcgccgcag     240
gggcgcgagg cgctgctgcg cctggtggcg gatgcggacg tgctggcgta caacgtccgg     300
ccccaggcga tgcaacggct cgggctggac tacgagacgc tggcgcagat caatccgcgc     360
ctggtctatg tcggcatgtt cggcttctcg cagcgcggac gctatgcccc gcaagcggcg     420
ttcgacgacc tgatccaggc cgccaccggg ctgccccagg cggttgccat gggcaccggc     480
gacattccgc gctatcttcc gctgaccatt gccgaccgtt ccgtcggact ctatgccttc     540
ggcgtgatct cgccgcgcct ctacgcgcgg gcgacctccg gccgcggcca gcgcgtcgat     600
gtgccgatgt tcgaaaccat ggtgccttac gtgatgggcg accatctcta tggcgagacc     660
ttcgtgccag ccaagggcgg attcggttat ccacgcctgc tgtctcccga gcgccggcct     720
taccggaccc gcgacggcca tgtctgctgc ctgatctatc acgaccatca ctggcgtgcc     780
ttcctgaagg tgatcggcaa gcccggcctg tacgacaccg accgcgcttc gccgacatc      840
actacccgga cggcgcacat caccgagctc tacggcatgg tcagcgacga actggccagg     900
cggaccacgg aggaatggca agtgctgctg aaggaggcgg atatcccggt gttcccgatg     960
cacacctttg aatcgctgct cgatgatccg cacctgaatg catcggctt cttcagcgaa     1020
tccgaccacc cggcggtggg ccgcatccgc gaaatgtcgg tgcccagcga atggcacggg     1080
acgccgccat cgcagcgccg ccatgccccg gccctgggcg agcatagccg cgaagtgctg     1140
cgcgaggccg gctacaacga ggccgacatc gacagcctga tggcatccgg cgcatcgcgc     1200
gaaccgcgcc aggcatcggt gcatacggct ggcacggcaa gcgaggcctg a              1251
```

<210> SEQ ID NO 51
<211> LENGTH: 416
<212> TYPE: PRT
<213> ORGANISM: Artificial sequence
<220> FEATURE:
<223> OTHER INFORMATION: Synthetic

<400> SEQUENCE: 51

```
Met Glu Thr Pro Thr Gly Ala Leu Ala Gly Val Lys Val Val Asp Ile
1               5                   10                  15

Thr Ala Val Phe Met Gly Pro Ser Ala Thr Gln Met Leu Gly Asp Leu
            20                  25                  30
```

Gly Ala Asp Val Ile Lys Val Glu Pro Pro Ala Gly Asp Ser Thr Arg
         35                  40                  45

Gly Ile Gly Pro Cys Gly Asn Glu Lys Met Gly Pro Leu Phe Leu Gly
 50                  55                  60

Leu Asn Arg Asn Lys Arg Ser Ile Val Leu Asp Leu Lys Ser Pro Gln
 65                  70                  75                  80

Gly Arg Glu Ala Leu Leu Arg Leu Val Ala Asp Ala Asp Val Leu Ala
             85                  90                  95

Tyr Asn Val Arg Pro Gln Ala Met Gln Arg Leu Gly Leu Asp Tyr Glu
            100                 105                 110

Thr Leu Ala Gln Ile Asn Pro Arg Leu Val Tyr Val Gly Met Phe Gly
            115                 120                 125

Phe Ser Gln Arg Gly Arg Tyr Ala Pro Gln Ala Ala Phe Asp Asp Leu
130                 135                 140

Ile Gln Ala Ala Thr Gly Leu Pro Gln Ala Val Ala Met Gly Thr Gly
145                 150                 155                 160

Asp Ile Pro Arg Tyr Leu Pro Leu Thr Ile Ala Asp Arg Ser Val Gly
                165                 170                 175

Leu Tyr Ala Phe Gly Val Ile Cys Ala Ala Leu Tyr Ala Arg Ala Thr
            180                 185                 190

Ser Gly Arg Gly Gln Arg Val Asp Val Pro Met Phe Glu Thr Met Val
            195                 200                 205

Pro Tyr Val Met Gly Asp His Leu Tyr Gly Glu Thr Phe Val Pro Ala
            210                 215                 220

Lys Gly Gly Phe Gly Tyr Pro Arg Leu Leu Ser Pro Glu Arg Arg Pro
225                 230                 235                 240

Tyr Arg Thr Arg Asp Gly His Val Cys Cys Leu Ile Tyr His Asp His
                245                 250                 255

His Trp Arg Ala Phe Leu Lys Val Ile Gly Lys Pro Gly Leu Tyr Asp
            260                 265                 270

Thr Asp Pro Arg Phe Ala Asp Ile Thr Thr Arg Thr Ala His Ile Thr
            275                 280                 285

Glu Leu Tyr Gly Met Val Ser Asp Glu Leu Ala Arg Arg Thr Thr Glu
            290                 295                 300

Glu Trp Gln Val Leu Leu Lys Glu Ala Asp Ile Pro Val Phe Pro Met
305                 310                 315                 320

His Thr Phe Glu Ser Leu Leu Asp Asp Pro His Leu Asn Asp Ile Gly
                325                 330                 335

Phe Phe Ser Glu Ser Asp His Pro Ala Val Gly Arg Ile Arg Glu Met
            340                 345                 350

Ser Val Pro Ser Glu Trp His Gly Thr Pro Pro Ser Gln Arg Arg His
            355                 360                 365

Ala Pro Ala Leu Gly Glu His Ser Arg Glu Val Leu Arg Glu Ala Gly
            370                 375                 380

Tyr Asn Glu Ala Asp Ile Asp Ser Leu Met Ala Ser Gly Ala Ser Arg
385                 390                 395                 400

Glu Pro Arg Gln Ala Ser Val His Thr Ala Gly Thr Ala Ser Glu Ala
                405                 410                 415

<210> SEQ ID NO 52
<211> LENGTH: 1251
<212> TYPE: DNA
<213> ORGANISM: Artificial sequence
<220> FEATURE:
<223> OTHER INFORMATION: Synthetic

<400> SEQUENCE: 52

```
gtgaacctcc cactcaacgg catcaagatc atcgacttca cgcacgtcca ggccggtccc        60
gcctgcacgc agcttctcgc gtggttcggt gcggacgtga tcaaggtcga gcgccccggt       120
tccggcgacg tgacgcgcac ccagctgcgc gacatcccgg atgtcgatgc cctgtacttc       180
accatgctca acagcaacaa gcgcagcctg acgctggata ccaagaagcc ggaaggcaag       240
aagatcctgg agcagctgat ccgcgagtcg gacgtgctgg tcgagaactt cggcccgggc       300
gcgctggacc gcatggggtt ctcgtgggaa cgcatcaacg aactgaaccc gaagatgatc       360
gtggcttcgg tcaagggctt cagcgacggc caccactatg aagacctgaa ggtctacgag       420
aacgtggccc agtgcgccgg cggcgcggcc tcgaccaccg gcttctggga tggcccgccg       480
acggtgtccg ccgcggcgct gggcgattcc aacaccggca tgcacctggc catcggcatc       540
ctcaccgcgc tgatcggccg cgacaagacc ggcaagggcc agaaggtggc tgtgtcgatg       600
caggatgcgt gctgaacct gtgccgggtc aagctgcgcg accagcagcg cctggaccgc       660
ctgggctacc tggaggagta cccgcagtat ccgcacggca gcttcagcga cgtggtgccg       720
cgcggcggca acgcgggcgg cggcggccag ccgggctggg tgctgaagtg caagggtgg       780
gaaaccgacc ccaacgccta tatctacttc accatccagg ccatgcctg ggagccgatc       840
tgcaaggcgt gggcaagcc ggaatggatt tccgatccca actacgccac cgccaaggct       900
cgccagccgc atatcttcga tatcttcaac accatcgagg aatggctggc cgacaagacc       960
aagtacgagg ccgtggacat cctgcgcaag ttcgacatcc cgtgctcgcc ggtgctgtcg      1020
atgaaggaaa tcgccgccga tccgtcgctg cgcgccagcg gcagcatcac cgaggtgccg      1080
cacaaggagc gcggtaccta cctgacggtg ggcagcccga tcaagttctc cgacctcaag      1140
ccggagatca ccgggtcgcc actgctgggc gagcatagcg aagaggtgct ggccggcctg      1200
ggctacggcg cggacgacat caagcgcctg cgcgagtccc aggtgatctg a              1251
```

<210> SEQ ID NO 53
<211> LENGTH: 416
<212> TYPE: PRT
<213> ORGANISM: Artificial sequence
<220> FEATURE:
<223> OTHER INFORMATION: Synthetic

<400> SEQUENCE: 53

```
Met Asn Leu Pro Leu Asn Gly Ile Lys Ile Ile Asp Phe Thr His Val
1               5                   10                  15

Gln Ala Gly Pro Ala Cys Thr Gln Leu Leu Ala Trp Phe Gly Ala Asp
            20                  25                  30

Val Ile Lys Val Glu Arg Pro Gly Ser Gly Asp Val Thr Arg Thr Gln
        35                  40                  45

Leu Arg Asp Ile Pro Asp Val Asp Ala Leu Tyr Phe Thr Met Leu Asn
    50                  55                  60

Ser Asn Lys Arg Ser Leu Thr Leu Asp Thr Lys Lys Pro Glu Gly Lys
65                  70                  75                  80

Lys Ile Leu Glu Gln Leu Ile Arg Glu Ser Asp Val Leu Val Glu Asn
                85                  90                  95

Phe Gly Pro Gly Ala Leu Asp Arg Met Gly Phe Ser Trp Glu Arg Ile
            100                 105                 110

Asn Glu Leu Asn Pro Lys Met Ile Val Ala Ser Val Lys Gly Phe Ser
        115                 120                 125
```

Asp Gly His His Tyr Glu Asp Leu Lys Val Tyr Glu Asn Val Ala Gln
            130                 135                 140

Cys Ala Gly Ala Ala Ser Thr Thr Gly Phe Trp Asp Gly Pro Pro
145                 150                 155                 160

Thr Val Ser Ala Ala Leu Gly Asp Ser Asn Thr Gly Met His Leu
                165                 170                 175

Ala Ile Gly Ile Leu Thr Ala Leu Ile Gly Arg Asp Lys Thr Gly Lys
            180                 185                 190

Gly Gln Lys Val Ala Val Ser Met Gln Asp Ala Val Leu Asn Leu Cys
            195                 200                 205

Arg Val Lys Leu Arg Asp Gln Gln Arg Leu Asp Arg Leu Gly Tyr Leu
210                 215                 220

Glu Glu Tyr Pro Gln Tyr Pro His Gly Ser Phe Ser Asp Val Val Pro
225                 230                 235                 240

Arg Gly Gly Asn Ala Gly Gly Gly Gln Pro Gly Trp Val Leu Lys
                245                 250                 255

Cys Lys Gly Trp Glu Thr Asp Pro Asn Ala Tyr Ile Tyr Phe Thr Ile
            260                 265                 270

Gln Gly His Ala Trp Glu Pro Ile Cys Lys Ala Leu Gly Lys Pro Glu
            275                 280                 285

Trp Ile Ser Asp Pro Asn Tyr Ala Thr Ala Lys Ala Arg Gln Pro His
            290                 295                 300

Ile Phe Asp Ile Phe Asn Thr Ile Glu Glu Trp Leu Ala Asp Lys Thr
305                 310                 315                 320

Lys Tyr Glu Ala Val Asp Ile Leu Arg Lys Phe Asp Ile Pro Cys Ser
                325                 330                 335

Pro Val Leu Ser Met Lys Glu Ile Ala Ala Asp Pro Ser Leu Arg Ala
            340                 345                 350

Ser Gly Ser Ile Thr Glu Val Pro His Lys Glu Arg Gly Thr Tyr Leu
            355                 360                 365

Thr Val Gly Ser Pro Ile Lys Phe Ser Asp Leu Lys Pro Glu Ile Thr
            370                 375                 380

Gly Ser Pro Leu Leu Gly Glu His Ser Glu Glu Val Leu Ala Gly Leu
385                 390                 395                 400

Gly Tyr Gly Ala Asp Asp Ile Lys Arg Leu Arg Glu Ser Gln Val Ile
                405                 410                 415

<210> SEQ ID NO 54
<211> LENGTH: 1194
<212> TYPE: DNA
<213> ORGANISM: Artificial sequence
<220> FEATURE:
<223> OTHER INFORMATION: Synthetic

<400> SEQUENCE: 54
atgagtgcct ccaatcggca gggcccgctc gagcgttttc gtgtactcga cctcacccgc      60
ctgcgagcgg gcccgacggc ggtacggcag ctggcggact ggggagcgga tgtcatcaag     120
attgaaagcc gcaggcgct tgacgtcagc gacggctgga tcggggaccg cctcggctcg      180
gatttccaga acctgcatcg caacaagcgc agcatcacgc tcaacctcaa ggatccggaa     240
ggcgtgcgga tcctccagcg gctggtcgag gccgctgacg tgctggtgga gaatttccgg     300
ccaggcgtga agacccggct tggggtggac tatgaaacct tgcagcgcag caatcccggg     360
ctcgtctacg ccagcatctc gggcttcggg caggacggcc gtatgccga ccggccaggc     420 tacgaccaga ttgtgcaggg catgggcggg ctgatggcga tcaccggcga aaaggggcaa     480

```
ccgccgttgc ggaccgggat ctcgctggcg gataccggtg tcggcctgta cgcggcgctc    540
ggcatcatga cggccctgct cgagcgtgaa gtgtcgggcc gtgggcaatg ggtgcagacc    600
tccctgttgc agggcatgat cgcgctgacc gactaccagg cggcacgatg gctgatggac    660
ggcgaggtgc cggaaccggc aggcaacgat catcccactg cgacgccaac cggcgtgttc    720
ccgaccgccg atggccatat caacattgcc acggcaggcg aggagatgtg gcggcgcttg    780
tgcaatgcga tcggggcgcc ggagctgctc gggcgggtcg agtatgccag caacgaactg    840
cgcacaaaga accgggaggc gttgaaaggc gagcttgcgc aatacacgag gcgcaagaca    900
agttccgaat ggatccgggc cttcgagcag gcgagcgttg cctgtggccc catttaccgg    960
atggacgagg tattcgagga ccggcaaacg cagcatctgg gcatggccat atccctgcgg   1020
catccggagc ttcaggagat aaaggtcgtg gcgcagccgt acacgttgtc gcgcacgcca   1080
agccagatgc gcacggcaac gcccgggcga ggcgagcata ccgaagcggt gttgatggaa   1140
ctgggatata gcgcggaaca gatctcggac ctgcgcgagc gtcacgtggt gtga         1194
```

<210> SEQ ID NO 55
<211> LENGTH: 397
<212> TYPE: PRT
<213> ORGANISM: Artificial sequence
<220> FEATURE:
<223> OTHER INFORMATION: Synthetic

<400> SEQUENCE: 55

```
Met Ser Ala Ser Asn Arg Gln Gly Pro Leu Glu Arg Phe Arg Val Leu
1               5                   10                  15

Asp Leu Thr Arg Leu Arg Ala Gly Pro Thr Ala Val Arg Gln Leu Ala
                20                  25                  30

Asp Trp Gly Ala Asp Val Ile Lys Ile Glu Ser Pro Gln Ala Leu Asp
            35                  40                  45

Val Ser Asp Gly Trp Ile Gly Asp Arg Leu Gly Ser Asp Phe Gln Asn
        50                  55                  60

Leu His Arg Asn Lys Arg Ser Ile Thr Leu Asn Leu Lys Asp Pro Glu
65                  70                  75                  80

Gly Val Arg Ile Leu Gln Arg Leu Val Glu Ala Asp Val Leu Val
                85                  90                  95

Glu Asn Phe Arg Pro Gly Val Lys Thr Arg Leu Gly Val Asp Tyr Glu
            100                 105                 110

Thr Leu Gln Arg Ser Asn Pro Gly Leu Val Tyr Ala Ser Ile Ser Gly
        115                 120                 125

Phe Gly Gln Asp Gly Pro Tyr Ala Asp Arg Pro Gly Tyr Asp Gln Ile
    130                 135                 140

Val Gln Gly Met Gly Gly Leu Met Ala Ile Thr Gly Glu Lys Gly Gln
145                 150                 155                 160

Pro Pro Leu Arg Thr Gly Ile Ser Leu Ala Asp Thr Gly Val Gly Leu
                165                 170                 175

Tyr Ala Ala Leu Gly Ile Met Thr Ala Leu Leu Glu Arg Glu Val Ser
            180                 185                 190

Gly Arg Gly Gln Trp Val Gln Thr Ser Leu Leu Gln Gly Met Ile Ala
        195                 200                 205

Leu Thr Asp Tyr Gln Ala Ala Arg Trp Leu Met Asp Gly Glu Val Pro
    210                 215                 220

Glu Pro Ala Gly Asn Asp His Pro Thr Ala Thr Pro Thr Gly Val Phe
225                 230                 235                 240
```

```
Pro Thr Ala Asp Gly His Ile Asn Ile Ala Thr Ala Gly Glu Glu Met
                245                 250                 255

Trp Arg Arg Leu Cys Asn Ala Ile Gly Ala Pro Glu Leu Leu Gly Arg
            260                 265                 270

Val Glu Tyr Ala Ser Asn Glu Leu Arg Thr Lys Asn Arg Glu Ala Leu
        275                 280                 285

Lys Gly Glu Leu Ala Gln Tyr Thr Arg Arg Lys Thr Ser Ser Glu Trp
    290                 295                 300

Ile Arg Ala Phe Glu Gln Ala Ser Val Ala Cys Gly Pro Ile Tyr Arg
305                 310                 315                 320

Met Asp Glu Val Phe Glu Asp Arg Gln Thr Gln His Leu Gly Met Ala
                325                 330                 335

Ile Ser Leu Arg His Pro Glu Leu Gln Glu Ile Lys Val Val Ala Gln
            340                 345                 350

Pro Tyr Thr Leu Ser Arg Thr Pro Ser Gln Met Arg Thr Ala Thr Pro
        355                 360                 365

Gly Arg Gly Glu His Thr Glu Ala Val Leu Met Glu Leu Gly Tyr Ser
    370                 375                 380

Ala Glu Gln Ile Ser Asp Leu Arg Glu Arg His Val Val
385                 390                 395
```

<210> SEQ ID NO 56
<211> LENGTH: 1254
<212> TYPE: DNA
<213> ORGANISM: Artificial sequence
<220> FEATURE:
<223> OTHER INFORMATION: Synthetic

<400> SEQUENCE: 56

```
atgacaaccg aaaacgggga caaggcaccc ggcccgtgcg caggattgcg cgtgctggaa      60
ttcgcaacca tggttgccgg gccgttcgcc ggccagatgc tggccgatct cggggccgag     120
gtcatcaaga tcgagcccat cagtggcgat cccatgcgca agggcaccc ccagcaccag     180
ggggtcgcgg ctggattcgc gctgttcaac ggtggcaagc gaagcatgtg catcgacctc     240
aagtccccgt cggacaagc gctggcgcgc gagctggcgt tgactgccga tgtgctgatt     300
gagaacttcc gcccgggcgt gatggacgga ttcaggctcg gcatgagac cctttgccag     360
gccaatgcaa ggctcatcta tgcgtcaatc aatggcttcg cgtcgatgg accgtatgcc     420
gcacggcccg catacgatca tgtcgtgcag gcgctgagcg ggaccatgcc gggcatcggc     480
agccaggacc agcccgagcc cgtccgcaat tcggtcgtcg acaagattac cgctgccacc     540
gccgcacaag caattctggc cgcgctcgtc caccgcgagc gcaacggcgg caagggccag     600
cgggtctgcg tgtcgctgct ggacgcctac gccgccttca tgctgccgga tctgatggtg     660
aaccactact tccagacgcc aagtatcggt gcgcgcgccc tgcccaacac ctacttccca     720
atccggacgt cggacggcca cgtcatgggc catatcttca ccgacgagca gttcaggaat     780
ctctgccgga tgtttgaccg cctggacctg atcgacgatc ccgcttcgc tggtgtgaag     840
gagcgccgcg atcactgtga ggcgatgtgg gatgaaatcc ggcacagcgc gcggcggctc     900
gacacggcca ccgtcgagca gcttgccgag aagcacagcg tcccgcttgg gcgcgtcaac     960
gacctggccg ggttcttcgc cgatccgcag gtccggcaca acggcacgta ctcggacgat    1020
gacgatccat tgctcggaag agtgcgtcag cttcggtccc cgatccgcct ggcgctgacg    1080
ccagcggcca gccgccgccg gccgcccctg ctcggggagg acaccagcgc actcctcgcg    1140
```

```
ggcctgggca agacggcaac gcagatcaac caggcctttg caagccgggt ggtcgccggc   1200
cgcatggacg aggcggatgc cgcaggcaag tccgcggtgg agcacaagc atga          1254
```

<210> SEQ ID NO 57
<211> LENGTH: 417
<212> TYPE: PRT
<213> ORGANISM: Artificial sequence
<220> FEATURE:
<223> OTHER INFORMATION: Synthetic

<400> SEQUENCE: 57

```
Met Thr Thr Glu Asn Gly Asp Lys Ala Pro Gly Pro Cys Ala Gly Leu
1               5                   10                  15

Arg Val Leu Glu Phe Ala Thr Met Val Ala Gly Pro Phe Ala Gly Gln
            20                  25                  30

Met Leu Ala Asp Leu Gly Ala Glu Val Ile Lys Ile Glu Pro Ile Ser
        35                  40                  45

Gly Asp Pro Met Arg Lys Gly His Pro Gln His Gln Gly Val Ala Ala
    50                  55                  60

Gly Phe Ala Leu Phe Asn Gly Lys Arg Ser Met Cys Ile Asp Leu
65                  70                  75                  80

Lys Ser Pro Ser Gly Gln Ala Leu Ala Arg Glu Leu Ala Leu Thr Ala
                85                  90                  95

Asp Val Leu Ile Glu Asn Phe Arg Pro Gly Val Met Asp Gly Phe Arg
            100                 105                 110

Leu Gly His Glu Thr Leu Cys Gln Ala Asn Ala Arg Leu Ile Tyr Ala
        115                 120                 125

Ser Ile Asn Gly Phe Gly Val Asp Gly Pro Tyr Ala Ala Arg Pro Ala
    130                 135                 140

Tyr Asp His Val Val Gln Ala Leu Ser Gly Thr Met Pro Gly Ile Gly
145                 150                 155                 160

Ser Gln Asp Gln Pro Glu Pro Val Arg Asn Ser Val Val Asp Lys Ile
                165                 170                 175

Thr Ala Ala Thr Ala Ala Gln Ala Ile Leu Ala Ala Leu Val His Arg
            180                 185                 190

Glu Arg Asn Gly Gly Lys Gly Gln Arg Val Cys Val Ser Leu Leu Asp
        195                 200                 205

Ala Tyr Ala Ala Phe Met Leu Pro Asp Leu Met Val Asn His Tyr Phe
    210                 215                 220

Gln Thr Pro Ser Ile Gly Ala Arg Ala Leu Pro Asn Thr Tyr Phe Pro
225                 230                 235                 240

Ile Arg Thr Ser Asp Gly His Val Met Gly His Ile Phe Thr Asp Glu
                245                 250                 255

Gln Phe Arg Asn Leu Cys Arg Met Phe Asp Arg Leu Asp Leu Ile Asp
            260                 265                 270

Asp Pro Arg Phe Ala Gly Val Lys Glu Arg Arg Asp His Cys Glu Ala
        275                 280                 285

Met Trp Asp Glu Ile Arg His Ser Ala Arg Arg Leu Asp Thr Ala Thr
    290                 295                 300

Val Glu Gln Leu Ala Glu Lys His Ser Val Pro Leu Gly Arg Val Asn
305                 310                 315                 320

Asp Leu Ala Gly Phe Phe Ala Asp Pro Gln Val Arg His Asn Gly Thr
                325                 330                 335

Tyr Ser Asp Asp Asp Pro Leu Leu Gly Arg Val Arg Gln Leu Arg
            340                 345                 350
```

Ser Pro Ile Arg Leu Ala Leu Thr Pro Ala Ala Ser Arg Arg Pro
            355                 360                 365

Pro Leu Leu Gly Glu Asp Thr Ser Ala Leu Leu Ala Gly Leu Gly Lys
        370                 375                 380

Thr Ala Thr Gln Ile Asn Gln Ala Phe Ala Ser Arg Val Val Ala Gly
385                 390                 395                 400

Arg Met Asp Glu Ala Asp Ala Ala Gly Lys Ser Ala Val Gly Ala Gln
                405                 410                 415

Ala

<210> SEQ ID NO 58
<211> LENGTH: 1236
<212> TYPE: DNA
<213> ORGANISM: Artificial sequence
<220> FEATURE:
<223> OTHER INFORMATION: Synthetic

<400> SEQUENCE: 58
atgttgcgcg acgcactgga cggcctgacc gtcatcgatt tcacgcagat cggcgccggg      60
ccgacctgca ccatgctgct ggccgacatg ggcgcgaggg tcatcaaggt ggagccgccg     120
ggcggtgaga tgggccgcgg gctggggccc ggctggctcg gcgacgacag cgcgctgttt     180
cacggcttca accgcaacaa gctgggcgtg gcgctcgacc tgaagtccgc cgacggcgtg     240
gccgtggccc gccgcctgat cgtgggtgcc gacatcgtgg tggaaagcat gcggcccggc     300
gtgatggaac gcctcggcct tggccatgcg caactggcgg acgaacaccc cgcgctgatc     360
tactgctcga tctccgccta cgggcaggag ggaccatatg cgagccgcgc cggcgtcgac     420
ggcatcatgc aggcggattc cggcctgatg agcctgatcg gcctgcccga cggcgagccg     480
tgcaaggtgc aggcgccggt cgtcgacgtg atgaccggct acgtggcctc cgtgggcgtg     540
ttggcgaagc tcgcgcagcg ggcccgcgac ggcctgggcg ccatctcga cgtcaacctg      600 ctcaatgcgg cgctggcgct gcagcagtcg tccatcacca gctactgcgc cgacgggcaa     660
ctgccggaac gtgtgggcag cgcggcgccc tactcagcgc ccaaccaggc cttccgcacc     720
gccgatggct gggtcatggt ggccgcctat atgcccgagc gctggcgccg gttgtgcgat     780
gtgctgggcc ggcccgaact ggccggcgat ccgcgctttg cgacttcacc gctgcgcgtg     840
gtcaatcgcg cggcaatggt ggaggtgctg accagtgcct cgtcacccg cgcgaccgac      900 acatggctgg cgttgctcca ggacgccgac attctgtgcg cccccgtggc gacctacgag     960
gacgtcatgg cgcatccgca ggtggccgcc aaccgcatgg tgcagcgcgt ccggcacgac    1020
acgctgggcg agatccgcat gccgggattc ccgatcaaca gcgctcagga gaacgcgttg    1080
ccatcgcggc cggcaccagc ttgcggacag catacgcagg cggtgctggg cgagcttggc    1140
tacagccgcg acgaaatcgc cgcgctgtcg tctcggggcg ctatccgctg cggcgatatc    1200
gaggaaaagc gacacgtggt cgcggcggca tcgtga                              1236

<210> SEQ ID NO 59
<211> LENGTH: 411
<212> TYPE: PRT
<213> ORGANISM: Artificial sequence
<220> FEATURE:
<223> OTHER INFORMATION: Synthetic

<400> SEQUENCE: 59

Met Leu Arg Asp Ala Leu Asp Gly Leu Thr Val Ile Asp Phe Thr Gln
1               5                   10                  15

Ile Gly Ala Gly Pro Thr Cys Thr Met Leu Leu Ala Asp Met Gly Ala
            20                  25                  30

Arg Val Ile Lys Val Glu Pro Pro Gly Gly Glu Met Gly Arg Gly Leu
        35                  40                  45

Gly Pro Gly Trp Leu Gly Asp Asp Ser Ala Leu Phe His Gly Phe Asn
    50                  55                  60

Arg Asn Lys Leu Gly Val Ala Leu Asp Leu Lys Ser Ala Asp Gly Val
65                  70                  75                  80

Ala Val Ala Arg Arg Leu Ile Val Gly Ala Asp Ile Val Val Glu Ser
                85                  90                  95

Met Arg Pro Gly Val Met Glu Arg Leu Gly Leu Gly His Ala Gln Leu
            100                 105                 110

Ala Asp Glu His Pro Ala Leu Ile Tyr Cys Ser Ile Ser Ala Tyr Gly
        115                 120                 125

Gln Glu Gly Pro Tyr Ala Ser Arg Ala Gly Val Asp Gly Ile Met Gln
    130                 135                 140

Ala Asp Ser Gly Leu Met Ser Leu Ile Gly Leu Pro Asp Gly Glu Pro
145                 150                 155                 160

Cys Lys Val Gln Ala Pro Val Val Asp Val Met Thr Gly Tyr Val Ala
                165                 170                 175

Ser Val Gly Val Leu Ala Lys Leu Ala Gln Arg Ala Arg Asp Gly Leu
            180                 185                 190

Gly Gly His Leu Asp Val Asn Leu Leu Asn Ala Ala Leu Ala Leu Gln
        195                 200                 205

Gln Ser Ser Ile Thr Ser Tyr Cys Ala Asp Gly Gln Leu Pro Glu Arg
    210                 215                 220

Val Gly Ser Ala Ala Pro Tyr Ser Ala Pro Asn Gln Ala Phe Arg Thr
225                 230                 235                 240

Ala Asp Gly Trp Val Met Val Ala Ala Tyr Met Pro Glu Arg Trp Arg
                245                 250                 255

Arg Leu Cys Asp Val Leu Gly Arg Pro Glu Leu Ala Gly Asp Pro Arg
            260                 265                 270

Phe Ala Thr Ser Pro Leu Arg Val Val Asn Arg Ala Ala Met Val Glu
        275                 280                 285

Val Leu Thr Ser Ala Phe Val Thr Arg Ala Thr Asp Thr Trp Leu Ala
    290                 295                 300

Leu Leu Gln Asp Ala Asp Ile Leu Cys Ala Pro Val Ala Thr Tyr Glu
305                 310                 315                 320

Asp Val Met Ala His Pro Gln Val Ala Ala Asn Arg Met Val Gln Arg
                325                 330                 335

Val Arg His Asp Thr Leu Gly Glu Ile Arg Met Pro Gly Phe Pro Ile
            340                 345                 350

Asn Ser Ala Gln Glu Asn Ala Leu Pro Ser Arg Pro Ala Pro Ala Cys
        355                 360                 365

Gly Gln His Thr Gln Ala Val Leu Gly Glu Leu Gly Tyr Ser Arg Asp
    370                 375                 380

Glu Ile Ala Ala Leu Ser Ser Arg Gly Ala Ile Arg Cys Gly Asp Ile
385                 390                 395                 400

Glu Glu Lys Arg His Val Val Ala Ala Ser
                405                 410

<210> SEQ ID NO 60
<211> LENGTH: 822

<212> TYPE: DNA
<213> ORGANISM: Artificial sequence
<220> FEATURE:
<223> OTHER INFORMATION: Synthetic

<400> SEQUENCE: 60

```
atgccgatcg ccaatcctcg cagctacctg tttgtcccgg cctcgcgccc ggagcgcatc    60
gccaaggcga tcggctccgg cgccgatgcc gtcattgtcg atttcgagga tgcggtcgcg   120
cccgccgaca aggggcaggc ccgcgacggg cttggcgccc cgtgggcggc gctgggccag   180
caggcagcgg cagccggcgt cgccatgctg gtgcgcatca acggcgccga taccgcgtac   240
tacgaagacg atctcgcctg gtgccgcgca caggtgtctc ggaaatcgt gctgccgaag    300
gccgattcgg ccggcgtcga tgcgcttgct gcggcattgc ccgtgtgcg ctgtttcccg    360
ctggtcgaga cgccgccgg cttcgccggc ttacgcgagc tgcccgtgc cggcggcgtg    420
gtccggctgc tgttcggcag catcgacctg atgttcgatc tcgacgtgca ggacgacggt   480
gaggcgttgc actactttcg cagccggctg gtgcttcatt cccgcgcggc gggtttgccc   540
gcgcccgtgg atggcgtttg caccgcaatc ggcaatgacg ccgcacttgc cgcggaaacg   600
cgccgcgccc gggccttcgg ctttggcgcc aagctgctga tccacccggg ccaggtctgc   660
ggcgtgcacg acggcctggc gccgtcggcc gatgaacggc actgggccgg cgcgtcatg    720
gccgcggctg ccgctgccga tggcgccgcg gtggcggtgg acggcaagat ggtggaccgc   780
ccggtgctgg agcgcgcgcg ccggatcttg tccggtgggt ag                     822
```

<210> SEQ ID NO 61
<211> LENGTH: 273
<212> TYPE: PRT
<213> ORGANISM: Artificial sequence
<220> FEATURE:
<223> OTHER INFORMATION: Synthetic

<400> SEQUENCE: 61

```
Met Pro Ile Ala Asn Pro Arg Ser Tyr Leu Phe Val Pro Ala Ser Arg
1               5                   10                  15
Pro Glu Arg Ile Ala Lys Ala Ile Gly Ser Gly Ala Asp Ala Val Ile
            20                  25                  30
Val Asp Phe Glu Asp Ala Val Ala Pro Ala Asp Lys Gly Gln Ala Arg
        35                  40                  45
Asp Gly Leu Gly Ala Pro Trp Ala Ala Leu Gly Gln Gln Ala Ala Ala
    50                  55                  60
Ala Gly Val Ala Met Leu Val Arg Ile Asn Gly Ala Asp Thr Ala Tyr
65                  70                  75                  80
Tyr Glu Asp Asp Leu Ala Trp Cys Arg Ala Gln Gly Val Ser Glu Ile
                85                  90                  95
Val Leu Pro Lys Ala Asp Ser Ala Gly Val Asp Ala Leu Ala Ala Ala
            100                 105                 110
Leu Pro Gly Val Arg Cys Phe Pro Leu Val Glu Asn Ala Ala Gly Phe
        115                 120                 125
Ala Gly Leu Arg Glu Leu Ala Arg Ala Gly Val Val Arg Leu Leu
    130                 135                 140
Phe Gly Ser Ile Asp Leu Met Phe Asp Leu Asp Val Gln Asp Asp Gly
145                 150                 155                 160
Glu Ala Leu His Tyr Phe Arg Ser Arg Leu Val Leu His Ser Arg Ala
                165                 170                 175
Ala Gly Leu Pro Ala Pro Val Asp Gly Val Cys Thr Ala Ile Gly Asn
```

```
                180             185             190
Asp Ala Ala Leu Ala Ala Glu Thr Arg Arg Ala Arg Ala Phe Gly Phe
            195                 200                 205
Gly Ala Lys Leu Leu Ile His Pro Gly Gln Val Cys Gly Val His Asp
            210                 215                 220
Gly Leu Ala Pro Ser Ala Asp Glu Arg His Trp Ala Gly Arg Val Met
225                 230                 235                 240
Ala Ala Ala Ala Ala Asp Gly Ala Ala Val Ala Val Asp Gly Lys
                245                 250                 255
Met Val Asp Arg Pro Val Leu Glu Arg Ala Arg Arg Ile Leu Ser Gly
            260                 265                 270
Gly

<210> SEQ ID NO 62
<211> LENGTH: 1173
<212> TYPE: DNA
<213> ORGANISM: Artificial sequence
<220> FEATURE:
<223> OTHER INFORMATION: Synthetic

<400> SEQUENCE: 62
atgccccatc ccctcgaagg catcaccgtc gtttccctgg agcaggcgat cgcggccccg      60
ttctgcaccc gccagctggc ggacctgggc gcgcgcatca tcaagatcga gcggcctggc     120
agcggcgact tgcccgcgc ctacgacacg cgcgtgcgcg gcttgtcttc gcacttcgtc     180
tggaccaacc gctccaagga gagcctcacg ctcgacgtca gcacgccgc ggccgccccc     240
gtgctggccg gactgctcga acgcgcggac gtgctggtgc agaacctcgc gcccggcgcg     300
gccgcgcgcc tgggcctgga cttcgacagc ctgagcgaaa agtacccgcg cctgatcgtg     360
tgcgatatct cgggctatgg cagcgacggc ccgtaccgcg acaagaaggc ctacgacctg     420
ctggtccaga gcgagtccgg cttttgtctcc gtgaccggca gccggacga cggcgtcaag     480
gcaggtgcct cagtagccga tattgcgcc ggcatgtacg cctataccaa tatcctggcc     540
gcgctgctgg aacgcggcaa gaccgggcgc ggcaagcgca tcgatatctc gatgctggaa     600
tcgatggtgg agtggatggg cttcccgctc tactacgcct tcgatggcgc cgagccgccg     660
ccgcgcgcgg gcgcggcaca tgccaccatc tatccctatg cccgtttcc gaccggcgat     720
ggcaagaccg tgatgcttgg actgcagaac gagcgcgagt gggtcgtgtt ctgcgaggcg     780
gtgctgggcg aacccgatct cgccacgcat cccgactttg ccagcaacag cctgcgcaac     840
cagaaccgcg ccgcgctgcg cgcgcgcatc gtcgacagct tctcgggcct gaccgccacc     900
gaagtggccg accggctgga ggccgccagg attgccaatg cgcgggtcaa taccatcgct     960
gacgtttggg accaccccca gctggcggcg cgccagcgct ggcgccaggt cgacacgccg    1020
gtgggtccgg tgccggcgtt gctgccgccg ggcatgaccg aggcacgcat ggacccgatt    1080
ccgtcgctcg gcgcgagcac cgatgccatc ctggccgaac tgggccagac cgcggcgcag    1140
attgccgcgt tgcgctcggc cggcgcagtc tga                                 1173

<210> SEQ ID NO 63
<211> LENGTH: 390
<212> TYPE: PRT
<213> ORGANISM: Artificial sequence
<220> FEATURE:
<223> OTHER INFORMATION: Synthetic

<400> SEQUENCE: 63
```

Met Pro His Pro Leu Glu Gly Ile Thr Val Ser Leu Glu Gln Ala
1               5                   10                  15

Ile Ala Ala Pro Phe Cys Thr Arg Gln Leu Ala Asp Leu Gly Ala Arg
            20                  25                  30

Ile Ile Lys Ile Glu Arg Pro Gly Ser Gly Asp Phe Ala Arg Ala Tyr
        35                  40                  45

Asp Thr Arg Val Arg Gly Leu Ser Ser His Phe Val Trp Thr Asn Arg
    50                  55                  60

Ser Lys Glu Ser Leu Thr Leu Asp Val Lys His Ala Ala Ala Ala Pro
65                  70                  75                  80

Val Leu Ala Gly Leu Leu Glu Arg Ala Asp Val Leu Val Gln Asn Leu
                85                  90                  95

Ala Pro Gly Ala Ala Ala Arg Leu Gly Leu Asp Phe Asp Ser Leu Ser
            100                 105                 110

Glu Lys Tyr Pro Arg Leu Ile Val Cys Asp Ile Ser Gly Tyr Gly Ser
        115                 120                 125

Asp Gly Pro Tyr Arg Asp Lys Lys Ala Tyr Asp Leu Leu Val Gln Ser
    130                 135                 140

Glu Ser Gly Phe Val Ser Val Thr Gly Thr Pro Asp Asp Gly Val Lys
145                 150                 155                 160

Ala Gly Ala Ser Val Ala Asp Ile Ala Ala Gly Met Tyr Ala Tyr Thr
                165                 170                 175

Asn Ile Leu Ala Ala Leu Leu Glu Arg Gly Lys Thr Gly Arg Gly Lys
            180                 185                 190

Arg Ile Asp Ile Ser Met Leu Glu Ser Met Val Glu Trp Met Gly Phe
        195                 200                 205

Pro Leu Tyr Tyr Ala Phe Asp Gly Ala Glu Pro Pro Arg Ala Gly
    210                 215                 220

Ala Ala His Ala Thr Ile Tyr Pro Tyr Gly Pro Phe Pro Thr Gly Asp
225                 230                 235                 240

Gly Lys Thr Val Met Leu Gly Leu Gln Asn Glu Arg Glu Trp Val Val
                245                 250                 255

Phe Cys Glu Ala Val Leu Gly Glu Pro Asp Leu Ala Thr His Pro Asp
            260                 265                 270

Phe Ala Ser Asn Ser Leu Arg Asn Gln Asn Arg Ala Ala Leu Arg Ala
        275                 280                 285

Arg Ile Val Asp Ser Phe Ser Gly Leu Thr Ala Thr Glu Val Ala Asp
    290                 295                 300

Arg Leu Glu Ala Ala Arg Ile Ala Asn Ala Arg Val Asn Thr Ile Ala
305                 310                 315                 320

Asp Val Trp Asp His Pro Gln Leu Ala Ala Arg Gln Arg Trp Arg Gln
                325                 330                 335

Val Asp Thr Pro Val Gly Pro Val Pro Ala Leu Leu Pro Pro Gly Met
            340                 345                 350

Thr Glu Ala Arg Met Asp Pro Ile Pro Ser Leu Gly Ala Ser Thr Asp
        355                 360                 365

Ala Ile Leu Ala Glu Leu Gly Gln Thr Ala Ala Gln Ile Ala Ala Leu
    370                 375                 380

Arg Ser Ala Gly Ala Val
385                 390

<210> SEQ ID NO 64
<211> LENGTH: 1200
<212> TYPE: DNA

<213> ORGANISM: Artificial sequence
<220> FEATURE:
<223> OTHER INFORMATION: Synthetic

<400> SEQUENCE: 64

```
atgaaaaagc cactgcgcca tatccgcgtg ctcgacctga ccaatgtgct ggccgggccg      60
ttctgctgcc accagcttgc ccacctgggc gccgaagtca tcaaggtgga accccccggc     120
accggcgacc tggcccggca gctgggcgcc gatgccgagc tgaaccagcg cctgatgggc     180
gtgtcgttcc tggcccagaa cccaggcaag cagtcggtca cgctcaacct gaagcacgcg     240
cgcggcaagg aggtgttccg caagctggtg caaagcgccg acgtgctggt ggagaacttc     300
cgccccggcg tgatggaccg gctcgggctg ggctacgaga ccctgaagca ggacaacccg     360
cgcctgatct actgcgcgat ctcgggcttt ggccaggacg gccgctggc cgggctgccg      420
gcctatgacc agatcatcca gggcatggcc ggcgtgatga gcattaccgg cgatgcgcag     480
agcgcaccgt tgcgggtcgg ctatccggtc tcggacacca tcggcgggct gaccgcggcg     540
ctggcggtat cggcggcgct ggcggaccac cagcgcaccg aaggctattt cgtcgacgta     600
tcgatgctgg aagccacgct ggccaccatg gctgggtgg tatccaacca cctgatcgcc      660
ggcaaggtgc cggcgccgat gggcaacgag aacatgaccg ccagcccttc cggcactttc     720
cgcaccgcgg acgggctgct caatatcgcc gccaacaagc aggaacagtt tgaagccgtg     780
tgccgcgtgc tgggccgccc cgagctggcc gcgatccgc gcttcgcgca cgccaggcg      840
cggctggcca accggggcga actgacacag gcgctggaag cagagctggc gaagaagccg     900
gccaccgaat ggtggccgct gctgaccgag ccggcgtgc ccgccggccc ggtgctggac     960
gtgccacaga cgctggcgca tccgcaggtg cgcgagcgcg gcatgatcgg cgaatttgcc    1020
gatgcgcccg gcgtgggccg cgatatccgc gtggtgcgca ccggcttcaa gctcaaccgc    1080
gaggccccgg ccgtggacac gccgccgccg gagctgggcc agcatacgcg gcaggtgctg    1140
gccagcctgg gctacagcga tgcggacatc gaccaactga gcgaggagcg cgcgatatga    1200
```

<210> SEQ ID NO 65
<211> LENGTH: 399
<212> TYPE: PRT
<213> ORGANISM: Artificial sequence
<220> FEATURE:
<223> OTHER INFORMATION: Synthetic

<400> SEQUENCE: 65

```
Met Lys Lys Pro Leu Arg His Ile Arg Val Leu Asp Leu Thr Asn Val
1               5                   10                  15

Leu Ala Gly Pro Phe Cys Cys His Gln Leu Ala His Leu Gly Ala Glu
                20                  25                  30

Val Ile Lys Val Glu Thr Pro Gly Thr Gly Asp Leu Ala Arg Gln Leu
            35                  40                  45

Gly Ala Asp Ala Glu Leu Asn Gln Arg Leu Met Gly Val Ser Phe Leu
        50                  55                  60

Ala Gln Asn Pro Gly Lys Gln Ser Val Thr Leu Asn Leu Lys His Ala
65                  70                  75                  80

Arg Gly Lys Glu Val Phe Arg Lys Leu Val Gln Ser Ala Asp Val Leu
                85                  90                  95

Val Glu Asn Phe Arg Pro Gly Val Met Asp Arg Leu Gly Leu Gly Tyr
            100                 105                 110

Glu Thr Leu Lys Gln Asp Asn Pro Arg Leu Ile Tyr Cys Ala Ile Ser
        115                 120                 125
```

Gly Phe Gly Gln Asp Gly Pro Leu Ala Gly Leu Pro Ala Tyr Asp Gln
            130                 135                 140

Ile Ile Gln Gly Met Ala Gly Val Met Ser Ile Thr Gly Asp Ala Gln
145                 150                 155                 160

Ser Ala Pro Leu Arg Val Gly Tyr Pro Val Ser Asp Thr Ile Gly Gly
                165                 170                 175

Leu Thr Ala Ala Leu Ala Val Ser Ala Ala Leu Ala Asp His Gln Arg
            180                 185                 190

Thr Glu Gly Tyr Phe Val Asp Val Ser Met Leu Glu Ala Thr Leu Ala
        195                 200                 205

Thr Met Gly Trp Val Val Ser Asn His Leu Ile Ala Gly Lys Val Pro
    210                 215                 220

Ala Pro Met Gly Asn Glu Asn Met Thr Ala Ser Pro Ser Gly Thr Phe
225                 230                 235                 240

Arg Thr Ala Asp Gly Leu Leu Asn Ile Ala Ala Asn Lys Gln Glu Gln
                245                 250                 255

Phe Glu Ala Val Cys Arg Val Leu Gly Arg Pro Glu Leu Ala Ala Asp
            260                 265                 270

Pro Arg Phe Ala Gln Arg Gln Ala Arg Leu Ala Asn Arg Gly Glu Leu
        275                 280                 285

Thr Gln Ala Leu Glu Ala Glu Leu Ala Lys Lys Pro Ala Thr Glu Trp
    290                 295                 300

Trp Pro Leu Leu Thr Glu Ala Gly Val Pro Ala Gly Pro Val Leu Asp
305                 310                 315                 320

Val Pro Gln Thr Leu Ala His Pro Gln Val Arg Glu Arg Gly Met Ile
                325                 330                 335

Gly Glu Phe Ala Asp Ala Pro Gly Val Gly Arg Asp Ile Arg Val Val
            340                 345                 350

Arg Thr Gly Phe Lys Leu Asn Arg Glu Ala Pro Ala Val Asp Thr Pro
        355                 360                 365

Pro Pro Glu Leu Gly Gln His Thr Arg Gln Val Leu Ala Ser Leu Gly
    370                 375                 380

Tyr Ser Asp Ala Asp Ile Asp Gln Leu Ser Glu Glu Arg Ala Ile
385                 390                 395

METHODS AND MATERIALS FOR THE BIOSYNTHESIS OF COMPOUNDS INVOLVED IN THE TRICARBOXYLIC ACID CYCLE AND DERIVATIVES AND COMPOUNDS RELATED THERETO

This patent application claims the benefit of priority from U.S. Provisional Application Ser. No. 62/694,602, filed Jul. 6, 2018 and U.S. Provisional Application Ser. No. 62/624,874, filed Feb. 1, 2018, the contents of each of which is herein incorporated by reference in its entirety.

FIELD

The present invention relates to biosynthetic methods and materials for the production of compounds involved in the tricarboxylic acid cycle (TCA cycle), and/or derivatives thereof and/or compounds related thereto. The present invention also relates to products biosynthesized or otherwise encompassed by these methods and materials.

Replacement of traditional chemical production processes relying on, for example fossil fuels and/or potentially toxic chemicals, with environmentally friendly (e.g., green chemicals) and/or "cleantech" solutions is being considered, including work to identify building blocks suitable for use in the manufacturing of such chemicals. See, "Conservative evolution and industrial metabolism in Green Chemistry", Green Chem., 2018, 20, 2171-2191.

The TCA (tricarboxylic acid) cycle, also known as Krebs cycle or citric acid cycle, is a key metabolic pathway of central metabolism in aerobes and is a major biochemical hub of various organisms. The TCA cycle comprises nine biochemical reactions carried out by eight enzymes to generate energy from acetyl-CoA (See FIG. 1). The TCA cycle also contributes to the synthesis of metabolic precursors for anabolism. Metabolic engineering of the TCA cycle of micro-organisms has been reported to be suitable for the production of industrially relevant chemicals, such as succinic acid (Lee et al. Appl Environ Microbiol. 2005 71(12): 7880-7), fumaric acid (Xu et al. Bioresour Technol. 2013 148:91-6), lysine (Becker et al. Appl Environ Microbiol. 2009 75(24):7866-9) and 1,4-butanediol (Yim et al. Nat Chem Biol. 2011. 7(7):445-52).

Itaconic acid is also a chemical that derives from the TCA cycle. This compound is used industrially for the manufacturing of synthetic polymers, such as plastics, resins and latex. Itaconic acid production was discovered based on experiments conducted in *A. itaconicus* (Kinoshita ActaPhytochim. 1932 5:271-287) but this molecule is currently produced industrially using *Aspergillus terreus, A. terreus*. In *A. terreus*, the gene cad1 encoding a cis-aconitate decarboxylase was identified (Kanamasa et al. Appl Microbiol Biotechnol. 2008 80(2):223-9). This enzyme converts cis-aconitate from the TCA cycle into itaconic acid (see FIG. 1). Heterologous expression of this gene has also enabled itaconic acid production in micro-organisms including *S. cerevisiae* (Blazeck et al. Appl Microbiol Biotechnol. 2014. 98(19):8155-64), *Y. lipolytica* (Blazeck et al. Metab Eng. 2015. 32:66-73), *C. glutamicum* (Otten et al. Metab Eng. 2015. 30:156-65) or *E. coli* (Okamoto et al. J Gen Appl Microbiol. 2014. 60(5):191-7, Vuoristo et al. Appl Microbiol Biotechnol. 2015. 99(1):221-8, Harder et al. Metab Eng. 2016. 38:29-37).

Expression of cad1 in *E. coli* reportedly resulted in detectable, but low amounts of itaconic acid (Li et al. Fungal Genet Biol. 2011. 48(6):602-11).

Additional studies have reported that itaconic production can be further improved by metabolic engineering. For example, studies have shown that the titers can be increased by interrupting the metabolic flux of the TCA cycle downstream of the itaconic acid precursor, cis-aconitate, either by deleting icd1, encoding the isocitrate dehydrogenase (Okamoto et al. J Gen Appl Microbiol. 2014 60(5):191-7) or by downregulating the Icd activity and deleting both sucCD, encoding the succinyl-CoA synthase, and aceA, encoding the isocitrate lyase involved in the glyoxylate cycle (Harder et al. Metab Eng. 2016 38:29-37) (FIG. 1). In addition to these genetic modifications, the overexpression of the acn gene, encoding an aconitate hydratase, from *E. coli* (acnB) or from *Corynebacterium glutamicum, C. glutamicum*, (acnA) has also reportedly resulted in improved production (Okamoto et al. J Gen Appl Microbiol. 2014 60(5):191-7; Vuoristo et al. Appl Microbiol Biotechnol. 2015. 99(1):221-8) (FIG. 1). The introduction of *C. glutamicum* citrate synthase GltA also increased the itaconic acid titers (Vuoristo et al. Appl Microbiol Biotechnol. 2015 99(1):221-8; Harder et al. Metab Eng. 2016 38:29-37) (FIG. 1).

Artificially increasing carbon flux via the TCA cycle has also been reported as an approach to obtain greater itaconic acid production. Inactivation of the pyruvate kinase activity (by deleting pyk) has allowed an increase in the anaplerotic flux to oxaloacetic acid (FIG. 1) (Harder et al. Metab Eng. 2016 38:29-37). It has also been reported that itaconic acid levels are higher when the carbon flux from *E. coli* central metabolism is redirected towards acetyl-CoA production, a precursor of itaconic acid. This was achieved by deleting pta, encoding the phosphate acetyltransferase or ldhA, encoding the lactate dehydrogenase (FIG. 1) (Vuoristo et al. Appl Microbiol Biotechnol. 2015. 99(1):221-8; Harder et al. Metab Eng. 2016 38:29-37).

Nevertheless, challenges have been reported in producing itaconic acid in *E. coli*. For example, according to some reports, no production of itaconic acid was detected during growth at 37° C. due to the formation of insoluble aggregates of CadA (the protein expressed from the *A. terreus* gene cad1 is known as CadA) resulting in its loss of functionality (Yamamoto et al. Bioengineered. 2015 6(5): 303-6). This problem was reportedly circumvented, at least in part, by either producing itaconic acid at 20° C. or 28° C. with poorer growth of *E. coli* cells or using a two-step process, in which biomass was first generated at 37° C. and followed by itaconic acid production at 28° C. (Harder et al. Biotechnol Bioeng. 2018. 115(1):156-164.).

Additionally, cad1 seems to be a bottleneck when expressed heterologously. *E. coli* strains containing only cad1 reportedly produced relatively low amounts (80 ppm itaconic acid overnight) (Li et al. Fungal Genet Biol. 2011 48(6):602-11). Also, expressing cad1 from vectors containing inducible promoters such as $P_{LAC}$ or $P_{BAD}$ did not yield sufficient levels of cad1, suggesting that a strong promoter is required (Yamamoto et al. Bioengineered. 2015 6(5):303-6). Attempts to address these limitations continue, and have included overexpressing multi copies of cad1 (Kim et al. Sci Rep. 2017 7:39768) and expressing cad1 from a stronger and/or constitutive vector (Yamamoto et al. Bioengineered. 2015. 6(5):303-6; Harder et al. Metab Eng. 2016 38:29-37).

Interrupting the isocitrate dehydrogenase activity by deleting icd reportedly resulted in a growth defect, or an auxotrophy towards glutamate in *E. coli* (Okamoto et al. J Gen Appl Microbiol 2014. 60(5):191-7, Yamamoto et al. Bioengineered. 2015 6(5):303-6).

Itaconic acid degradation by mammalian mitochondria as well as some bacteria, such as *Salmonella* spp. and

*Pseudomonas* spp. was described in the 1960s (Brightman et al. Journal of Bacteriology 1961 82(3):376-382; Martin et al. Journal of Bacteriology 1961 82(6):905-908; and Cooper R A & Kornberg H L Biochemical Journal. 1964 91(1):82-91). Further, a complete itaconate degradation pathway was validated when the genes encoding the three enzymes in the process were identified in *Y. pestis* and *P. aeruginosa* (Sasikaran et al. Nature Chemical Biology 2014 10: 371-377). These genes have also been identified in *A. terreus*, a species used for industrial production of itaconic acid (Chen et al. Appl Microbiol Biotechnol 2016 100:7541).

Biosynthetic materials and methods, including organisms having increased production of compounds involved in the TCA cycle, derivatives thereof and compounds related thereto are needed.

SUMMARY OF THE INVENTION

An aspect of the present invention relates to a process for biosynthesis of compounds involved in the TCA cycle, and/or derivatives thereof and/or compounds related thereto. One process of the present invention comprises obtaining an organism capable of producing compounds involved in the TCA cycle and derivatives and compounds related thereto, altering the organism, and producing more compounds involved in the TCA cycle and derivatives and compounds related thereto in the altered organism as compared to the unaltered organism. In one nonlimiting embodiment, the organism is *Cupriavidus necator, C. necator*, or an organism with one or more properties similar thereto. In one nonlimiting embodiment, the organism is altered to express a cis-aconitate decarboxylase, a citrate synthase and/or an aconitate hydratase, or a polypeptide or oligopeptide having the activities of a cis-aconitate decarboxylase, a citrate synthase and/or an aconitate hydratase.

In one nonlimiting embodiment, the organism is altered to express a cis-aconitate decarboxylase. In one nonlimiting embodiment, the cis-aconitate decarboxylase comprises *A. terreus* CadA (SEQ ID NO:1) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 1 or a functional fragment thereof. In one nonlimiting embodiment, the cis-aconitate decarboxylase is encoded by a nucleic acid sequence comprising *A. terreus* cad1 (SEQ ID NO:2) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 2 or a functional fragment thereof. In one nonlimiting embodiment, the cis-aconitate decarboxylase is cad1 classified in EC 4.1.1.6.

In one nonlimiting embodiment, the organism is altered to express a citrate synthase. In one nonlimiting embodiment, the citrate synthase comprises *C. glutamicum* or *C. necator* gltA (SEQ ID NO:3 or 5) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 3 or 5 or a functional fragment thereof. In one nonlimiting embodiment, the citrate synthase is encoded by a nucleic acid sequence comprising *C. glutamicum* or *C. necator* gltA (SEQ ID NO:4, 6 or 7) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 4, 6 or 7 or a functional fragment thereof. In one nonlimiting embodiment, the citrate synthase is gltA classified in EC 2.3.3.16.

In one nonlimiting embodiment, the organism is altered to express an aconitate hydratase. In one nonlimiting embodiment, the aconitate hydratase comprises *C. necator* AcnA or AcnB (SEQ ID NO:8 or 10) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 8 or 10 or a functional fragment thereof. In one nonlimiting embodiment, the aconitate hydratase is encoded by a nucleic acid sequence comprising *C. necator* acnA or acnB (SEQ ID NO:9 or 11) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO:9 or 11 or a functional fragment thereof. In one nonlimiting embodiment, the aconitate hydratase is AcnA or AcnB classified in EC 4.2.1.3.

In one nonlimiting embodiment, the nucleic acid sequence is codon optimized for *C. necator*.

In one nonlimiting embodiment, the organism is altered to express two or more of the enzymes of cis-aconitate decarboxylase, citrate synthase and/or aconitate hydratase as disclosed herein.

In one nonlimiting embodiment, the organism is altered to express a cis-aconitate decarboxylase, a citrate synthase and an aconitate hydratase as disclosed herein.

In one nonlimiting embodiment, the organism is further altered to inactivate the metabolic flow downstream of cis-aconitate. In one nonlimiting embodiment, isocitrate dehydrogenase activity is inactivated. In one nonlimiting embodiment, the genes icd1 and/or icd2 are eliminated.

In one nonlimiting embodiment, the organism is modulated to decrease degradation of itaconic acid. In one nonlimiting embodiment, Ict classified in EC:2.8.3-, Ich classified in EC: 4.2.1-, Ccl classified in EC:4.1.3- and/or Suc classified in EC:6.2.1- is downregulated, deleted or mutated. In one nonlimiting embodiment, a gene identified in Table 5 is downregulated, deleted or mutated.

In one nonlimiting embodiment, the organism is further modified to eliminate phaCAB, involved in PHBs production and/or H16-A0006-9 encoding endonucleases thereby improving transformation efficiency.

Another aspect of the present invention relates to an organism altered to produce more compounds involved in the TCA cycle and/or derivatives and compounds related thereto as compared to the unaltered organism. In one nonlimiting embodiment, the organism is *C. necator* or an organism with properties similar thereto. In one nonlimiting embodiment, the organism is altered to express the gene encoding a cis-aconitate decarboxylase, a citrate synthase and/or an aconitate hydratase as disclosed herein.

In one nonlimiting embodiment, the organism is altered with a nucleic acid sequence codon optimized for *C. necator*.

In one nonlimiting embodiment, the organism is further altered to inactivate the metabolic flow downstream of cis-aconitate. In one nonlimiting embodiment, isocitrate dehydrogenase activity is inactivated. In one nonlimiting embodiment, the genes icd1 and/or icd2 are eliminated.

In one nonlimiting embodiment, the organism is modulated to decrease degradation of itaconic acid. In one nonlimiting embodiment, Ict classified in EC:2.8.3-, Ich classified in EC: 4.2.1-, Ccl classified in EC:4.1.3- and/or Suc classified in EC:6.2.1.- is downregulated, deleted or mutated. In one nonlimiting embodiment, a gene identified in Table 5 is downregulated, deleted or mutated.

In one nonlimiting embodiment, the organism is further modified to eliminate phaCAB, involved in PHBs production and/or H16-A0006-9 encoding endonucleases thereby improving transformation efficiency.

In one nonlimiting embodiment, the organism is altered to express, overexpress, not express or express less of one or more molecules depicted in FIG. 1. In one nonlimiting embodiment, the molecule(s) comprise a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence corresponding to a molecule(s) depicted in FIG. 1, or a functional fragment thereof.

Another aspect of the present invention relates to bio-derived, bio-based, or fermentation-derived products produced from any of the methods and/or altered organisms disclosed herein. Such products include compositions comprising at least one bio-derived, bio-based, or fermentation-derived compound or any combination thereof, as well as bio-derived, bio-based, or fermentation-derived plastics, resins and rubber like resins, latex, detergents, paper, thickeners, shampoos, industrial cleaners and carpet backing comprising these bio-derived, bio-based, or fermentation-derived compositions or compounds; molded substances obtained by molding the bio-derived, bio-based, or fermentation-derived compositions or compound or plastics, resins and rubber like resins, latex, detergents, paper, thickeners, shampoos, industrial cleaners and carpet backing; bio-derived, bio-based, or fermentation-derived formulations comprising the bio-derived, bio-based, or fermentation-derived compositions or compounds, polymers plastics, resins and rubber like resins, latex, detergents, paper, thickeners, shampoos, industrial cleaners and carpet backings, or the bio-derived, bio-based, or fermentation-derived molded substances, or any combination thereof; and bio-derived, bio-based, or fermentation-derived semi-solids or non-semi-solid streams comprising the bio-derived, bio-based, or fermentation-derived compositions or compounds, plastics, resins and rubber like resins, latex, detergents, paper, thickeners, shampoos, industrial cleaners and carpet backing, molded substances or formulations, or any combination thereof.

Another aspect of the present invention relates to a bio-derived, bio-based or fermentation derived product biosynthesized in accordance with the exemplary central metabolism depicted in FIG. 1.

Another aspect of the present invention relates to exogenous genetic molecules of the altered organisms disclosed herein. In one nonlimiting embodiment, the exogenous genetic molecule comprises a codon optimized nucleic acid sequence encoding a cis-aconitate decarboxylase, a citrate synthase and/or an aconitate hydratase or a fragment thereof. In one nonlimiting embodiment, the nucleic acid sequence is codon optimized for *C. necator*. In one nonlimiting embodiment, the exogenous genetic molecule comprises a nucleic acid sequence encoding a cis-aconitate decarboxylase. In one nonlimiting embodiment, the nucleic acid sequence comprises SEQ ID NO:2 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 2 or a functional fragment thereof. In one nonlimiting embodiment, the exogenous genetic molecule comprises a nucleic acid sequence encoding a citrate synthase. In one nonlimiting embodiment the nucleic acid sequence comprises SEQ ID NO: 4, 6 or 7 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 4, 6 or 7 or a functional fragment thereof. In one nonlimiting embodiment, the exogenous genetic molecule comprises a nucleic acid sequence encoding an aconitate hydratase. In one nonlimiting embodiment, the exogenous genetic molecule comprises SEQ ID NO: SEQ ID NO:9 or 11 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 9 or 11 or a functional fragment thereof. Additional nonlimiting examples of exogenous genetic molecules include expression constructs of, for example, a cis-aconitate decarboxylase, a citrate synthase and/or an aconitate hydratase and synthetic operons of, for example, a cis-aconitate decarboxylase, a citrate synthase and/or an aconitate hydratase.

Yet another aspect of the present invention relates to means and processes for use of these means for biosynthesis of compounds involved in the TCA cycle, derivatives thereof and/or compounds related thereto.

DETAILED DESCRIPTION

Figure 1:
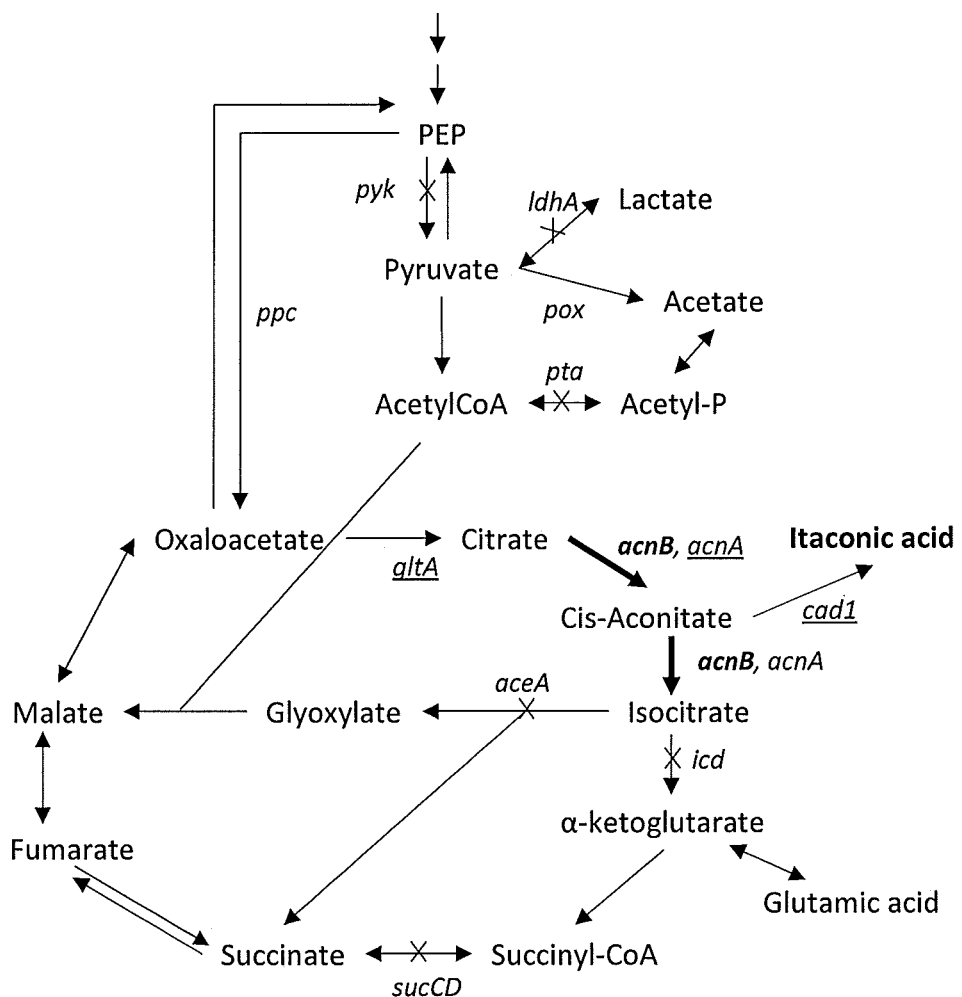
FIG. 1 is an exemplary schematic of the itaconic acid biosynthesis pathway and the metabolic engineering strategies developed for higher production in *E. coli*. The genes adjacent to crosses indicate gene deletions. The dotted arrow represents a down regulation of the gene. The underlined names represent a heterologous expression of the genes (*C. glutamicum* for gltA and acnA, *A. terreus* for cad1). Arrows and names in bold indicate overexpression of a *C. necator* gene.
Figure 2:
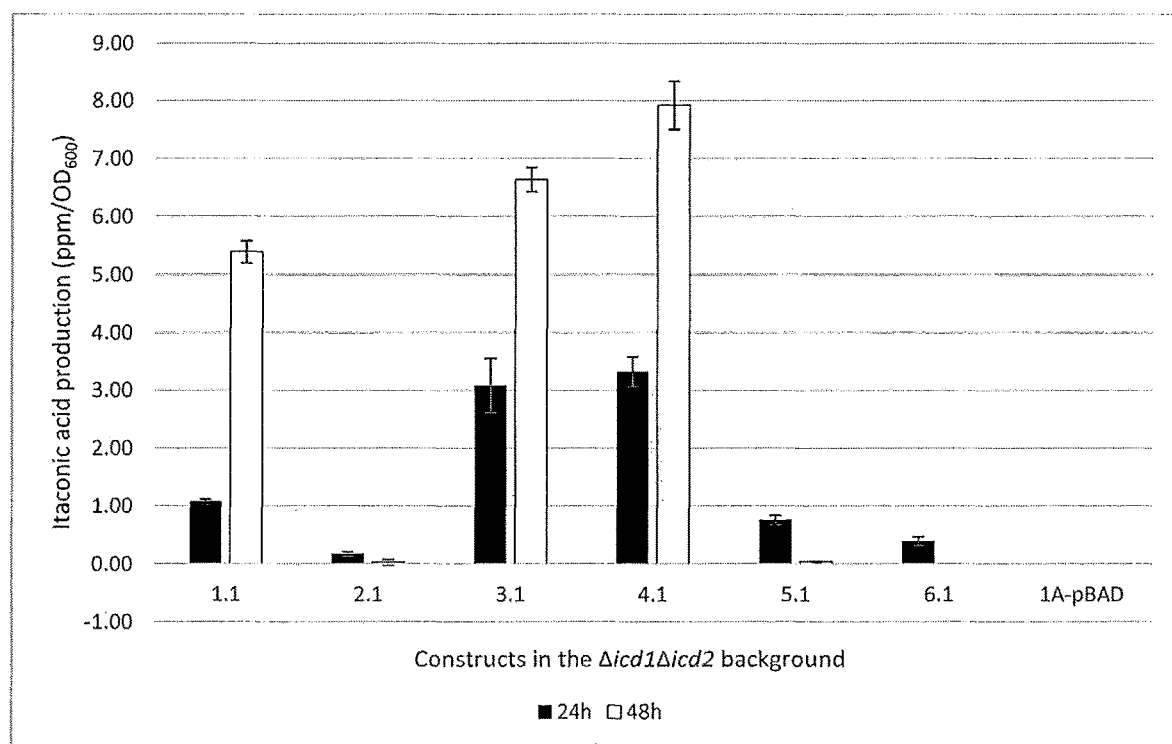
FIG. 2 shows itaconic acid production for various constructs in the *C. necator* mutant ΔphaCAB ΔA0006-9 Δicd1 Δicd2 background (double mutant) in assay 2. The results are indicated in ppm/$OD_{600}$. The error bars are representative of standard deviations of replicates. 1.1: At cad1; 2.1: At cad1, Cn acnA, Cn acnB; 3.1: At cad1, Cg gltA; 4.1: At cad1, Cn gltA; 5.4: At cad1, Cg gltA, Cn acnA, Cn acnB; 6.1: At cad1, Cn gltA, Cn acnA, Cn acnB (At=*A. terreus*; Cn=*C. necator* and Cg=*C. glutamicum*).
Figure 3:
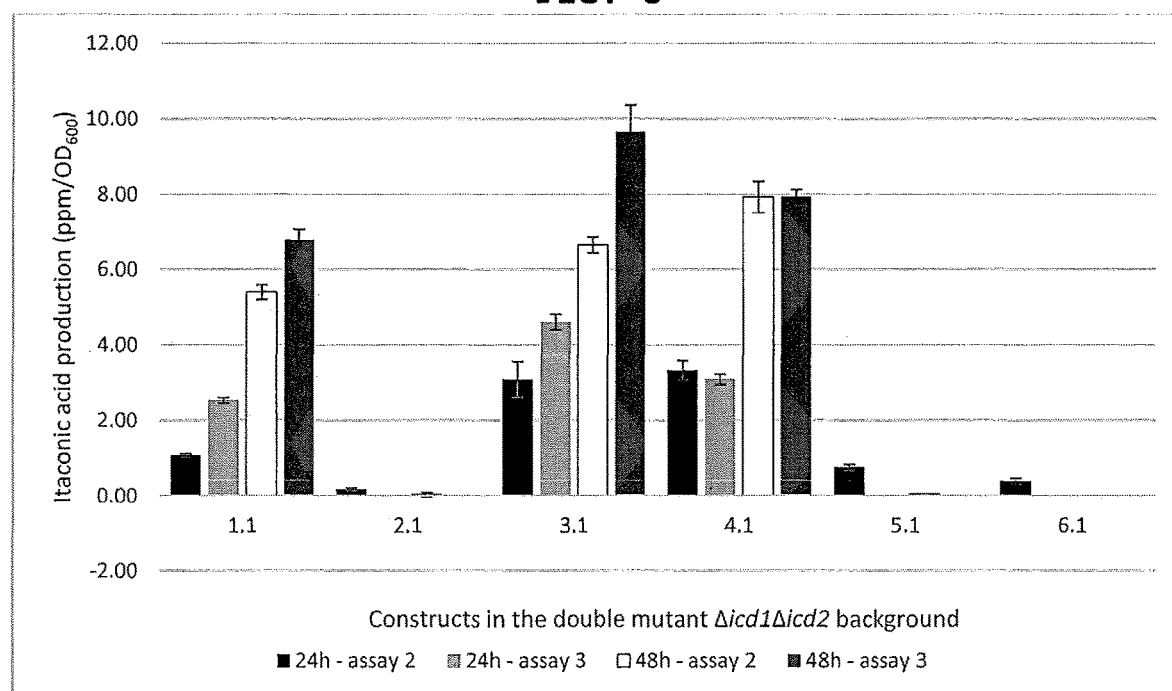
FIG. 3 shows itaconic acid production for various constructs in the *C. necator* mutant ΔphaCAB ΔA0006-9 Δicd1 Δicd2 background (double mutant) after growth with (assay 2) or without glutamic acid (assay 3). The results are indicated in ppm/$OD_{600}$. The error bars are representative of standard deviations between replicates. 1.1: At cad1; 2.1: At cad1, Cn acnA, Cn acnB; 3.1: At cad1, Cg gltA; 4.1: At cad1, Cn gltA; 5.4: At cad1, Cg gltA, Cn acnA, Cn acnB; 6.1: At cad1, Cn gltA, Cn acnA, Cn acnB.
Figure 4:
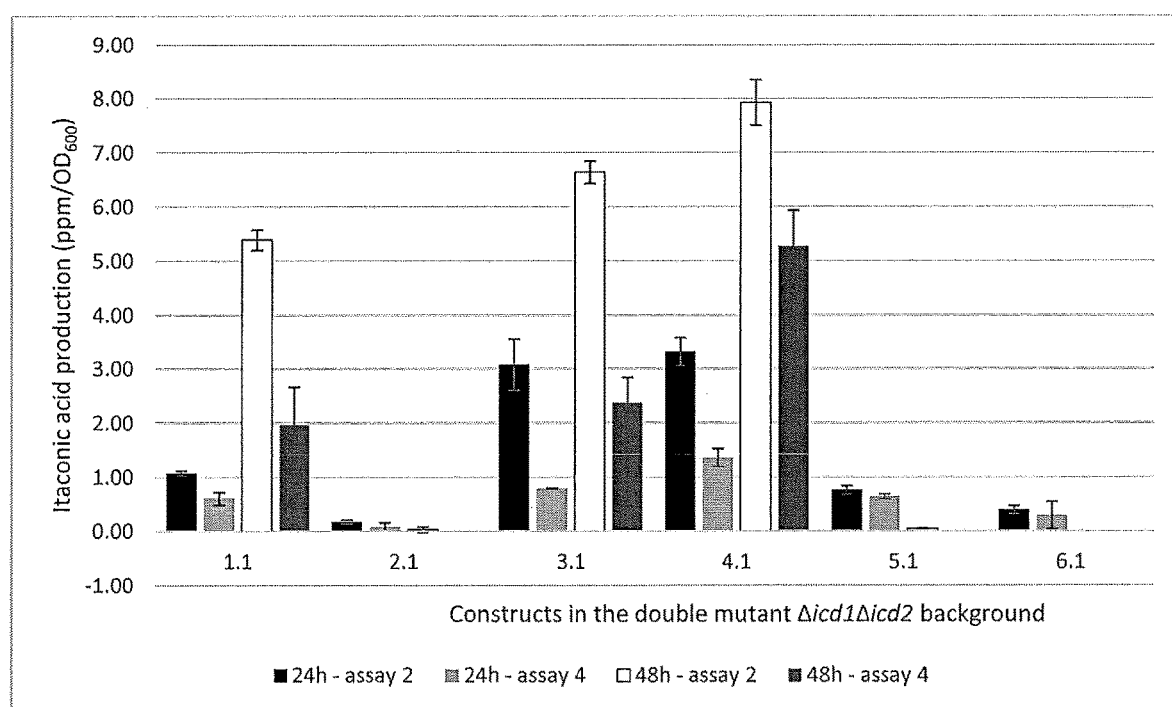
FIG. 4 shows itaconic acid production for various constructs in the *C. necator* mutant ΔphaCAB ΔA0006-9 Δicd1 Δicd2 background (double mutant) after induction at $OD_{600}$ 0.35-0.5 (assay 2) or $OD_{600}$ 0.7-0.9 (assay 4).
Figure 5:
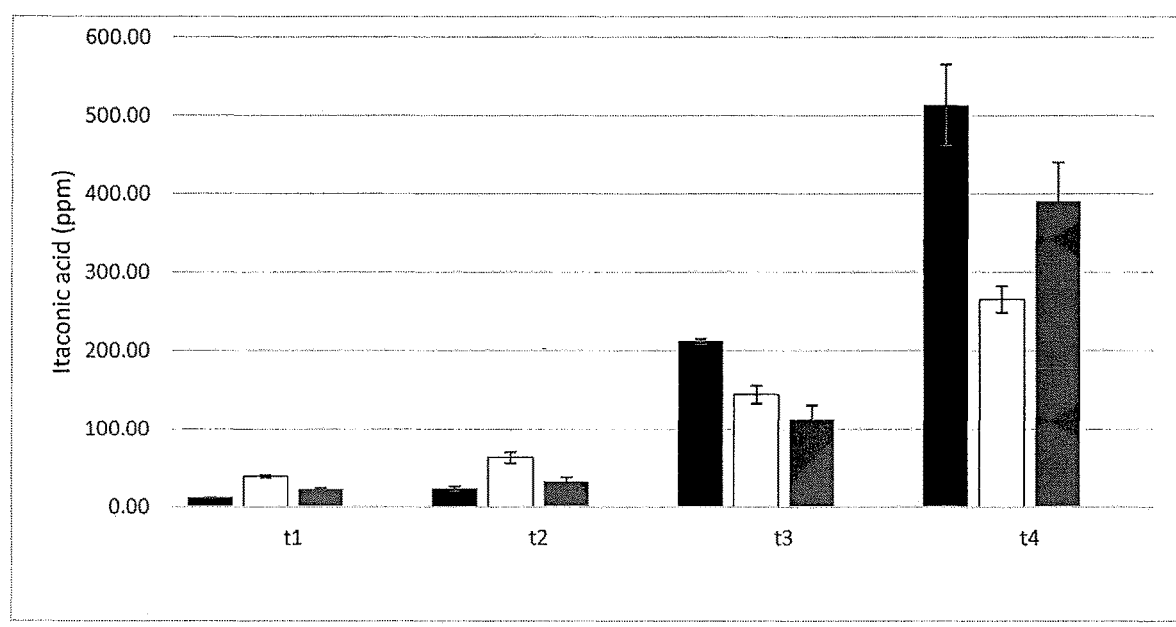
FIG. 5 shows itaconic acid titers at 4 timepoints (t1 to t4) over the course of a fed-batch cultivation of the strains double mutant-1.1 (DM-1.1; black bars), double mutant-3.1 (DM-3.1; unfilled bars) and double mutant-4.1 (DM 4.1; dark grey-filled bars). The timepoints are t1: 17 h post-induction, no feed; t2: 24 h post-feed; t3: 36 h post-feed, mid feed and t4: end of run (66 h post-inoculation). Itaconic acid titers were not detectable in double mutant-1A-pBAD (DM-1A-pBAD).
Figure 6:
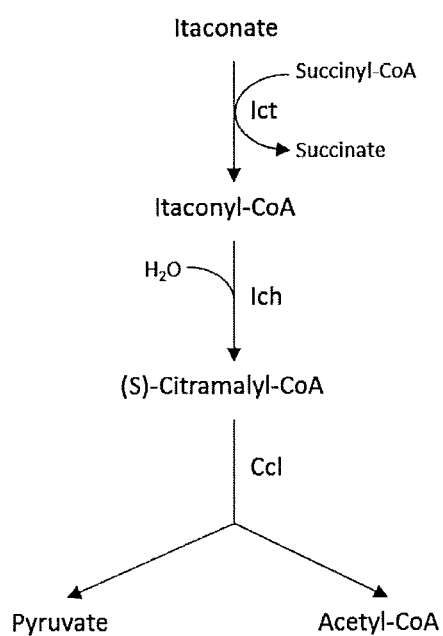
FIG. 6 shows an exemplary pathway of itaconic acid degradation.

The present invention provides processes for biosynthesis of compounds involved in the TCA cycle, and/or derivatives thereof, and/or compounds related thereto, organisms altered to increase biosynthesis of compounds involved in the TCA cycle, derivatives thereof and compounds related thereto, exogenous genetic molecules of these altered organisms, and bio-derived, bio-based, or fermentation-derived products biosynthesized or otherwise produced by any of these methods and/or altered organisms.

In one aspect of the present invention, an organism is engineered or redirected to produce compounds involved in the TCA cycle, as well as derivatives and compounds related thereto, by alteration of the organism to express a cis-aconitate decarboxylase, a citrate synthase and/or an aconitate hydratase, or a polypeptide or oligopeptide having the activity of a cis-aconitate decarboxylase, a citrate synthase and/or an aconitate hydratase. Organisms produced in accordance with the present invention are useful in methods for biosynthesizing higher levels of compounds involved in the TCA cycle, derivatives thereof, and compounds related thereto.

For purposes of the present invention, by "compounds involved in the TCA cycle and derivatives and compounds related thereto" it is meant to encompass itaconic acid and other C4 acids and their derivative such as but not limited to 2-propenoic acid, succinic acid and fumaric acid. For purposes of the present invention, by "derivatives and compounds related thereto" it is meant to encompass compounds derived from the same substrates and/or enzymatic reactions, as compounds involved in itaconic acid metabolism, byproducts of these enzymatic reactions and compounds with similar chemical structure including, but not limited to, structural analogs wherein one or more substituents of compounds involved in itaconic acid metabolism are replaced with alternative substituents.

For purposes of the present invention, by "higher levels of compounds involved in the TCA cycle" it is meant that the altered organisms and methods of the present invention are capable of producing increased levels of compounds involved in the TCA cycle and derivatives and compounds related thereto as compared to the same organism without alteration. In one nonlimiting embodiment, levels are increased by 2-fold or higher.

For compounds containing carboxylic acid groups such as organic monoacids, hydroxyacids, aminoacids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia and the like. The salt can be isolated as is from the system as the salt or converted to the free acid by reducing the pH to, for example, below the lowest pKa through addition of acid or treatment with an acidic ion exchange resin.

For compounds containing amine groups such as but not limited to organic amines, amino acids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as carbonic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid, and the like. The salt can be isolated as is from the system as a salt or converted to the free amine by raising the pH to, for example, above the highest pKa through addition of base or treatment with a basic ion exchange resin. Acceptable inorganic bases are known in the art and include aluminum hydroxide, calcium hydroxide, potassium hydroxide, sodium carbonate or bicarbonate, sodium hydroxide, and the like.

For compounds containing both amine groups and carboxylic acid groups such as but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as carbonic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Acceptable inorganic bases include aluminum hydroxide, calcium hydroxide, potassium hydroxide, sodium carbonate and/or bicarbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, trimethylamine, N-methylglucamine, and the like. Acceptable inorganic bases are known in the art and include aluminum hydroxide, calcium hydroxide, potassium hydroxide, sodium carbonate, sodium hydroxide, ammonia and the like. The salt can be isolated as is from the system or converted to the free acid by reducing the pH to, for example, below the pKa through addition of acid or treatment with an acidic ion exchange resin. In one or more aspects of the invention, it is understood that the amino acid salt can be isolated as: i. at low pH, as the ammonium (salt)-free acid form; ii. at high pH, as the amine-carboxylic acid salt form; and/or iii. at neutral or midrange pH, as the free-amine acid form or zwitterion form.

In the process for biosynthesis of compounds involved in the TCA cycle and derivatives and compounds related thereto of the present invention, an organism capable of producing compounds involved in the TCA cycle and derivatives and compounds related thereto is obtained. The organism is then altered to produce more compounds involved in the TCA cycle and derivatives and compounds related thereto in the altered organism as compared to the unaltered organism.

In one nonlimiting embodiment, the organism is *Cupriavidus necator* (*C. necator*) or an organism with properties similar thereto. A nonlimiting embodiment of the organism is set for at lgcstandards-atcc with the extension.org/products/all/17699.aspx?geocountry=gb#generalinformation of the world wide web.

*C. necator* (previously called *Hydrogenomonas eutrophus, Alcaligenes eutropha, Ralstonia eutropha,* and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar, N. S. & Casida, L. E. Int. J. of Systematic Bacteriology 1987 37(4): 323-326), bacterial predation (Byrd et al. Can J Microbiol 1985 31:1157-1163; Sillman, C. E. & Casida, L. E. Can J Microbiol 1986 32:760-762; Zeph, L. E. & Casida, L. E. Applied and Environmental Microbiology 1986 52(4):819-823) and polyhydroxybutyrate (PHB) synthesis. In addition, the cells have been reported to be capable of both aerobic and nitrate dependent anaerobic growth. A nonlimiting example of a *C. necator* organism useful in the present invention is a *C. necator* of the H16 strain. In one nonlimiting embodiment, a *C. necator* host of the H16 strain with at least a portion of the phaCAB gene locus knocked out (ΔphaCAB) is used.

In another nonlimiting embodiment, the organism altered in the process of the present invention has one or more of the above-mentioned properties of *Cupriavidus necator*.

In another nonlimiting embodiment, the organism is selected from members of the genera *Ralstonia, Wautersia, Cupriavidus, Alcaligenes, Burkholderia* or *Pandoraea*.

For the process of the present invention, the organism is altered to express a cis-aconitate decarboxylase, a citrate synthase and/or an aconitate hydratase.

In one nonlimiting embodiment, the organism is altered to express a cis-aconitate decarboxylase. In one nonlimiting embodiment, the cis-aconitate decarboxylase comprises *A. terreus* CadA (SEQ ID NO:1) or a polypeptide with similar enzymatic activities exhibiting at least about 50%, 60%, 70%, 75%, 80%, 85%, 90%, 910, 92%, 93%, 94%, 95%, 96%, 97%, 98%, 99% or 99.5% sequence identity to an amino acid sequence set forth in SEQ ID NO: 1 or a functional fragment thereof. In one nonlimiting embodiment, the cis-aconitate decarboxylase is encoded by a nucleic acid sequence comprising *A. terreus* cad1 (SEQ ID NO:2) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 2 or a functional fragment thereof. In one nonlimiting embodiment, the cis-aconitate decarboxylase is CadA classified in EC 4.1.1.6.

In one nonlimiting embodiment, the organism is altered to express a citrate synthase. In one nonlimiting embodiment, the citrate synthase comprises *C. glutamicum* or *C. necator* GltA (SEQ ID NO:3 or 5) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 3 or 5 or a functional fragment thereof. In one nonlimiting embodiment, the citrate synthase is encoded by a nucleic acid sequence comprising *C. glutamicum* or *C. necator* gltA (SEQ ID NO:4, 6 or 7) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 4, 6 or 7 or a functional fragment thereof. In one nonlimiting embodiment, the citrate synthase is GltA classified in EC 2.3.3.16.

In one nonlimiting embodiment, the organism is altered to express an aconitate hydratase. In one nonlimiting embodiment, the aconitate hydratase comprises *C. necator* AcnA or AcnB (SEQ ID NO:8 or 10) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 8 or 10 or a functional fragment thereof. In one nonlimiting embodiment, the aconitate hydratase is encoded by a nucleic acid sequence comprising *C. necator* acnA or acnB (SEQ ID NO:9 or 11) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO:9 or 11 or a functional fragment thereof. In one nonlimiting embodiment, the aconitate hydratase is AcnA or AcnB classified in EC 4.2.1.3.

In one nonlimiting embodiment, the nucleic acid sequence is codon optimized for *C. necator*.

In one nonlimiting embodiment, the organism is altered to express two or more of the enzymes of cis-aconitate decarboxylase, citrate synthase and/or aconitate hydratase as disclosed herein.

In one nonlimiting embodiment, the organism is altered to express a cis-aconitate decarboxylase, a citrate synthase and an aconitate hydratase as disclosed herein.

In one nonlimiting embodiment, the organism is further altered to inactivate the metabolic flow downstream of cis-aconitate. In one nonlimiting embodiment, isocitrate dehydrogenase activity is inactivated. In one nonlimiting embodiment, the genes icd1 and/or icd2 are eliminated. In some embodiments, genes pta, pyk and/or ldhA are deleted.

Itaconate is first converted into itaconyl-CoA by a succinyl-CoA:itaconate-CoA transferase (Ict, EC:2.8.3.-2.8.3.22) using succinyl-CoA as the donor. Itaconyl-CoA is then hydrated to (S)-citramalyl-CoA by an itaconyl-CoA hydratase (Ich, EC:4.2.1.56 4.2.1.-). Finally, the (S)-citramalyl-CoA is cleaved into acetyl-CoA and pyruvate by an (S)-citramalyl-CoA lyase (Ccl, EC:4.1.3.25) (see FIG. 7). Accordingly, in one nonlimiting embodiment, the organism is modulated to decrease degradation of itaconic acid. In one nonlimiting embodiment, Ict classified in EC:2.8.3.-, Ich classified in EC: 4.2.1.-, Ccl classified in EC:4.1.3.- and/or Suc classified in EC:6.2.1.- is downregulated, deleted or mutated. In one nonlimiting embodiment Ict is classified as EC: 2.8.3.22. In one nonlimiting embodiment, Ich is classified as EC:4.2.1.56. In one nonlimiting embodiment, Ccl is classified as EC:4.1.3.25. In one nonlimiting embodiment, Suc is classified as EC:6.2.1.5. In one nonlimiting embodiment, a gene identified in Table 5 is downregulated, deleted or mutated.

In one nonlimiting embodiment, the organism is further modified to eliminate phaCAB, involved in PHBs production and/or H16-A0006-9 encoding endonucleases thereby improving transformation efficiency as described in U.S. patent application Ser. No. 15/717,216, teachings of which are incorporated herein by reference.

In the process of the present invention, the altered organism is then subjected to conditions wherein compounds involved in the TCA cycle and derivatives and compounds related thereto are produced.

In one nonlimiting embodiment, glutamic acid is added during fermentation.

In the process described herein, a fermentation strategy can be used that entails anaerobic, micro-aerobic or aerobic cultivation. A fermentation strategy can entail nutrient limitation such as nitrogen, phosphate or oxygen limitation.

Under conditions of nutrient limitation a phenomenon known as overflow metabolism (also known as energy spilling, uncoupling or spillage) occurs in many bacteria (Russell, J. B. Journal of Molecular Microbiology and Biotechnology 2007 13:1-11). In growth conditions in which there is a relative excess of carbon source and other nutrients (e.g. phosphorous, nitrogen and/or oxygen) that are limiting cell growth, overflow metabolism results in the use of this excess energy (or carbon), not for biomass formation but for the excretion of metabolites, typically organic acids. In *Cupriavidus necator* a modified form of overflow metabolism occurs in which excess carbon is sunk intracellularly into the storage carbohydrate polyhydroxybutyrate (PHB). In strains of *C. necator* which are deficient in PHB synthesis this overflow metabolism can result in the production of extracellular overflow metabolites. The range of metabolites that have been detected in PHB deficient *C. necator* strains include acetate, acetone, butanoate, cis-aconitate, citrate, ethanol, fumarate, 3-hydroxybutanoate, propan-2-ol, malate, methanol, 2-methyl-propanoate, 2-methyl-butanoate, 3-methyl-butanoate, 2-oxoglutarate, meso-2,3-butanediol, acetoin, DL-2,3-butanediol, 2-methylpropan-1-ol, propan-1-ol, lactate 2-oxo-3-methylbutanoate, 2-oxo-3-methylpentanoate, propanoate, succinate, formic acid and pyruvate. The range of overflow metabolites produced in a particular fermentation can depend upon the limitation applied (e.g. nitrogen, phosphate, oxygen), the extent of the limitation, and the carbon source provided (Schlegel, H. G. & Vollbrecht, D. Journal of General Microbiology 1980 117:475-481; Steinbüchel, A. & Schlegel, H. G. Appl Microbiol Biotechnol 1989 31: 168; Vollbrecht et al. Eur J Appl Microbiol Biotechnol 1978 6:145-155; Vollbrecht et al. European J. Appl. Microbiol. Biotechnol. 1979 7: 267; Vollbrecht, D. & Schlegel, H. G. European J. Appl. Microbiol. Biotechnol. 1978 6: 157; Vollbrecht, D. & Schlegel, H. G. European J. Appl. Microbiol. Biotechnol. 1979 7: 259).

Applying a suitable nutrient limitation in defined fermentation conditions can thus result in an increase in the flux through a particular metabolic node. The application of this knowledge to *C. necator* strains genetically modified to produce desired chemical products via the same metabolic node can result in increased production of the desired product.

A cell retention strategy using a ceramic hollow fiber membrane can be employed to achieve and maintain a high cell density during fermentation. The principal carbon source fed to the fermentation can derive from a biological or non-biological feedstock. The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles or municipal waste such as fruit peel/pulp. The non-biological feedstock can be, or can derive from, natural gas, syngas, $CO_2/H_2$, CO, $H_2$, $O_2$, methanol, ethanol, non-volatile residue (NVR) a caustic wash waste stream from cyclohexane oxidation processes or waste stream from a chemical industry such as, but not limited to a carbon black industry or a hydrogen-refining industry, or petrochemical industry, a nonlimiting example being a PTA-waste stream.

In one nonlimiting embodiment, at least one of the enzymatic conversions of the production method comprises gas fermentation within the altered *Cupriavidus necator* host, or a member of the genera *Ralstonia, Wautersia, Alcaligenes, Burkholderia* and *Pandoraea*, and other organism having one or more of the above-mentioned properties of *Cupriavidus necator*. In this embodiment, the gas fermentation may comprise at least one of natural gas, syngas, $CO_2/H_2$, CO, $H_2$, $O_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO_2/H_2$.

The methods of the present invention may further comprise recovering produced compounds involved in the TCA cycle or derivatives or compounds related thereto. Once produced, any method can be used to isolate the compound or compounds involved in the TCA cycle or derivatives or compounds related thereto.

The present invention also provides altered organisms capable of biosynthesizing increased amounts of compounds involved in the TCA cycle and derivatives and compounds related thereto as compared to the unaltered organism. In one nonlimiting embodiment, the altered organism of the present invention is a genetically engineered strain of *Cupriavidus necator* capable of producing compounds involved in the TCA cycle and derivatives and compounds related thereto. In another nonlimiting embodiment, the organism to be altered is selected from members of the genera *Ralstonia, Wautersia, Alcaligenes, Cupriavidus, Burkholderia* and *Pandoraea*, and other organisms having one or more of the above-mentioned properties of *Cupriavidus necator*. In one nonlimiting embodiment, the present invention relates to a substantially pure culture of the altered organism capable of producing compounds involved in the TCA cycle and derivatives and compounds related thereto via a cis-aconitate decarboxylase, a citrate synthase and/or an aconitate hydratase pathway.

As used herein, a "substantially pure culture" of an altered organism is a culture of that microorganism in which less than about 40% (i.e., less than about 35%; 30%; 25%; 20%; 150; 100; 50; 20; 10; 0.50; 0.250; 0.10; 0.010; 0.001%; 0.0001%; or even less) of the total number of viable cells in the culture are viable cells other than the altered microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of altered microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In one nonlimiting embodiment, the altered organism of the present invention comprises at least one genome-integrated synthetic operon encoding an enzyme.

In one nonlimiting embodiment, the altered organism is produced by integration of a synthetic operon encoding a cis-aconitate decarboxylase, a citrate synthase and/or an aconitate hydratase.

In one nonlimiting embodiment, the cis-aconitate decarboxylase is from *A. terreus*. In one nonlimiting embodiment, the cis-aconitate decarboxylase comprises *A. terreus* CadA (SEQ ID NO:1) or a polypeptide with similar enzymatic activities exhibiting at least about 50%, 60%, 70%, 75%, 80%, 85%, 90%, 910, 92%, 93%, 94%, 95%, 96%, 97%, 98%, 99% or 99.5% sequence identity to an amino acid sequence set forth in SEQ ID NO: 1 or a functional fragment thereof. In one nonlimiting embodiment, the cis-aconitate decarboxylase is encoded by a nucleic acid sequence comprising *A. terreus* cad1 (SEQ ID NO:2) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 2 or a functional fragment thereof. In one nonlimiting embodiment, the cis-aconitate decarboxylase is CadA classified in EC 4.1.1.6.

In one nonlimiting embodiment, the citrate synthase is from *C. glutamicum* or *C. necator*. In one nonlimiting embodiment, the citrate synthase comprises *C. glutamicum* or *C. necator* GltA (SEQ ID NO:3 or 5) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 3 or 5 or a functional fragment thereof. In one nonlimiting embodiment, the citrate synthase is encoded by a nucleic acid sequence comprising *C. glutamicum* or *C. necator* gltA (SEQ ID NO:4, 6 or 7) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 4, 6 or 7 or a functional fragment thereof. In one nonlimiting embodiment, the citrate synthase is GltA classified in EC 2.3.3.16.

In one nonlimiting embodiment, the aconitate hydratase is from *C. necator*. In one nonlimiting embodiment, the aconitate hydratase comprises *C. necator* AcnA or AcnB (SEQ ID NO:8 or 10) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 8 or 10 or a functional fragment thereof. In one nonlimiting embodiment, the aconitate hydratase is encoded by a nucleic acid sequence comprising *C. necator* acnA or acnB (SEQ ID NO:9 or 11) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO:9 or 11 or a functional fragment thereof. In one nonlimiting embodiment, the aconitate hydratase is AcnA or AcnB classified in EC 4.2.1.3.

In one nonlimiting embodiment, the nucleic acid sequence is codon optimized for *C. necator*.

In one nonlimiting embodiment, the organism is altered to express two or more of the enzymes of cis-aconitate decarboxylase, citrate synthase and/or aconitate hydratase as disclosed herein.

In one nonlimiting embodiment, the organism is altered to express a cis-aconitate decarboxylase, a citrate synthase and an aconitate hydratase as disclosed herein.

In one nonlimiting embodiment, the organism is further altered to inactivate the metabolic flow downstream of cis-aconitate. In one nonlimiting embodiment, isocitrate dehydrogenase activity is inactivated. In one nonlimiting embodiment, the genes icd1 and/or icd2 are eliminated. In some embodiments, genes pta, pyk and/or ldhA are deleted.

In one nonlimiting embodiment, the organism is modulated to decrease degradation of itaconic acid. In one nonlimiting embodiment, Ict classified in EC:2.8.3.-, Ich classified in EC: 4.2.1.-, Ccl classified in EC:4.1.3.- and/or Suc classified in EC:6.2.1.- is downregulated, deleted or mutated. In one nonlimiting embodiment Ict is classified as EC: 2.8.3.22. In one nonlimiting embodiment, Ich is classified as EC:4.2.1.56. In one nonlimiting embodiment, Ccl is classified as EC:4.1.3.25. In one nonlimiting embodiment, Suc is classified as EC:6.2.1.5. In one nonlimiting embodiment, a gene identified in Table 5 is downregulated, deleted or mutated.

In one nonlimiting embodiment, the organism is further modified to eliminate phaCAB, involved in PHBs production and/or H16-A0006-9 encoding endonucleases thereby improving transformation efficiency.

The percent identity (and/or homology) between two amino acid sequences as disclosed herein can be determined as follows. First, the amino acid sequences are aligned using the BLAST 2 Sequences (B12seq) program from the stand-alone version of BLAST containing BLASTP version 2.0.14. This stand-alone version of BLAST can be obtained from the U.S. government's National Center for Biotechnology Information web site (www with the extension ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the polypeptides or nucleic acid sequences described herein can also be used in the methods and organisms disclosed herein. The term "functional fragment" as used herein refers to a peptide fragment of a polypeptide or a nucleic acid sequence fragment encoding a peptide fragment of a polypeptide that has at least about 25% (e.g., at least about 30%; 40%; 50%; 60%; 70%; 75%; 80%; 85%; 90%; 95%; 98%; 99%; 100%; or even greater than 100%) of the activity of the corresponding mature, full-length, polypeptide. The functional fragment can generally, but not always, be comprised of a continuous region of the polypeptide, wherein the region has functional activity.

Functional fragments may range in length from about 10% up to 99% (inclusive of all percentages in between) of the original sequence.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine, hemagluttanin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Endogenous genes of the organisms altered for use in the present invention also can be disrupted to prevent the formation of undesirable metabolites or prevent the loss of intermediates in the pathway through other enzymes acting on such intermediates. In one nonlimiting embodiment, the organism is further altered to inactivate the metabolic flow downstream of cis-aconitate. In one nonlimiting embodiment, isocitrate dehydrogenase activity is inactivated. In one nonlimiting embodiment, the genes icd1 and/or icd2 are eliminated. In some embodiments, genes pta, pyk and/or ldhA are deleted. In one nonlimiting embodiment, the organism is further modified to eliminate phaCAB, involved in PHBs production and/or H16-A0006-9 encoding endonucleases thereby improving transformation efficiency.

Thus, as described herein, altered organisms can include exogenous nucleic acids encoding a cis-aconitate decarboxylase, a citrate synthase and/or an aconitate hydratase, as described herein, as well as modifications to endogenous genes.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host or organism once in or utilized by the host or organism. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

The present invention also provides exogenous genetic molecules of the non-naturally occurring organisms disclosed herein such as, but not limited to, codon optimized nucleic acid sequences, expression constructs and/or synthetic operons.

In one nonlimiting embodiment, the exogenous genetic molecule comprises a codon optimized nucleic acid sequence encoding a cis-aconitate decarboxylase, a citrate synthase and/or an aconitate hydratase. In one nonlimiting embodiment, the nucleic acid sequence is codon optimized for *C. necator*.

In one nonlimiting embodiment, the exogenous genetic molecule comprises a nucleic acid sequence encoding a cis-aconitate decarboxylase. In one nonlimiting embodiment, the nucleic acid sequence comprises SEQ ID NO:2 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 2 or a functional fragment thereof.

In one nonlimiting embodiment, the exogenous genetic molecule comprises a nucleic acid sequence encoding a citrate synthase. In one nonlimiting embodiment the nucleic acid sequence comprises SEQ ID NO:4, 6 or 7 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 4, 6 or 7 or a functional fragment thereof.

In one nonlimiting embodiment, the exogenous genetic molecule comprises a nucleic acid sequence encoding an aconitate hydratase. In one nonlimiting embodiment, the exogenous genetic molecule comprises SEQ ID NO:9 or 11 or a nucleic acid sequence encoding a polypeptide with similar enzymatic activities exhibiting at least about 50%, 60%, 70%, 75%, 80%, 85%, 90%, 910, 92%, 93%, 94%, 95%, 96%, 97%, 98%, 99% or 99.5% sequence identity to the nucleic acid sequence set forth in SEQ ID NO:9 or 11 or a functional fragment thereof.

Additional nonlimiting examples of exogenous genetic molecules include expression constructs of, for example, a cis-aconitate decarboxylase, a citrate synthase and/or an aconitate hydratase and synthetic operons of, for example, a cis-aconitate decarboxylase, a citrate synthase and/or an aconitate hydratase.

Also provided by the present invention are compounds involved in the TCA cycle and derivatives and compounds related thereto bioderived from an altered organism according to any of methods described herein.

Further, the present invention relates to means and processes for use of these means for biosynthesis of compounds involved in the TCA cycle, derivatives thereof and/or compounds related thereto. Nonlimiting examples of such means include altered organisms and exogenous genetic molecules as described herein as well as any of the molecules as depicted in FIG. 1.

In addition, the present invention provides bio-derived, bio-based, or fermentation-derived products produced using the methods and/or altered organisms disclosed herein. In one nonlimiting embodiment, a bio-derived, bio-based or fermentation derived product is produced in accordance with the exemplary central metabolism depicted in FIG. 1. Examples of such products include, but are not limited to, compositions comprising at least one bio-derived, bio-based, or fermentation-derived compound or any combination thereof, as well as plastics, resins and rubber like resins, latex, detergents, paper, thickeners, shampoos, industrial cleaners and carpet backing, molded substances, formulations and semi-solid or non-semi-solid streams comprising one or more of the bio-derived, bio-based, or fermentation-derived compounds or compositions, combinations or products thereof.

Six different combinations of genes were constructed and transferred into two C. necator backgrounds, the wild-type strain, in which the TCA cycle is intact, and the double mutant ΔphaCAB ΔA0006-9 Δicd1 Δicd2 in which the metabolic flux of the TCA cycle downstream of the itaconic acid precursor has been interrupted. Itaconic acid levels produced by these strains were evaluated after growth in tubes or in fermentative conditions.

Improvement of the metabolic flow to itaconic acid via citrate in constructs overexpressing an aconitate hydratase was assessed. acnA and acnB have been detected as being expressed when C. necator is grown on fructose as carbon source (Table 1). Therefore, both genes were selected to test the impact of their overexpression on itaconic acid production.

The effects of overexpression of C. necator and C. glutamicum gltA, in addition to cad1, on itaconic acid production was also assessed.

Moreover, as studies have demonstrated that inactivating the metabolic flow downstream of cis-aconitate in the TCA cycle results in improved itaconic acid titers (Okamoto et al. J Gen Appl Microbiol. 2014. 60(5):191-7 Harder et al. Metab Eng. 2016. 38:29-37), a knock out strain with genes encoding isocitrate dehydrogenases was generated and assessed for itaconic acid production. Specifically, the double mutant Δicd1Δicd2 was generated (full genotype ΔphaCAB ΔA0006-9 Δicd1 Δicd2).

Table 1 provides expression levels for TCA cycle-related enzymatic activities. The genes with highest expression are indicated in bold. The expression units correspond to the relative expression unit, which is the expression normalized to the total number of mapped reads for each sample with an average of 3 biological replicates. DF and DDF refer to the strains ΔphaCAB and ΔphaCABΔpimACD respectively grown with fructose as sole carbon source.

TABLE 1

| | DF AVERAGE | DDF AVERAGE | Protein Name | Gene Name | Description |
|---|---|---|---|---|---|
| YP_728522 | 0.67 | 0.78 | | H16_B0357 | citrate synthase |
| YP_728578 | 1.15 | 1.98 | | H16_B0414 | citrate synthase |
| YP_725737 | 1.17 | 0.00 | | H16_A1229 | citrate synthase |
| YP_841723 | 2.48 | 2.28 | | H16_B2211 | citrate synthase |
| YP_727077 | 145.07 | 145.07 | GltA | H16_A2627 | type II citrate synthase |
| YP_726376 | 14.77 | 13.05 | AcnM | H16_A1907 | aconitate hydratase |
| YP_728730 | 105.98 | 105.98 | AcnB | H16_B0568 | bifunctional aconitate hydratase 2/2-methylisocitrate dehydratase |
| YP_727088 | 200.70 | 210.51 | AcnA | H16_A2638 | aconitate hydratase |
| YP_729172 | 3.38 | 2.63 | Icd3 | H16_B1016 | isocitrate dehydrogenase [NAD] |
| YP_727499 | 103.52 | 101.55 | Icd1 | H16_A3056 | isocitrate dehydrogenase |
| YP_841443 | 124.51 | 123.04 | Icd2 | H16_B1931 | isocitrate dehydrogenase [NADP] |
| YP_726692 | 11.88 | 9.71 | IclB | H16_A2227 | isocitrate lyase |
| YP_726676 | 25.00 | 19.58 | IclA | H16_A2211 | isocitrate lyase |

Table 2 shows the genes used in assemblies of the genetic constructs of the present invention. All the constructs were assembled using standard cloning procedures such as described, for example in Green and Sambrook, Molecular Cloning, A Laboratory Manual, Nov. 18, 2014.

TABLE 2

| Gene | Origin | GenBank or UniProt Number | Codon-optimized |
|---|---|---|---|
| cad1 | A. terreus | B3IUN8 | C. necator |
| gltA | C. necator | WP_010814621.1 | C. necator |
| gltA | C. glutamicum | NP_600058.1 | C. necator |
| acnB | C. necator | WP_010810392.1 | C. necator |
| acnA | C. necator | WP_011615748.1 | C. necator |

At: A. terreus,

Cg: C. glutamicum,

Cn: C. necator

The list of various combinations of genes for the methods of the present invention are included in Table 3.

TABLE 3

| Plasmid | Genotype | Genes | Antibiotics marker |
|---|---|---|---|
| 1.1 | pBBR1-1A-pBAD-RBS-SEQ ID NO 2-rrnBT1 | At_cad1 | Kan |
| 2.1 | pBBR1-1A-pBAD-RBS- SEQ ID NO 2-RBS- SEQ ID NO 9-RBS- SEQ ID NO 11-rrnBT1 | At_cad1, Cn_acnA, Cn_acnB | Kan |
| 3.1 | pBBR1-1A-pBAD-RBS- SEQ ID NO 2-RBS- SEQ ID NO 4-rrnBT1 | At_cad1, Cg_gltA | Kan |
| 4.1 | pBBR1-1A-pBAD-RBS- SEQ ID NO 2-RBS- SEQ ID NO 6-rrnBT1 | At_cad1, Cn_gltA | Kan |
| 5.4 | pBBR1-1A-pBAD-RBS- SEQ ID NO 2-RBS- SEQ ID NO 7-RBS- SEQ ID NO 9-RBS- SEQ ID NO 11-rrnBT1 | At_cad1, Cg_gltA, Cn_acnA, Cn_acnB | Kan |
| 6.1 | pBBR1-1A-pBAD-RBS- SEQ ID NO 2-RBS- SEQ ID NO 6-RBS- SEQ ID NO 9-RBS- SEQ ID NO 11-rrnBT1 | At_cad1, Cn_gltA, Cn_acnA, Cn_acnB | Kan |
| 1A-pBAD | pBBR1-1A-pBAD | — | Kan |

Note:
RBS is ribosome binding site; -rrnBT1 is terminator sequence.
At: *A. terreus*,
Cg: *C. glutamicum*,
Cn: *C. necator*

The genotypes in Table 3 describe constructs used to transform *C. necator* wt, in which the TCA cycle is functional, and in the double mutant ΔicdlΔicd2 by electroporation using standard procedures.

A list of the bacterial strains of the present invention is provided in Table 4. The numbers 1.1, 1.2, 1.3, 1.4, 5.4, and 6.1 refer to the plasmids in Table 3.

TABLE 4

| Strain as referred to in this study | Host | Genotype |
|---|---|---|
| wt | *C. necator* H16 | ΔphaCAB ΔH16_A0006-9 |
| Double mutant | *C. necator* H16 | ΔphaCAB ΔH16_A0006-9 Δicd1 Δicd2 |
| wt-1.1 | *C. necator* H16 | ΔphaCAB ΔH16_A0006-9 1.1 |
| wt-2.1 | *C. necator* H16 | ΔphaCAB ΔH16_A0006-9 2.1 |
| wt-3.1 | *C. necator* H16 | ΔphaCAB ΔH16_A0006-9 3.1 |
| wt-4.1 | *C. necator* H16 | ΔphaCAB ΔH16_A0006-9 4.1 |
| wt-5.4 | *C. necator* H16 | ΔphaCAB ΔH16_A0006-9 5.4 |
| wt-6.1 | *C. necator* H16 | ΔphaCAB ΔH16_A0006-9 6.1 |
| wt-1ApBAD | *C. necator* H16 | ΔphaCAB ΔH16_A0006-9 1A-BAD |
| Double mutant -1.1 | *C. necator* H16 | ΔphaCAB ΔH16_A0006-9 Δicd1 Δicd2 1.1 |
| Double mutant -2.1 | *C. necator* H16 | ΔphaCAB ΔH16_A0006-9 Δicd1 Δicd2 2.1 |
| Double mutant -3.1 | *C. necator* H16 | ΔphaCAB ΔH16_A0006-9 Δicd1 Δicd2 3.1 |
| Double mutant -4.1 | *C. necator* H16 | ΔphaCAB ΔH16_A0006-9 Δicd1 Δicd2 4.1 |
| Double mutant -5.4 | *C. necator* H16 | ΔphaCAB ΔH16_A0006-9 Δicd1 Δicd2 5.4 |
| Double mutant -6.1 | *C. necator* H16 | ΔphaCAB ΔH16_A0006-9 Δicd1 Δicd2 6.1 |
| Double mutant - 1ApBAD | *C. necator* H16 | ΔphaCAB ΔH16_A0006-9 Δicd1 Δicd2 1A-pBAD |

Itaconic acid production assays were performed as described in the Examples and results are depicted in FIGS. 2, 3, 4 and 5. Itaconic acid production was detected for the strains carrying the *A. terreus* cad1 gene, encoding an aconitate decarboxylase, by itself or in combination with other TCA cycle genes including *C. glutamicum* gltA gene, encoding a citrate synthase, under the inducible pBAD promoter. Peak titers obtained for the best producing strains reached 30-100 ppm at 48 h post-induction in tube assays and 300-500 ppm at 60 h post-induction in fed-batch conditions. In addition, the impact of glutamic acid addition to the media or of the cell density at induction on itaconic acid production was assessed. Measurement of itaconic acid titers of more than 100 ppm in fed-batch conditions is indicative of carbon flux through the TCA cycle in *C. necator*.

The following section provides further illustration of the methods and materials of the present invention. These Examples are illustrative only and are not intended to limit the scope of the present invention.

EXAMPLES

Bioassay

Figure 7:
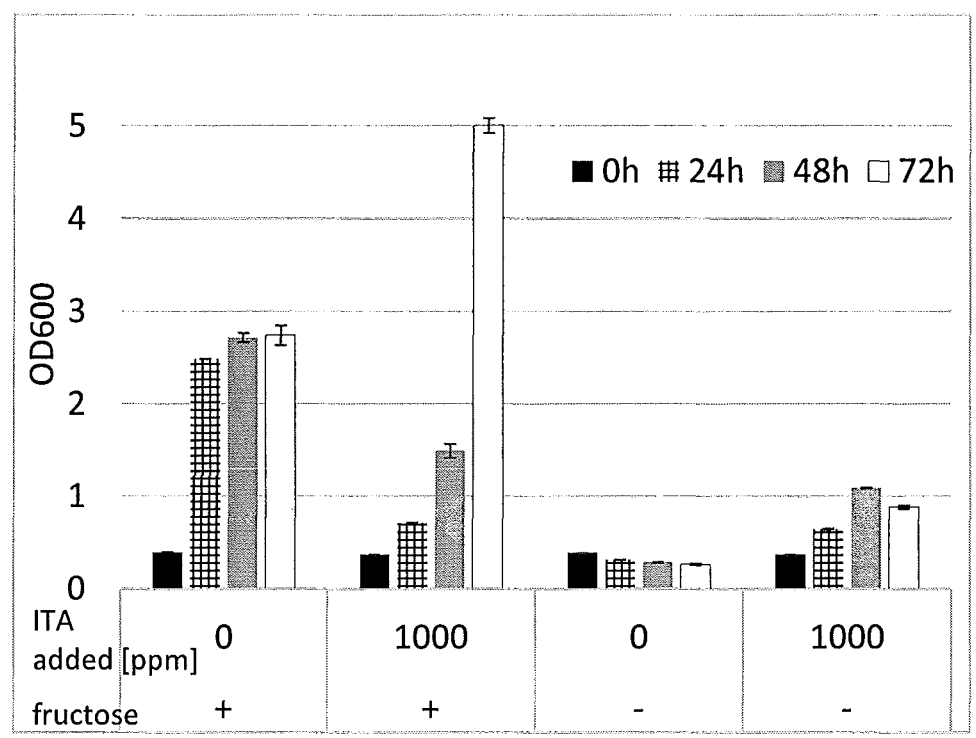
FIG. 7 shows OD600 measurements for the samples collected at 0, 24, 48 and 72 hours. The growth of the cultures was measured with or without itaconic acid (1 g/L) and in presence (+) or absence of fructose (−).

The standard, representative workflow for the bioassay of *C. necator* strains to measure non-volatile products is described in FIG. 7. In the assays for itaconic acid production, typically 3 precultures for each strain were grown for 24 h at 30° C. in 10 ml TSB supplemented with kanamycin (300 μg/ml) and were pooled together before centrifuging the cells and resuspending pelleted cells in 1.5 ml minimal medium. For the assays performed with growth in the presence of glutamic acid (Assays 2 and 4), 1.5 g/l (final concentration) of glutamic acid was also added to the precultures and cultures. The pooled cells resuspended in minimal medium were then used to inoculate three independent cultures.

For the assays 2 and 3, the cultures were inoculated at an $OD_{600}$ between 0.2 and 0.3 instead of 0.4-0.5. They also were induced at an $OD_{600}$ between 0.35 and 0.5 instead of 0.7-0.9. Two ml of each culture was collected at 24 h and 48 h after induction. The $OD_{600}$ were measured and the samples were kept at 4° C. or −20° C. before being treated for LC-MS analysis.

Measurement of Itaconic Acid Production

The samples collected at 24 h and 48 h were centrifuged and the clarified supernatants were subject to LC-MS analysis for detection of itaconic acid Extracellular itaconic acid concentrations of samples were determined by liquid chromatography-mass spectrometry (LC-MS). Broth samples were centrifuged and the resulting supernatants were diluted in 90% LC-MS grade acetonitrile/10% LC-MS grade water between 10- and 1000-fold, depending upon anticipated analyte concentration.

LC-MS was performed using an Agilent Technologies (Santa Clara, Calif., USA) 1290 Series Infinity HPLC system, coupled to an Agilent 6530 Series Q-TOF mass spectrometer. Manufacturer instructions were followed using a BEH Amide UPLC column: 2.1 mm diameter×50 mm length×1.7 μm particle size (Waters, Milford, Mass., USA).

External standard curves were used for quantitation. Calibration levels of 0.01, 0.02, 0.05, 0.1, 0.2, 0.5, 1, 2, 5 and 10 μg/ml were constructed in a matrix-matched solution, typically the blank medium, diluted to the same level as the samples in acetonitrile. Concentrations were determined by interpolation of sample responses against the calibration curve, using Agilent MassHunter Quantitative Analysis software. It was not possible to chromatographically resolve citric acid and isocitric acid, therefore results of these two compounds were given as a single value.

After the bioassays in tubes, strains that demonstrated production were further screened in the Ambr15f under fed batch conditions with fructose as carbon source. Samples were collected over the course of the batch and feeding portions of growth, and itaconic acid levels assessed by LC-MS.

Principally, this screening methodology allowed productivity to be quantified in high cell density cultures under stringent control, representative of the potential for pathways to achieve high titers in a simple, scalable process.

Seed Strain 10 ml cultures were first incubated with appropriate antibiotic. The 10 ml cultures were used as a direct inoculum for the subsequent fermentation fed batch cultures.

Fermentation Conditions

The Sartorius Ambr15f platform was used to screen pathway strains in a fed batch mode of operation. This system allowed control of multiple variables such as dissolved oxygen and pH. Typically, the process conditions were standardized and run following manufacturer instructions.

Sample Preparation for Analysis

Samples volumes were usually 500 μl, from which 100 μl were used for $OD_{600}$ determination and 400 μl processed for analysis. The samples were centrifuged 30 min at 2000 g and the supernatants were filtered through a 0.2 μm filter. The clarified supernatants were then subject to analysis of the itaconic acid content by LC-MS.

Itaconic Acid Degradation by *C. necator*

The strain *C. necator* H16 ΔphaCAB ΔA0006-9 Δicd1 Δicd2 (double mutant) was tested for its ability to degrade itaconic acid and to use carbon derived from degraded itaconic acid as a sole carbon source. A preculture of the strain in minimal medium was used to inoculate 10 ml of minimal medium supplemented with 1 g/l itaconic acid with or without fructose (1%) at an initial OD600 around 0.4. A negative control without itaconic acid was also included. One ml of sample was collected at 0, 24, 48 and 72 hours. For each sample, the OD600 was measured at each timepoint and the titers of itaconic acid were analyzed by HPLC-RID. The experiment was performed in triplicates for each condition.

Figure 8:
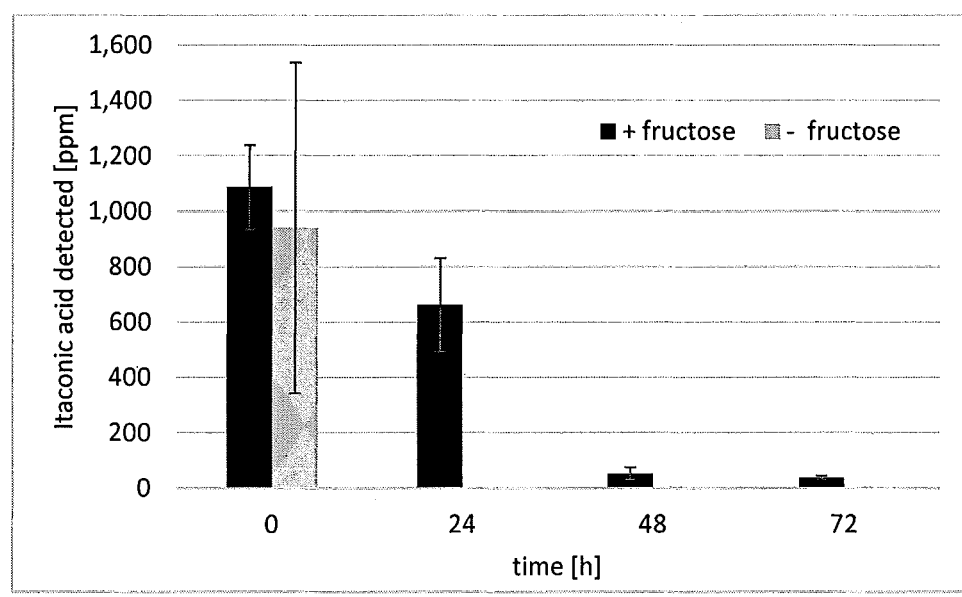
FIG. 8 shows itaconic acid levels detected in the cultures at different timepoints. The remaining titers were measured by HPLC after incubation of the cultures for 0, 24, 48 and 72 hours in presence of 1 g/L (1000 ppm) of itaconic acid in the absence (grey bars) or presence (black bars) of 1% fructose. The values obtained at 24 hours in absence of fructose were removed from this analysis due to very large discrepancies between the values obtained for the different replicates.

Results are presented in FIGS. 7 and 8. The strain *C. necator* H16 ΔphaCAB ΔA0006-9 Δicd1 Δicd2 was able to grow in a medium with itaconic acid as a sole carbon source, reaching an OD600 around 1 (FIG. 7). In addition, in the presence of fructose, the strain culture reached a higher OD600 than in presence of fructose only, indicating that this strain is able to use itaconic acid as a carbon source (FIG. 7).

These observations were confirmed by HPLC analysis of the itaconic acid titers after incubation of the cultures for 0, 24, 48 and 72 hours (FIG. 8). The amount of itaconic acid present in the cultures decreased over time, both in the presence and absence of fructose in the medium, indicating that the strain is able to degrade itaconic acid and in absence of fructose can use the compound as a sole carbon source.

Determination of the Potential Genes Involved in Itaconic Acid Degradation in *C. necator* H16

Sequences of the proteins Ict, Ich and Ccl identified in *P. aeruginosa* (encoded by PA0882, PA0878 and PA0883 respectively) and in *Y. pestis* (encoded by Y2385, Y2384 and Y2383 respectively) were used to search for homologs in *C. necator* H16 genome using tblastn (NCBI tblastn, see https: with the extension blast.ncbi.nlm.nih.gov/Blast.cgi?PROGRAM=tblastn&PAGE_TYPE=BlastSearch&LINK_LOC=blasthome of the world wide web). Potential homologs possessing at least 30% identity and similarity and at least 90% coverage with the proteins of *P. aeruginosa* are listed in Table 1. Genes H16_B0682, H16_B0679, H16_B0680 were identified as potential candidates, encoding the Ict, Ich and Ccl activities respectively, as previously described by Sasikaran et al. (Nature Chemical Biology 2014 10: 371-377). Several additional genes were also identified as potential candidates (see Table 5).

TABLE 5

Putative *C. necator* H16 homologs for *P. aeruginosa* PA0882, PA078, PA0883 encoding Ict, Ich and Ccl respectively

| Activity | Gene in *P. aeruginosa* PAO1 (from Sasikaran) | Potential genes in *C. necator* | % Identity/ % Similarity | SEQ ID NO: | Genome annotation |
|---|---|---|---|---|---|
| Ict: succinyl-CoA: itaconate-coA transferase | PA0882 | H16_A2423 | 66%/75% | 20 21 | predicted acyl-coA transferase/ carnitine dehydratase |
| | | H16_A3377 | 56%/70% | 28 29 | predicted acyl-coA transferase/ carnitine dehydratase |
| | | H16_A0099 | 36%/54% | 12 13 | bile acid-inducible operon protein F, predicted acyl-CoA transferase/ carnitine dehydratase |

TABLE 5-continued

Putative *C. necator* H16 homologs for *P. aeruginosa* PA0882, PA078, PA0883 encoding Ict, Ich and Ccl respectively

| Activity | Gene in *P. aeruginosa* PAO1 (from Sasikaran) | Potential genes in *C. necator* | % Identity/ % Similarity | SEQ ID NO: | Genome annotation |
|---|---|---|---|---|---|
| | | H16-A2770 | 35%/54% | 24, 25 | predicted acyl-CoA transferase/carnitine dehydratase |
| | | H16_A3202 | 34%/50% | 26, 27 | predicted acyl-CoA transferase/carnitine dehydratase |
| | | H16_A2386 | 31%/47% | 18, 19 | predicted acyl-CoA transferase/carnitine dehydratase |
| | | H16_B2114 | 68%/79% | 62, 63 | predicted acyl-CoA transferase/carnitine dehydratase |
| | | H16_B0682* | 60%/73% | 40, 41 | predicted acyl-CoA transferase/carnitine dehydratase |
| | | H16_B2210 | 38%/52% | 64, 65 | predicted acyl-CoA transferase/carnitine dehydratase |
| | | H16_B0688 | 34%/52% | 42, 43 | predicted acyl-CoA transferase/carnitine dehydratase |
| | | H16_B1740 | 34%/51% | 54, 55 | predicted acyl-CoA transferase/carnitine dehydratase |
| | | H16_B0707 | 32%/48% | 44, 45 | predicted acyl-CoA transferase/carnitine dehydratase |
| | | H16_B1908 | 34%/49% | 58, 59 | conserved hypothetical protein |
| | | H16_B0847 | 34%/48% | 46, 47 | acyl-CoA transferase/carnitine dehydratase |
| | | H16_B0355 | 31%/46% | 30, 31 | acyl-CoA transferase/carnitine dehydratase |
| | | H16_B0378 | 32%/51% | 32, 33 | CoA transferase |
| | | H16_B1711 | 30%/46% | 52, 53 | Formyl-coenzyme A transferase |
| | | H16_B0974 | 35%/52% | 48, 49 | predicted acyl-CoA transferase/carnitine dehydratase |
| | | H16_B0616 | 30%/48% | 34, 35 | predicted acyl-CoA transferase/carnitine dehydratase |
| | | H16_B0986 | 33%/48% | 50, 51 | CoA-transferase family III |
| | | H16_B1748 | 32%/47% | 56, 57 | predicted acyl-CoA transferase/carnitine dehydratase |
| Ich: itaconyl-CoA hydratase | PA0878 | H16_B0679* | 47%/57% | 36, 37 | conserved hypothetical protein |
| | | H16_A2424 | 47%/58% | 22, 23 | conserved hypothetical protein |
| Ccl: (S)-citramalyl-CoA lyase | PA0883 | H16_B0680* | 45%/59% | 38, 39 | citE3, citrate lyase subunit beta |
| | | H16_B2113 | 47%/55% | 60, 61 | citE4, citrate lyase subunit beta |

The genes indicated in bold* correspond to the ones previously identified by Sasikaran et al. (Nature Chemical Biology 2014 10: 371-377).

Additionally, itaconic acid could be converted to itaconyl-CoA by the ubiquitous succinyl-CoA synthetase (Suc, EC:6.2.1.5), encoded by sucC (H16_A0547) and sucD (H16_A0548).

Sequence Information for Sequences in Sequence Listing

TABLE 6

| SEQ ID NO: | Sequence Description |
|---|---|
| 1 | Amino acid sequence of *A. terreus* cis-aconitate decarboxylase CadA |
| 2 | Nucleic acid sequence of *A. terreus* cad1 sequence codon-optimized for *C. necator* |
| 3 | Amino acid sequence of GltA for *C. glutamicum* |
| 4 | Nucleic acid sequence of *C. glutamicum* gltA sequence codon-optimized for *C. necator* |
| 5 | Amino acid sequence of GltA for *C. necator* |
| 6 | Nucleic acid sequence of *C. necator* gltA sequence codon-optimized for *C. necator* |
| 7 | Nucleic acid sequence of *C. glutamicum* gltA sequence codon-optimized for *C. necator* |
| 8 | Amino acid sequence of AcnA for *C. necator* |
| 9 | Nucleic acid sequence of *C. necator* acnA sequence codon-optimized for *C. necator* |
| 10 | Amino acid sequence of AcnB for *C. necator* |
| 11 | Nucleic acid sequence of *C. necator* acnB sequence codon-optimized for *C. necator* |
| 12 | Nucleic acid sequence of *C. necator* H16 H16_A0099 |
| 13 | Amino acid sequence of *C. necator* H16 H16_A0099 |
| 14 | Nucleic acid sequence of *C. necator* H16 H16_A0547 |
| 15 | Amino acid sequence of *C. necator* H16 H16_A0547 |
| 16 | Nucleic acid sequence of *C. necator* H16 H16_A0548 |
| 17 | Amino acid sequence of *C. necator* H16 H16_A0548 |
| 18 | Nucleic acid sequence of *C. necator* H16 H16_A2386 |
| 19 | Amino acid sequence of *C. necator* H16 H16_A2386 |
| 20 | Nucleic acid sequence of *C. necator* H16 H16_A2423 |
| 21 | Amino acid sequence of *C. necator* H16 H16_A2423 |
| 22 | Nucleic acid sequence of *C. necator* H16 H16_A2424 |
| 23 | Amino acid sequence of *C. necator* H16 H16_A2424 |

TABLE 6-continued

| SEQ ID NO: | Sequence Description |
|---|---|
| 24 | Nucleic acid sequence of *C. necator* H16 H16_A2770 |
| 25 | Amino acid sequence of *C. necator* H16 H16_A2770 |
| 26 | Nucleic acid sequence of *C. necator* H16 H16_A3202 |
| 27 | Amino acid sequence of *C. necator* H16 H16_A3202 |
| 28 | Nucleic acid sequence of *C. necator* H16 H16_A3377 |
| 29 | Amino acid sequence of *C. necator* H16 H16_A3377 |
| 30 | Nucleic acid sequence of *C. necator* H16 H16_B0355 |
| 31 | Amino acid sequence of *C. necator* H16 H16_B0355 |
| 32 | Nucleic acid sequence of *C. necator* H16 H16_B0378 |
| 33 | Amino acid sequence of *C. necator* H16 H16_B0378 |
| 34 | Nucleic acid sequence of *C. necator* H16 H16_B0616 |
| 35 | Amino acid sequence of *C. necator* H16 H16_B0616 |
| 36 | Nucleic acid sequence of *C. necator* H16 H16_B0679 |
| 37 | Amino acid sequence of *C. necator* H16 H16_B0679 |
| 38 | Nucleic acid sequence of *C. necator* H16 H16_B0680 |
| 39 | Amino acid sequence of *C. necator* H16 H16_B0680 |
| 40 | Nucleic acid sequence of *C. necator* H16 H16_B0682 |
| 41 | Amino acid sequence of *C. necator* H16 H16_B0682 |
| 42 | Nucleic acid sequence of *C. necator* H16 H16_B0688 |
| 43 | Amino acid sequence of *C. necator* H16 H16_B0688 |
| 44 | Nucleic acid sequence of *C. necator* H16 H16_B0707 |
| 45 | Amino acid sequence of *C. necator* H16 H16_B0707 |
| 46 | Nucleic acid sequence of *C. necator* H16 H16_B0847 |
| 47 | Amino acid sequence of *C. necator* H16 H16_B0847 |
| 48 | Nucleic acid sequence of *C. necator* H16 H16_B0974 |
| 49 | Amino acid sequence of *C. necator* H16 H16_B0974 |
| 50 | Nucleic acid sequence of *C. necator* H16 H16_B0986 |
| 51 | Amino acid sequence of *C. necator* H16 H16_B0986 |
| 52 | Nucleic acid sequence of *C. necator* H16 H16_B1711 |
| 53 | Amino acid sequence of *C. necator* H16 H16_B1711 |
| 54 | Nucleic acid sequence of *C. necator* H16 H16_B1740 |
| 55 | Amino acid sequence of *C. necator* H16 H16_B1740 |
| 56 | Nucleic acid sequence of *C. necator* H16 H16_B1748 |
| 57 | Amino acid sequence of *C. necator* H16 H16_B1748 |
| 58 | Nucleic acid sequence of *C. necator* H16 H16_B1908 |
| 59 | Amino acid sequence of *C. necator* H16 H16_B1908 |
| 60 | Nucleic acid sequence of *C. necator* H16 H16_B2113 |
| 61 | Amino acid sequence of *C. necator* H16 H16_B2113 |
| 62 | Nucleic acid sequence of *C. necator* H16 H16_B2114 |
| 63 | Amino acid sequence of *C. necator* H16 H16_B2114 |
| 64 | Nucleic acid sequence of *C. necator* H16 H16_B2210 |
| 65 | Amino acid sequence of *C. necator* H16 H16_B2210 |

What is claimed is:

1. A process for biosynthesis of itaconic acid, said process comprising:
obtaining a *Cupriavidus necator* organism;
altering the *Cupriavidus necator* organism to express a cis-aconitate decarboxylase, a citrate synthase and an aconitate hydratase or a polypeptide or fragment thereof having the activity of a cis-aconitate decarboxylase, a citrate synthase and an aconitate hydratase,
wherein the cis-aconitate decarboxylase comprises the amino acid sequence set forth in SEQ ID NO:1 or a polypeptide having at least 90% sequence identity to the amino acid sequence set forth in SEQ ID NO:1 having cis-aconitate decarboxylase activity or a functional fragment thereof or the cis-aconitate decarboxylase is encoded by a nucleic acid sequence comprising SEQ ID NO:2 or a nucleic acid sequence having at least 90% sequence identity to the nucleic acid sequence set forth in SEQ ID NO:2 encoding a polypeptide having cis-aconitate decarboxylase activity or a functional fragment thereof, wherein the citrate synthase comprises the amino acid sequence set forth in SEQ ID NO:3 or 5 or a polypeptide having at least 90% sequence identity to the amino acid sequence set forth in SEQ ID NO:3 or 5 having citrate synthase activity or a functional fragment thereof or the citrate synthase is encoded by a nucleic acid sequence comprising SEQ ID NO:4, 6 or 7 or a nucleic acid sequence having at least 90% sequence identity to the nucleic acid sequence set forth in SEQ ID NO: 4, 6 or 7 encoding a polypeptide having citrate synthase activity or a functional fragment thereof, and
wherein the aconitate hydratase comprises the amino acid sequence set forth in SEQ ID NO:8 or 10 or a polypeptide having at least 90% sequence identity to the amino acid sequence set forth in SEQ ID NO:8 or 10 having aconitate hydratase activity or a functional fragment thereof or the aconitate hydratase is encoded by a nucleic acid sequence comprising SEQ ID NO:9 or 11 or a nucleic acid sequence having at least 90% sequence identity to the nucleic acid sequence set forth in SEQ ID NO:9 or 11 encoding a polypeptide having aconitate hydratase activity or a functional fragment thereof;
altering the *Cupriavidus necator* organism to inactivate metabolic flow downstream of cis-aconitate;
downregulating or deleting an endogenous *Cupriavidus necator* gene comprising the nucleic acid sequence of SEQ ID NO: 12, 18, 24, 26, 28, 30, 32, 34, 42, 44, 46, 48, 50, 52, 54, 56, 58 or 64; and
cultivating the altered *Cupriavidus necator* organism in a culture medium under conditions to produce itaconic acid at titers of more than 100 ppm.

2. The process of claim 1 wherein isocitrate dehydrogenase activity is inactivated.

3. The process of claim 1 wherein genes icd1 and/or icd2 are eliminated.

4. The process of claim 1 wherein the altered *Cupriavidus necator* organism is further altered to eliminate phaCAB genes involved in polyhydroxybutyrate (PHBs) production, thereby improving transformation efficiency.

5. A process for biosynthesis of itaconic acid, said process comprising:
steps of altering a *Cupriavidus necator* organism to express a cis-aconitate decarboxylase, a citrate synthase and an aconitate hydratase or a polypeptide or fragment thereof having the activity of a cis-aconitate decarboxylase, a citrate synthase and an aconitate hydratase, to inactivate metabolic flow downstream of cis-aconitate, and to downregulate or delete an endogenous *Cupriavidus necator* gene comprising a nucleic acid sequence of SEQ ID NO: 12, 18, 24, 26, 28, 30, 32, 34, 42, 44, 46, 48, 50, 52, 54, 56, 58 or 64, wherein the altered *Cupriavidus necator* organism produces itaconic acid at titers of more than 100 ppm,
wherein the cis-aconitate decarboxylase comprises the amino acid sequence set forth in SEQ ID NO:1 or a polypeptide having at least 90% sequence identity to the amino acid sequence set forth in SEQ ID NO:1 having cis-aconitate decarboxylase activity or a functional fragment thereof or the cis-aconitate decarboxylase is encoded by a nucleic acid sequence comprising SEQ ID NO:2 or a nucleic acid sequence having at least 90% sequence identity to the nucleic acid sequence set forth in SEQ ID NO:2 encoding a polypeptide having cis-aconitate decarboxylase activity or a functional fragment thereof,
wherein the citrate synthase comprises the amino acid sequence set forth in SEQ ID NO:3 or 5 or having at least 90% sequence identity to the amino acid sequence set forth in SEQ ID NO:3 or 5 having citrate synthase activity or a functional fragment thereof or the citrate synthase is encoded by a nucleic acid sequence comprising SEQ ID NO:4, 6 or 7 or a nucleic acid sequence having at least 90% sequence identity to the nucleic acid sequence set forth in SEQ ID NO: 4, 6 or 7 encoding a polypeptide having citrate synthase activity or a functional fragment thereof, and
wherein the aconitate hydratase comprises the amino acid sequence set forth in SEQ ID NO:8 or 10 or a polypeptide having at least 90% sequence identity to the amino acid sequence set forth in SEQ ID NO:8 or 10 having aconitate hydratase activity or a functional fragment thereof or the aconitate hydratase is encoded by a nucleic acid sequence comprising SEQ ID NO:9 or 11 or a nucleic acid sequence having at least 90% sequence identity to the nucleic acid sequence set forth in SEQ ID NO:9 or 11 encoding a polypeptide having aconitate hydratase activity or a functional fragment thereof; and
a step of cultivating the altered *Cupriavidus necator* organism in a culture medium under conditions to produce itaconic acid.

\* \* \* \* \*